(12) United States Patent
Cailleau et al.

(10) Patent No.: US 7,732,460 B2
(45) Date of Patent: Jun. 8, 2010

(54) HETEROCYCLIC COMPOUNDS, THEIR PREPARATION AND THEIR USE AS ANTIBACTERIALS

(75) Inventors: Nathalie Cailleau, Harlow (GB); David Thomas Davies, Harlow (GB); Alan Joseph Hennessy, Harlow (GB); Graham Elgin Jones, Harlow (GB); Timothy James Miles, Harlow (GB); Neil David Pearson, Harlow (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 12/158,397

(22) PCT Filed: Dec. 15, 2006

(86) PCT No.: PCT/GB2006/004686

§ 371 (c)(1),
(2), (4) Date: Jun. 20, 2008

(87) PCT Pub. No.: WO2007/071936

PCT Pub. Date: Jun. 28, 2007

(65) Prior Publication Data

US 2009/0036433 A1 Feb. 5, 2009

Related U.S. Application Data

(60) Provisional application No. 60/753,149, filed on Dec. 22, 2005, provisional application No. 60/866,877, filed on Nov. 22, 2006.

(51) Int. Cl.
*C07D 471/16* (2006.01)
*C07D 493/04* (2006.01)
*A61K 31/4375* (2006.01)

(52) U.S. Cl. .................................... 514/292; 546/86
(58) Field of Classification Search ................ 546/86; 514/292

See application file for complete search history.

(56) References Cited

U.S. PATENT DOCUMENTS

| 6,136,821 | A | 10/2000 | Hersperger et al. |
| 2004/0019210 | A1 | 1/2004 | Chivikas Connolly et al. |
| 2005/0101588 | A1 | 5/2005 | Grant et al. |
| 2006/0052359 | A1 | 3/2006 | Grant et al. |
| 2008/0221110 | A1 | 9/2008 | Cailleau et al. |
| 2009/0062265 | A1 | 3/2009 | Jones et al. |
| 2009/0137568 | A1 | 5/2009 | Brooks et al. |

FOREIGN PATENT DOCUMENTS

| WO | WO02/056882 | 7/2002 |
| WO | WO02/096907 | 12/2002 |
| WO | WO03/064431 | 8/2003 |
| WO | WO2008/003690 | 7/2006 |

OTHER PUBLICATIONS

Snyder et al., PubMed Abstract (J. Med. Liban 48(4): 208-214, Jul.-Aug. 2000.*
Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*

* cited by examiner

*Primary Examiner*—Kahsay T Habte
(74) *Attorney, Agent, or Firm*—Reid S. Willis; John Lemanowicz

(57) ABSTRACT

Tricyclic nitrogen containing compounds of formula (I) and their use as antibacterials.

17 Claims, No Drawings

HETEROCYCLIC COMPOUNDS, THEIR PREPARATION AND THEIR USE AS ANTIBACTERIALS

This application is a 371 of International Application No. PCT/GB2006/004686, filed 15 Dec. 2006 which claims benefit of 60/753,149, filed 22 Dec. 2005 and claims benefit of 60/866,877, filed 22 Nov. 2006.

This invention relates to novel compounds, compositions containing them and their use as antibacterials.

WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO2006002047, WO2006014580, WO2006010040, WO2006017326, WO2006012396, WO2006017468, WO2006020561, WO2006081179, WO2006081264, WO2006081289, WO2006081178, WO2006081182, WO01/25227, WO02/40474, WO02/07572, WO2004024712, WO2004024713, WO2004035569, WO2004087647, WO2004089947, WO2005016916, WO2005097781, WO2006010831, WO2006021448, WO2006032466, WO2006038172, WO2006046552, WO2006099884 and WO2006105289 disclose quinoline, naphthyridine, morpholine, cyclohexane, piperidine and piperazine derivatives having antibacterial activity. WO2004104000 discloses tricyclic condensed ring compounds capable of selectively acting on cannabinoid receptors.

This invention provides a compound of formula (I) or a pharmaceutically acceptable salt, solvate and/or N-oxide thereof:

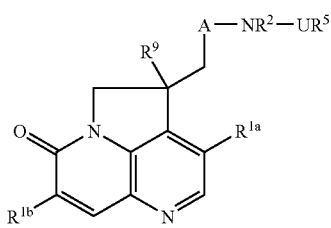

wherein:
$R^{1a}$ and $R^{1b}$ are independently selected from hydrogen; halogen; cyano; $(C_{1-6})$alkyl; $(C_{1-6})$alkylthio; trifluoromethyl; trifluoromethoxy; carboxy; hydroxy optionally substituted with $(C_{1-6})$alkyl or $(C_{1-6})$alkoxy-substituted $(C_{1-6})$alkyl; $(C_{1-6})$alkoxy-substituted $(C_{1-6})$alkyl; hydroxy $(C_{1-6})$alkyl; an amino group optionally N-substituted by one or two $(C_{1-6})$alkyl, formyl, $(C_{1-6})$alkylcarbonyl or $(C_{1-6})$alkylsulphonyl groups; or aminocarbonyl wherein the amino group is optionally substituted by $(C_{1-4})$alkyl;
$R^2$ is hydrogen, or $(C_{1-4})$alkyl, or together with $R^6$ forms Y as defined below;
A is a group (ia) or (ib):

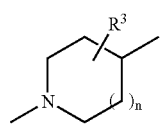

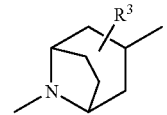

in which: $R^3$ is as defined for $R^{1a}$ or $R^{1b}$ or is oxo and n is 1 or 2;
or A is a group (ii)

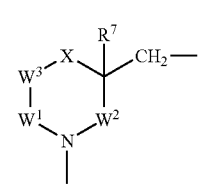

$W^1$, $W^2$ and $W^3$ are $CR^4R^8$
or $W^2$ and $W^3$ are $CR^4R^8$ and $W^1$ represents a bond between $W^3$ and N.
X is O, $CR^4R^8$, or $NR^6$;
one $R^4$ is as defined for $R^{1a}$ and $R^{1b}$ and the remainder and $R^8$ are hydrogen or one $R^4$ and $R^8$ are together oxo and the remainder are hydrogen;
$R^6$ is hydrogen or $(C_{1-6})$alkyl; or together with $R^2$ forms Y;
$R^7$ is hydrogen; halogen; hydroxy optionally substituted with $(C_{1-6})$alkyl; or $(C_{1-6})$alkyl;
Y is $CR^4R^8CH_2$; $CH_2CR^4R^8$; $(C=O)$; $CR^4R^8$; $CR^4R^8(C=O)$; or $(C=O)CR^4R^8$;
or when X is $CR^4R^8$, $R^8$ and $R^7$ together represent a bond;
U is selected from CO, and $CH_2$ and
$R^5$ is an optionally substituted bicyclic carbocyclic or heterocyclic ring system (B):

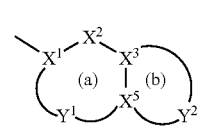

containing up to four heteroatoms in each ring in which
at least one of rings (a) and (b) is aromatic;
$X^1$ is C or N when part of an aromatic ring, or $CR^{14}$ when part of a non-aromatic ring;
$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;
$X^3$ and $X^5$ are independently N or C;
$Y^1$ is a 0 to 4 atom linker group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring;
$Y^2$ is a 2 to 6 atom linker group, each atom of $Y^2$ being independently selected from N, $NR^{13}$, O, $S(O)_x$, CO, $CR^{14}$ when part of an aromatic or non-aromatic ring or may additionally be $CR^{14}R^{15}$ when part of a non aromatic ring;
each of $R^{14}$ and $R^{15}$ is independently selected from: H; $(C_{1-4})$alkylthio; halo; carboxy$(C_{1-4})$alkyl; $(C_{1-4})$alkyl; $(C_{1-4})$alkoxycarbonyl; $(C_{1-4})$alkylcarbonyl; $(C_{1-4})$alkoxy $(C_{1-4})$alkyl; hydroxy; hydroxy$(C_{1-4})$alkyl; $(C_{1-4})$alkoxy; nitro; cyano; carboxy; amino or aminocarbonyl optionally mono- or di-substituted by $(C_{1-4})$alkyl; or
$R^{14}$ and $R^{15}$ may together represent oxo;

each $R^{13}$ is independently H; trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; $(C_{1-4})$alkoxycarbonyl; $(C_{1-4})$alkylcarbonyl; $(C_{1-6})$alkylsulphonyl; aminocarbonyl wherein the amino group is optionally mono or disubstituted by $(C_{1-4})$alkyl;

each x is independently 0, 1 or 2; and $R^9$ is fluoro or hydroxy.

This invention also provides a method of treatment of bacterial infections in mammals, particularly in man, which method comprises the administration to a mammal in need of such treatment an effective amount of a compound of formula (I), or a pharmaceutically acceptable salt, solvate and/or N-oxide thereof.

The invention also provides the use of a compound of formula (I), or a pharmaceutically acceptable salt, solvate and/or N-oxide thereof, in the manufacture of a medicament for use in the treatment of bacterial infections in mammals.

The invention also provides a pharmaceutical composition comprising a compound of formula (I), or a pharmaceutically acceptable salt, solvate and/or N-oxide thereof, and a pharmaceutically acceptable carrier.

In a particular aspect each $R^{1a}$ and $R^{1b}$ is independently hydrogen, $(C_{1-4})$alkoxy, $(C_{1-4})$alkylthio, $(C_{1-4})$alkyl, cyano, carboxy, hydroxymethyl or halogen; more particularly hydrogen, methoxy, methyl, cyano, or halogen.

In certain embodiments each $R^{1a}$ and $R^{1b}$ is hydrogen, methoxy, methyl, or halogen, such as chloro or fluoro. In some embodiments only one group $R^{1a}$ or $R^{1b}$ is other than hydrogen, such as $R^{1a}$ chloro, fluoro or methoxy. In other embodiments both $R^{1a}$ and $R^{1b}$ are other than hydrogen, more particularly halogen, such as $R^{1a}$ fluoro and $R^{1b}$ chloro or fluoro.

In a particular aspect $R^2$ is hydrogen.

Particular examples of $R^3$ include hydrogen; optionally substituted hydroxy; optionally substituted amino; halogen; $(C_{1-4})$ alkyl; 1-hydroxy-$(C_{1-4})$ alkyl; optionally substituted aminocarbonyl. More particular $R^3$ groups are hydrogen; $CONH_2$; 1-hydroxyalkyl e.g. $CH_2OH$; optionally substituted hydroxy e.g. methoxy; optionally substituted amino; and halogen, in particular fluoro. Most particularly $R^3$ is hydrogen, hydroxy or fluoro.

In a particular aspect, the stereochemistry at the carbon atom to which the group $R^9$ is attached is S.

In a particular aspect, when A is (ia), n is 1. In a further aspect $R^3$ is in the 3- or 4-position. In a more particular aspect, A is (ia), n is 1 and $R^3$ is in the 3-position, and more particularly is cis to the $NR^2$ group.

In particular embodiments, A is a group (ia) in which n is 1 and $R^3$ is hydrogen or hydroxy.

In a particular aspect, when A is (ii), X is $CR^4R^8$, $R^8$ is H and $R^4$ is H or OH and more particularly OH is trans to $R^7$. In a further aspect $W^1$ is a bond. In another aspect $R^7$ is H. In particular embodiments $W^1$ is a bond, X, $W^2$ and $W^3$ are each $CH_2$ and $R^7$ is H.

In certain embodiments U is $CH_2$.

In certain embodiments $R^5$ is an aromatic heterocyclic ring (B) having 8-11 ring atoms including 2-4 heteroatoms of which at least one is N or $NR^{13}$ in which, in particular embodiments, $Y^2$ contains 2-3 heteroatoms, one of which is 5 and 1-2 are N, with one N bonded to $X^3$.

In alternative embodiments the heterocyclic ring (B) has ring (a) aromatic selected from optionally substituted benzo, pyrido and pyridazino and ring (b) non aromatic and $Y^2$ has 3-5 atoms, more particularly 4 atoms, including at least one heteroatom, with O, S, $CH_2$ or $NR^{13}$ bonded to $X^5$ where $R^{13}$ is other than hydrogen, and either NHCO bonded via N to $X^3$, or O, S, $CH_2$ or NH bonded to $X^3$. In a particular aspect the ring (a) contains aromatic nitrogen, and more particularly ring (a) is pyridine or pyrazine. Examples of rings (B) include optionally substituted:

(a) and (b) Aromatic 1H-pyrrolo[2,3-b]-pyridin-2-yl, 1H-pyrrolo[3,2-b]-pyridin-2-yl, 3H-imidazo[4,5-b]-pyrid-2-yl, 3H-quinazolin-4-one-2-yl (4(1H)-quinazolinone-2-yl or 4-oxo-1,4-dihydro-2-quinazolinyl), benzimidazol-2-yl, benzo[1,2,3]-thiadiazol-5-yl, benzo[1,2,5]-oxadiazol-5-yl, benzofur-2-yl, benzothiazol-2-yl, benzo[b]thiophen-2-yl, benzoxazol-2-yl, chromen-4-one-3-yl, imidazo[1,2-a]pyridin-2-yl, imidazo-[1,2-a]-pyrimidin-2-yl, indol-2-yl, indol-6-yl, isoquinolin-3-yl, [1,8]-naphthyridine-3-yl, oxazolo[4,5-b]-pyridin-2-yl, quinolin-2-yl, quinolin-3-yl, quinoxalin-2-yl, indan-2-yl, naphthalen-2-yl, 1,3-dioxo-isoindol-2-yl, benzimidazol-2-yl, benzothiophen-2-yl, 1H-benzotriazol-5-yl, 1H-indol-5-yl, 3H-benzooxazol-2-one-6-yl, 3H-benzooxazol-2-thione-6-yl, 3H-benzothiazol-2-one-5-yl, 3H-quinazolin-4-one-6-yl, 4-oxo-4H-pyrido[1,2-a]pyrimidin-3-yl, benzo[1,2,3]thiadiazol-6-yl, benzo[1,2,5]thiadiazol-5-yl, benzo[1,4]oxazin-2-one-3-yl, benzothiazol-5-yl, benzothiazol-6-yl, cinnolin-3-yl, imidazo[1,2-a]pyridazin-2-yl, imidazo[1,2-b]pyridazin-2-yl, pyrazolo[1,5-a]pyrazin-2-yl, pyrazolo[1,5-a]pyridin-2-yl, pyrazolo[1,5-a]pyrimidin-6-yl, pyrazolo[5,1-c][1,2,4]triazin-3-yl, pyrido[1,2-a]pyrimidin-4-one-2-yl, pyrido[1,2-a]pyrimidin-4-one-3-yl, quinazolin-2-yl, quinoxalin-6-yl, thiazolo[3,2-a]pyrimidin-5-one-7-yl, thiazolo[5,4-b]pyridin-2-yl, thieno[3,2-b]pyridin-6-yl, thiazolo[5,4-b]pyridin-6-yl, 4-oxo-4H-pyrido[1,2-a]pyrimidin-2-yl, 1-oxo-1,2-dihydro-isoquinolin-3-yl, thiazolo[4,5-b]pyridin-5-yl, [1,2,3]thiadiazolo[5,4-b]pyridin-6-yl, 2H-isoquinolin-1-one-3-yl, 1,8-naphthyridin-2-yl, 2,1,3-benzooxadiazol-5-yl, 2(1H)-quinoxalinone-3-yl, (a) is Non Aromatic (2S)-2,3-dihydro-1H-indol-2-yl, (2S)-2,3-dihydro-benzo[1,4]dioxine-2-yl, 3-(R,S)-3,4-dihydro-2H-benzo[1,4]thiazin-3-yl, 3-(R)-2,3-dihydro-[1,4]dioxino[2,3-b]pyridin-3-yl, 3-(S)-2,3-dihydro-[1,4]dioxino[2,3-b]pyridin-3-yl, 2,3-dihydro-benzo[1,4]dioxan-2-yl, 3-substituted-3H-quinazolin-4-one-2-yl, (b) is Non Aromatic 1,1,3-trioxo-1,2,3,4-tetrahydrol $1^6$-benzo[1,4]thiazin-6-yl, benzo[1,3]dioxol-5-yl, 2,3-dihydro-benzo[1,4]dioxin-6-yl, 2-oxo-2,3-dihydro-benzooxazol-6-yl, 3-substituted-3H-benzooxazol-2-one-6-yl, 3-substituted-3H-benzooxazole-2-thione-6-yl, 3-substituted-3H-benzothiazol-2-one-6-yl (3-substituted-2-oxo-2,3-dihydro-1,3-benzothiazol-6-yl), 4H-benzo[1,4]oxazin-3-one-6-yl (3-oxo-3,4-dihydro-2H-benzo[1,4]oxazin-6-yl), 4H-benzo[1,4]thiazin-3-one-6-yl (3-oxo-3,4-dihydro-2H-benzo[1,4]thiazin-6-yl), 4H-benzo[1,4]oxazin-3-one-7-yl, 4-oxo-2,3,4,5-tetrahydro-benzo[b][1,4]thiazepine-7-yl, 5-oxo-2,3-dihydro-5H-thiazolo[3,2-a]pyrimidin-6-yl, 1H-pyrido[2,3-b][1,4]thiazin-2-one-7-yl (2-oxo-2,3-dihydro-1H-pyrido[2,3-b]thiazin-7-yl), 2,3-dihydro-1H-pyrido[2,3-b][1,4]thiazin-7-yl, 2-oxo-2,3-dihydro-1H-pyrido[3,4-b]thiazin-7-yl, 2,3-dihydro-[1,4]dioxino[2,3-b]pyridin-6-yl, 2,3-dihydro-[1,4]dioxino[2,3-c]pyridin-7-yl, 2,3-dihydro-[1,4]dioxino[2,3-b]pyridin-7-yl, 3,4-dihydro-2H-benzo[1,4]oxazin-6-yl, 3,4-dihydro-2H-benzo[1,4]thiazin-6-yl, 3-oxo-3,4-dihydro-2H-pyrido[3,2-b][1,4]oxazin-6-yl, 3,4-dihydro-2H-pyrido[3,2-b][1,4]thiazin-6-yl, 3-oxo-3,4-dihydro-2H-pyrido[3,2-b][1,4]thiazin-6-yl, 3,4-dihydro-1H-quinolin-2-one-7-yl, 3,4-dihydro-1H-quinoxalin-2-one-7-yl, 6,7-dihydro-4H-pyrazolo[1,5-a]pyrimidin-5-one-2-yl, 5,6,7,8-tetrahydro-[1,8]naphthyridin-2-yl, 2-oxo-3,4-dihydro-1H-[1,8]naphthyridin-6-yl, 6-oxo-6,7-dihydro-5H-8-thia-1,2,5-triaza-naphthalen-3-yl, 2-oxo-2,3-dihydro-1H-pyrido[3,4-b][1,4]oxazin-7-yl, 2-oxo-2,3-dihydro-1H-pyrido[2,3-b][1,4]oxazin-7-yl, 6,7-dihydro-[1,4]dioxino[2,3-d]pyrimidin-2-yl, [1,3]oxathiolo[5,4-c]pyridine-6-yl, 3,4-dihydro-2H-pyrano[2,3-c]pyridine-6-yl, 2,3-dihydro-1,4-benzodioxin-7-yl, 2,3-dihydro[1,4]oxathiino[2,3-c]pyridine-7-yl, 2,3-dihydrofuro[2,3-c]pyridin-5-yl, 2,3-dihydro-1-benzofuran-5-yl, 6,7-dihydro[1,4]oxathiino[3,2-c]pyridazin-3-yl, 6,7-dihydro[1,4]oxathiino[2,3-c]pyridazin-3-yl, 6,7-dihydro[1,4]dioxino[2,3-c]pyridazin-3-yl, 6,7-dihydro-5H-pyrano[2,3-c]pyridazin-3-yl, 2,3-dihydro[1,4]oxathiino[3,2-c]pyridin-7-yl, 5,6-dihydrofuro[2,3-c]pyridazin-3-yl, 1,2,3-benzothiadiazol-6-yl, 7-oxo-1,5,6,7-tetrahydro-1,8-naphthyridin-2-yl.

In some embodiments $R^{13}$ is H if in ring (a) or in addition $(C_{1-4})$alkyl such as methyl or isopropyl when in ring (b). More particularly, in ring (b) $R^{13}$ is H when $NR^{13}$ is bonded to $X^3$ and $(C_{1-4})$alkyl when $NR^{13}$ is bonded to $X^5$.

In further embodiments $R^{14}$ and $R^{15}$ are independently selected from hydrogen, halo, hydroxy, $(C_{1-4})$ alkyl, $(C_{1-4})$ alkoxy, nitro and cyano. More particularly $R^{15}$ is hydrogen.

More particularly each $R^{14}$ is selected from hydrogen, chloro, fluoro, hydroxy, methyl, methoxy, nitro and cyano. Still more particularly $R^{14}$ is selected from hydrogen, fluorine or nitro.

Most particularly $R^{14}$ and $R^{15}$ are each H.

Particular groups $R^5$ include:
[1,2,3]thiadiazolo[5,4-b]pyridin-6-yl
1H-pyrrolo[2,3-b]pyridin-2-yl
2,3-dihydro-[1,4]dioxino[2,3-b]pyridin-6-yl
2,3-dihydro-[1,4]dioxino[2,3-b]pyridin-7-yl
2,3-dihydro-[1,4]dioxino[2,3-c]pyridin-7-yl
2,3-dihydro-benzo-1,4-dioxin-6-yl
2-oxo-2,3-dihydro-1H-pyrido[2,3-b][1,4]oxazin-7-yl
2-oxo-2,3-dihydro-1H-pyrido[2,3-b][1,4]thiazin-7-yl
3,4-dihydro-2H-benzo[1,4]oxazin-6-yl
3-methyl-2-oxo-2,3-dihydro-benzooxazol-6-yl
3-oxo-3,4-dihydro-2H-benzo[1,4]oxazin-6-yl
3-oxo-3,4-dihydro-2H-pyrido[3,2-b][1,4]oxazin-6-yl
3-oxo-3,4-dihydro-2H-benzo[1,4]thiazin-6-yl (4H-benzo[1,4]thiazin-3-one-6-yl) 4-oxo-4H-pyrido[1,2-a]pyrimidin-2-yl
6-nitro-benzo[1,3]dioxol-5-yl
7-fluoro-3-oxo-3,4-dihydro-2H-benzo[1,4]oxazin-6-yl
8-hydroxy-1-oxo-1,2-dihydro-isoquinolin-3-yl
8-hydroxyquinolin-2-yl
benzo[1,2,3]thiadiazol-5-yl
benzo[1,2,5]thiadiazol-5-yl
benzothiazol-5-yl
thiazolo-[5,4-b]pyridin-6-yl
3-oxo-3,4-dihydro-2H-pyrido[3,2-b][1,4]thiazin-6-yl
7-chloro-3-oxo-3,4-dihydro-2H-pyrido[3,2-b][1,4]thiazin-6-yl
7-fluoro-3-oxo-3,4-dihydro-2H-pyrido[3,2-b][1,4]thiazin-6-yl
2-oxo-2,3-dihydro-1H-pyrido[3,4-b][1,4]thiazin-7-yl
[1,3]oxathiolo[5,4-c]pyridin-6-yl
3,4-dihydro-2H-pyrano[2,3-c]pyridin-6-yl
5-carbonitro-2,3-dihydro-1,4-benzodioxin-7-yl
2,3-dihydro[1,4]oxathiino[2,3-c]pyridin-7-yl
2,3-dihydrofuro[2,3-c]pyridin-5-yl
5-fluoro-2,3-dihydro-1,4-benzodioxino-7-yl
2,3-dihydro-1-benzofuran-5-yl
6-oxo-dihydro-5H-pyridazino[3,4-b][1,4]thiazin-3-yl
7-oxo-1,5,6,7-tetrahydro-1,8-naphthyridin-2-yl
quinoxalin-2-yl
1,8-naphthyridin-2-yl
isoquinolin-3-yl
quinolin-3-yl
2(1H)-quinoxalinone-3-yl
4(1H)-quinazolinone-2-yl (3H-quinazolin-4-one-2-yl or 4-oxo-1,4-dihydro-2-quinazolinyl)
7-chloro-3-oxo-3,4-dihydro-2H-pyrido[3,2-b][1,4]oxazin-6-yl
quinoxalin-6-yl
2,3-dihydro-1-benzofuran-5-yl
1-(1-methylethyl)-1H-1,2,3-benzotriazol-5-yl
2,1,3-benzooxadiazol-5-yl
quinolin-2-yl
1H-indol-6-yl
4-fluoro-1H-benzimidazol-2-yl
6,7-dihydro[1,4]oxathiino[3,2-c]pyridazin-3-yl
6,7-dihydro[1,4]oxathiino[2,3-c]pyridazin-3-yl
6,7-dihydro[1,4]dioxino[2,3-c]pyridazin-3-yl
6,7-dihydro-5H-pyrano[2,3-c]pyridazin-3-yl
2,3-dihydro[1,4]oxathiino[3,2-c]pyridin-7-yl
7-carbonitro-2,3-dihydro-1-benzofuran-5-yl
5,6-dihydrofuro[2,3-c]pyridazin-3-yl
3-methyl-2-oxo-2,3-dihydro-1,3-benzothiazol-6-yl
1,2,3-benzothiadiazol-6-yl
5,7-difluoro-1H-indol-2-yl especially
3-oxo-3,4-dihydro-2H-pyrido[3,2-b][1,4]oxazin-6-yl
3-oxo-3,4-dihydro-2H-pyrido[3,2-b][1,4]thiazin-6-yl
6,7-dihydro[1,4]dioxino[2,3-c]pyridazin-3-yl
6,7-dihydro[1,4]oxathiino[2,3-c]pyridazin-3-yl
6,7-dihydro[1,4]oxathiino[3,2-c]pyridazin-3-yl
2,3-dihydro-[1,4]dioxino[2,3-c]pyridin-7-yl
[1,3]oxathiolo[5,4-c]pyridin-6-yl
2,3-dihydro-1,4-benzodioxin-6-yl
2,3-dihydro[1,4]oxathiino[2,3-c]pyridin-7-yl
3,4-dihydro-2H-pyrano[2,3-c]pyridin-6-yl
2,3-dihydro[1,4]oxathiino[3,2-c]pyridin-7-yl
6,7-dihydro-5H-pyrano[2,3-c]pyridazin-3-yl.

When used herein, the term "alkyl" includes groups having straight and branched chains, for instance, methyl, ethyl, n-propyl, iso-propyl, n-butyl, iso-butyl, sec-butyl, t-butyl, pentyl and hexyl. The term 'alkenyl' should be interpreted accordingly.

Halo or halogen includes fluoro, chloro, bromo and iodo.

Haloalkyl moieties include 1-3 halogen atoms.

Compounds within the invention contain a heterocyclyl group and may occur in two or more tautomeric forms depending on the nature of the heterocyclyl group; all such tautomeric forms are included within the scope of the invention.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Furthermore, it will be understood that phrases such as "a compound of formula (I) or a pharmaceutically acceptable salt, solvate or N-oxide thereof" are intended to encompass the compound of formula (I), an N-oxide of formula (I), a pharmaceutically acceptable salt of the compound of formula (I), a solvate of formula (I), or any pharmaceutically acceptable combination of these. Thus by way of non-limiting example used here for illustrative purpose, "a compound of formula (I) or a pharmaceutically acceptable salt or solvate thereof" may include a pharmaceutically acceptable salt of a compound of formula (I) that is further present as a solvate.

Since the compounds of formula (I) are intended for use in pharmaceutical compositions it will readily be understood that in particular embodiments they are provided in substantially pure form, for example at least 60% pure, more suitably at least 75% pure and particularly at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and more particularly from 10 to 59% of a compound of the formula (I) or pharmaceutically acceptable salt, solvate and/or N-oxide thereof.

Particular compounds according to the invention include those mentioned in the examples and their pharmaceutically acceptable N-oxides, salts and solvates.

Pharmaceutically acceptable salts of the above-mentioned compounds of formula (I) include the acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. Compounds of formula (I) may also be prepared as the N-oxide. The invention extends to all such salts, solvates and/or N-oxides.

Certain of the compounds of formula (I) may exist in the form of optical isomers, e.g. diastereoisomers and mixtures of isomers in all ratios, e.g. racemic mixtures. The invention includes all such forms, in particular the pure isomeric forms. For example the invention includes enantiomers and diastereoisomers at the attachment points of $NR^2$, $R^3$ and/or $R^9$. The different isomeric forms may be separated or resolved one from the other by conventional methods, or any given isomer may be obtained by conventional synthetic methods or by stereospecific or asymmetric syntheses.

In a further aspect of the invention there is provided a process for preparing compounds of formula (I), and pharmaceutically acceptable salts, solvates and/or N-oxides thereof, which process comprises reacting a compound of formula (IIA):

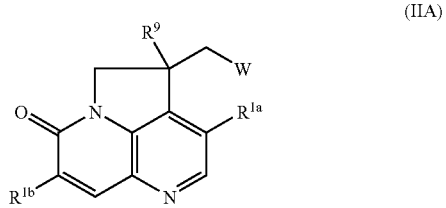

(IIA)

with a compound $HA-N(R^{20})R^{2'}$ in which W is a leaving group, $R^{20}$ is $UR^5$ or a group convertible thereto and $R^{2'}$ is $R^2$ or a group convertible thereto, and A, $R^{1a}$, $R^{1b}$, $R^2$, $R^9$, U and $R^5$ are as defined in formula (I), to give a compound of formula (IIB):

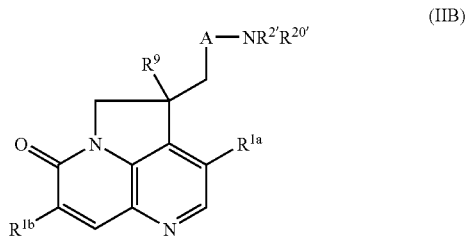

(IIB)

and thereafter optionally or as necessary converting $R^{20}$ and $R^{2'}$ to $UR^5$ and $R^2$, interconverting any variable groups, and/or forming a pharmaceutically acceptable salt, solvate or N-oxide thereof.

The reaction is carried out under conventional conditions for amine coupling such as reacting together in the presence of a suitable base, such as sodium carbonate or triethylamine, in a suitable solvent such as ethanol or N,N-dimethylformamide at temperatures between ambient and 60° C. Where $R^9$ is OH, treatment with base can afford an epoxide which can react with amines to give (IIB). Such reactions may proceed through this epoxide without the need for isolation.

The leaving group may be any conventional group such as methanesulfonyl or metlhylbenzenesulfonyl. Conveniently one of $R^{20}$ and $R^{2'}$ is an N-protecting group, such as such as t-butoxycarbonyl, benzyloxycarbonyl or 9-fluorenylmethyloxycarbonyl. This may be removed by several methods well known to those skilled in the art (for examples see *Protective Groups in Organic Synthesis*, T. W. Greene and P. G. M. Wuts, Wiley-Interscience, 1999), for example conventional acid hydrolysis with, for example, trifluoracetic acid or hydrochloric acid.

The invention further provides compounds of formula (IIB) in which $R^{20}$ is hydrogen.

The free amine of formula (IIB) in which $R^{20}$ is hydrogen may be converted to $NR^2UR^5$ by conventional means such as amide or sulphonamide formation with an acyl derivative $R^5COW$ or $R^5SO_2W$, for compounds where U is CO or $SO_2$ or, where U is $CH_2$, by alkylation with an alkyl halide $R^5CH_2$-halide in the presence of base, acylation/reduction with an acyl derivative $R^5COW$ or reductive alkylation with an aldehyde $R^5CHO$ under conventional conditions (see for examples Smith, M. B.; March, J. M. *Advanced Organic Chemistry*, Wiley-Interscience). The appropriate reagents containing the required $R^5$ group are known compounds or may be prepared analogously to known compounds, see for example WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO06002047, WO06014580, WO06010040, WO06017326, WO06012396, WO06017468, WO06020561 and EP0559285.

Where $R^5$ contains an NH group, this may be protected with a suitable N-protecting group such as t-butoxycarbonyl, benzyloxycarbonyl or 9-fluorenylmethyloxycarbonyl during the coupling of the $R^5$ derivative with the free amine of formula (IIB). The protecting group may be removed by conventional methods, such as by treatment with trifluoroacetic acid.

Conveniently the resolution of enantiomers at the attachment position of $R^9$ is carried out on the compound of formula (I), (IIA) or (IIB), by any conventional method such as preparative high performance liquid chromatography.

The compound of formula (IIA) may be prepared by the following Scheme 1:

Scheme 1

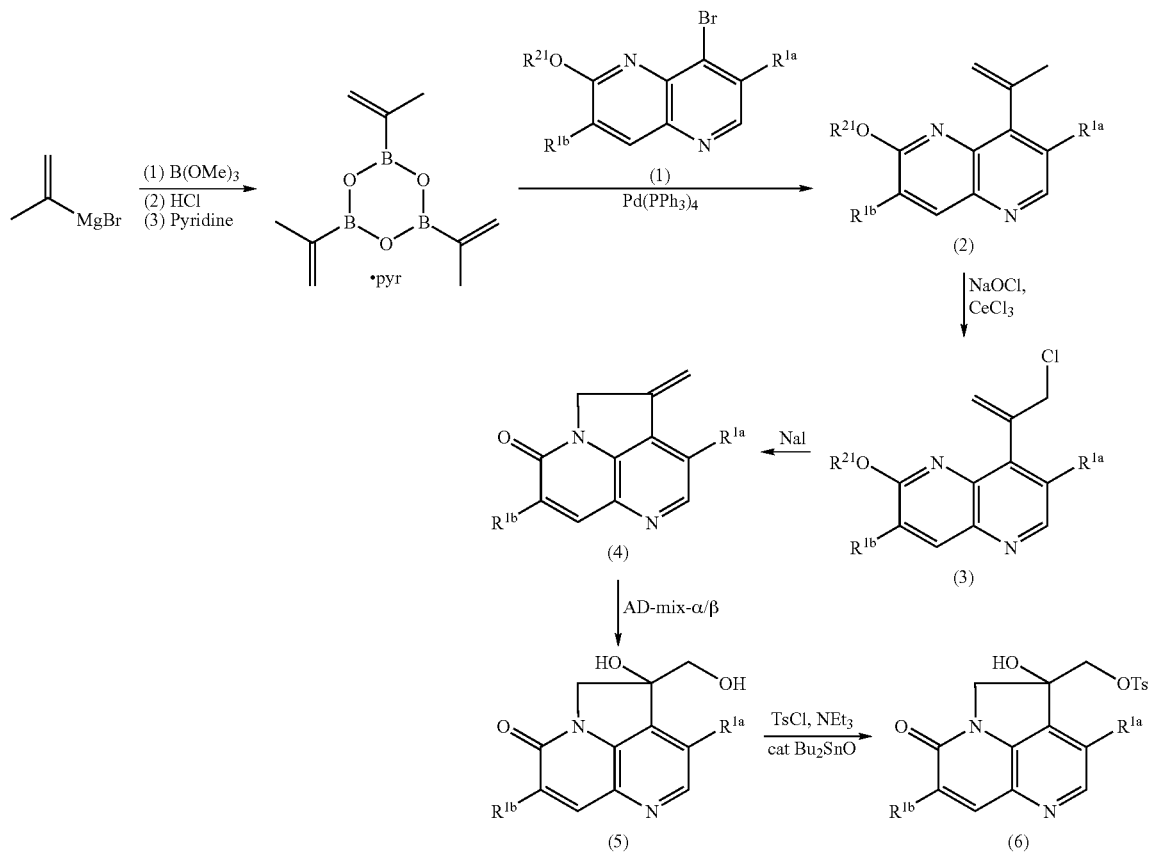

TsCl = tosyl chloride
TsO = tosylate

The bromo-naphthyridine (1) is converted to a methylvinyl-analogue (2) under Suzuki conditions. The methyl group is functionalised with NaOCl to give the chloroanalogue (3) which cyclises to give the vinyl tricyclic naphthyridone (4). The vinyl tricyclic naphthyridone (4) is converted to the dihydroxylated analogue (5) using AD-mix-α and/or β, a mixture of potassium osmate, potassium ferricyanide and chiral alkaloid-derived ligand known to dihydroxylate olefins in a chiral manner, see K. B. Sharpless et al, Chem. Rev., 1994, 94, 2483.

Alternative chiral ligands may also be used such as hydroquinine anthraquinone-1,4-diyl diether. The primary hydroxyl group is functionalised to the leaving group W of the compound of formula (IIA) conventionally, for exampe to the tosylate (6) with tosyl chloride/dibutyltin oxide.

The invention also provides compounds of formula (5).

An alternative route to a vinyl derivative (4) in which $R^{1a}$ is F and $R^{1b}$ is H is shown in Scheme 2:

Scheme 2

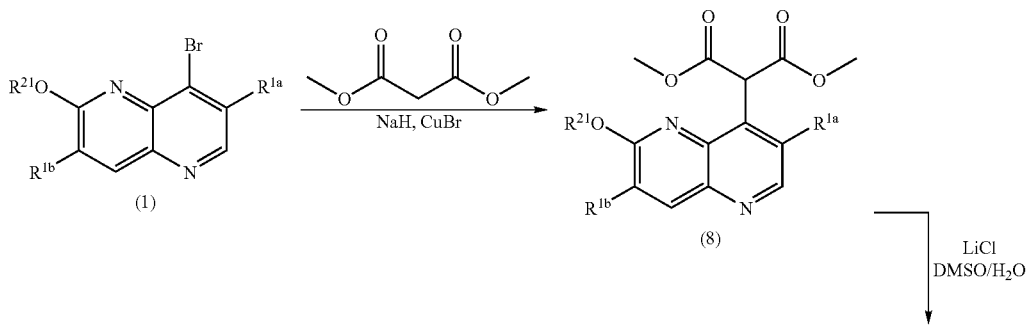

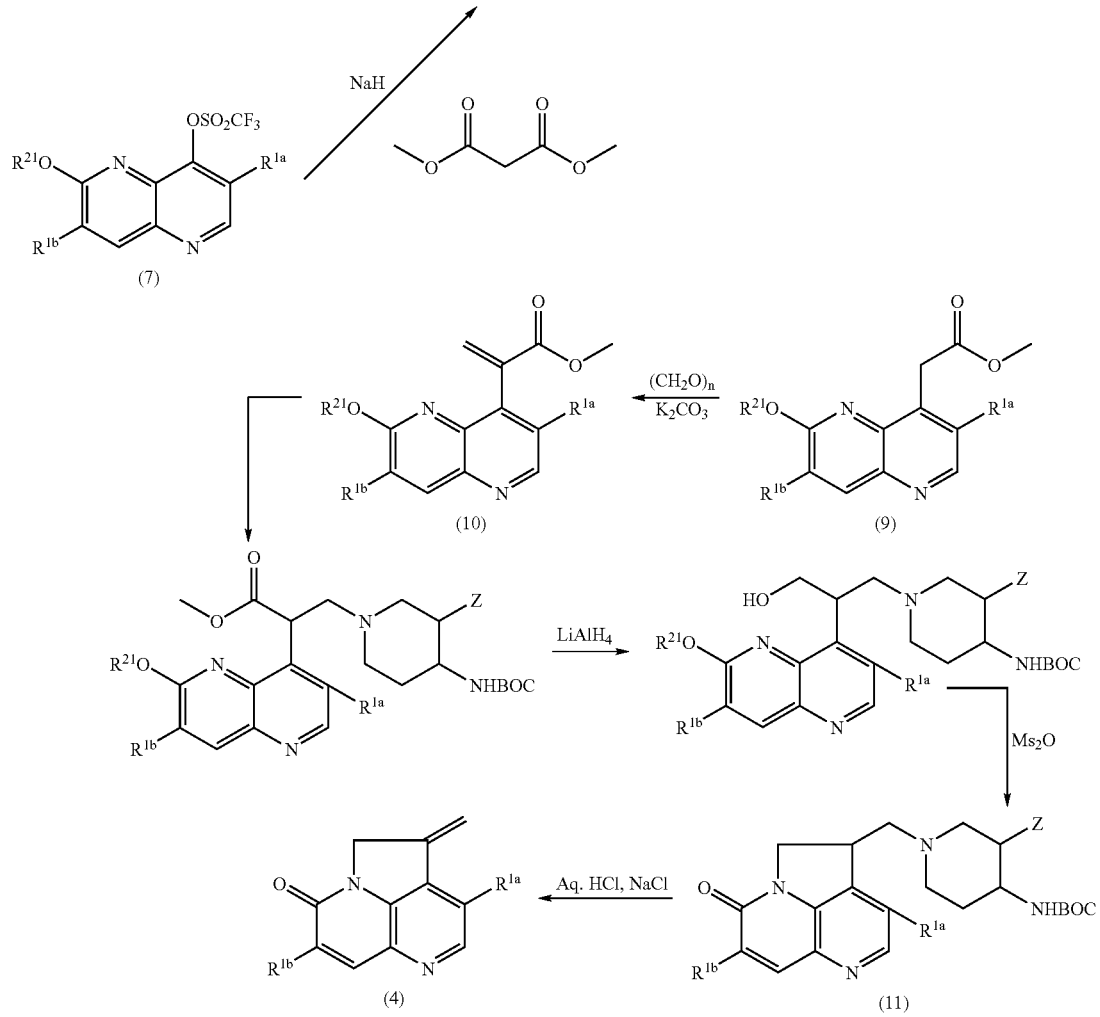

DMSO = dimethylsulphoxide
(CH$_2$O)$_n$ = paraformaldehyde
BOC = t-butoxycarbonyl
Ms$_2$O = methansulphonic anhydride Bromides such as (1) can be converted to diester (8) by copper-catalysed reaction with the sodium salt of dimethyl malonate, while triflates such as (7) can be converted directly to (8) by reaction with the sodium salt of dimethyl malonate. The diesters can be converted to monoesters (9) using the conditions of Krapcho et al, J. Org. Chem., 1987, 52(9), 1880, by heating a mixture of diester with LiCl in DMSO/water at 100° C. for 24 h. Condensation with paraformaldehyde gives the propenoate (10) then the sequence of Michael addition with an aminopiperidine (Z is H or OH), reduction of ester to alcohol, and cyclisation gives the tricyclic derivatives (11). Acid-catalysed retro-Michael reaction then gives the key olefins (4), which can then be further transformed according to the methods described in Scheme 1.

Interconversions of $R^{1a}$, $R^{1b}$, $R^2$, A, $R^5$ and $R^9$ are conventional. In compounds which contain an optionally protected hydroxy group, suitable conventional hydroxy protecting groups which may be removed without disrupting the remainder of the molecule include acyl and alkylsilyl groups. N-protecting groups are removed by conventional methods.

$R^9$ hydroxy may be converted to fluoro at any point in the synthesis, such as on intermediate (5), by treatment with a fluorinating agent such as (diethylamino)sulphur trifluoride.

Interconversion of $R^{1a}$ and $R^{1b}$ groups may be carried out conventionally, on compounds of formula (I) or earlier intermediates such as (5) or the free amine of formula (IIB) in which $R^{20}$ is hydrogen. For example $R^{1a}$ or $R^{1b}$ methoxy is convertible to $R^{1a}$ or $R^{1b}$ hydroxy by treatment with lithium and diphenylphosphine (general method described in Ireland et al, J. Amer. Chem. Soc., 1973, 7829) or HBr. Alkylation of the hydroxy group with a suitable alkyl derivative bearing a leaving group such as halide, yields $R^{1a}$ or $R^{1b}$ substituted alkoxy. $R^{1a}$ halogen is convertible to other $R^{1a}$ by conventional means, for example to hydroxy, alkylthiol (via thiol) and amino using metal catalysed coupling reactions, for example using copper as reviewed in Synlett (2003), 15, 2428-2439 and Angewandte Chemie, International Edition, 2003, 42(44), 5400-5449. $R^{1a}$ fluoro may be converted to methoxy by treatment with sodium methoxide in methanol. $R^{1b}$ halo such as bromo may be introduced by the general method of M. A. Alonso et al, Tetrahedron 2003, 59(16), 2821 or P. Imming et al, Eur. J. Med. Chem., 2001, 36 (4), 375. $R^{1b}$ halo such as chloro may be introduced by treatment with N-chlorosuccinimide. $R^{1a}$ or $R^{1b}$ halo such as bromo may be converted to cyano by treatment with copper (I) cyanide in N,N-dimethylformamide. $R^{1a}$ or $R^{1b}$ carboxy may be obtained by conventional hydrolysis of $R^{1a}$ or $R^{1b}$ cyano, and the carboxy converted to hydroxymethyl by conventional reduction.

Compounds of formula HA-N($R^{20}$)$R^{2'}$, (1) and (7) are known compounds or may be prepared analogously to known compounds, see for example WO2004/035569, WO2004/089947, WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO2003082835, WO2002026723, WO06002047 and WO06014580.

As shown in Scheme 3, the hydroxy-aminomethylpyrrolidines of formula (XIII) (HA-NH($R^{20}$), A is (ii), X is $CR^4R^8$, $W^1$ is a bond, $W^2$ and $W^3$ are both $CH_2$, $R^4$ and $R^7$ are H and $R^8$ is OH) can be prepared from doubly protected chiral intermediate (XVI), and separated by preparative HPLC. The benzyloxycarbonyl, protecting group is removed by hydrogenation to give (XV) and the amino function converted to a trifluoroacetamide (XIV). The t-butoxycarbonyl (Boc) protecting group is removed with HCl to give the pyrrolidine hydrochloride salt (III).

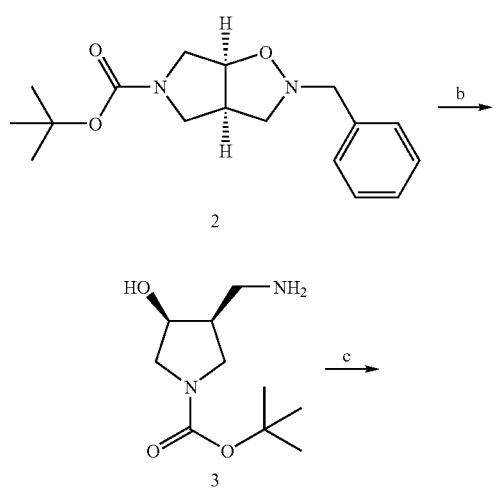

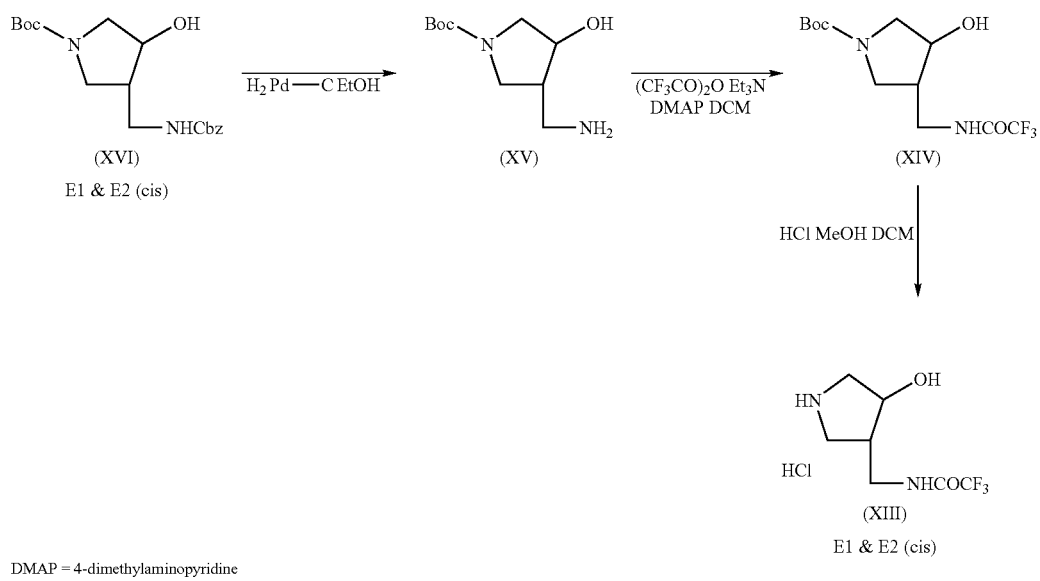

DMAP = 4-dimethylaminopyridine

The intermediate (XVI) may be prepared by the general method of Scheme 4:

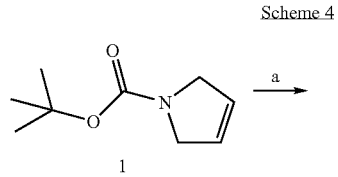

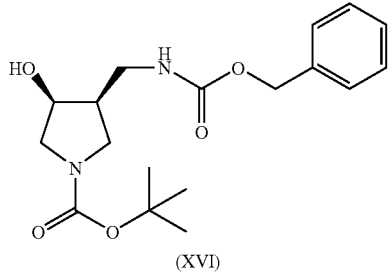

Reagents and conditions: (a) N-Hydroxybenzylamine hydrochloride, paraformaldehyde, toluene, EtOH, 80° C.; (b)

Pd(OH)$_2$, H$_2$ (50 psi), MeOH, room temperature; (c) Benzyloxycarbonyl-succinimide, Et$_3$N, dichloromethane, room temperature.

In Scheme 5 the aminomethylpyrrolidine of formula (XVII) (HA-NH(R$^{20}$), A is (ii), X is CR$^4$R$^8$, W$^1$ is a bond, W$^2$ and W$^3$ are both CH$_2$, R$^4$, R$^7$ and R$^8$ are all H) can be prepared from commercially available Boc-protected aminomethylpyrrolidine, and converted to the trifluoroacetamide.

The aminomethylmorpholine intermediate of formula (XXI) (HA-NH(R$^{20}$), A is (ii), X is O, W$^1$, W$^2$ and W$^3$ are each CH$_2$) may be prepared from a chiral dichlorobenzyl intermediate (XXIII) (WO2003082835) (Scheme 6) by first protecting the amino function with a Boc-protecting group (XXII), removing the dichlorobenzyl group by hydrogenation to give (XXI), protecting the morpholine N-atom with a benzyloxycarbonyl group (to allow purification by chromatography) (XX), and hydrogenation to afford the required morpholine derivative (XXI).

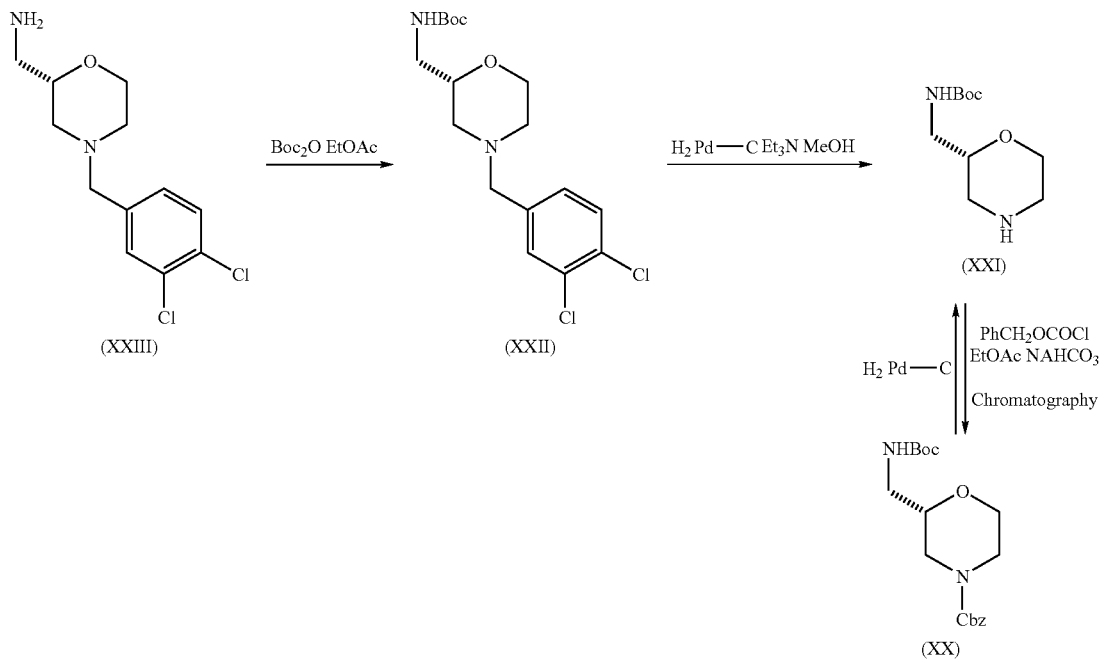

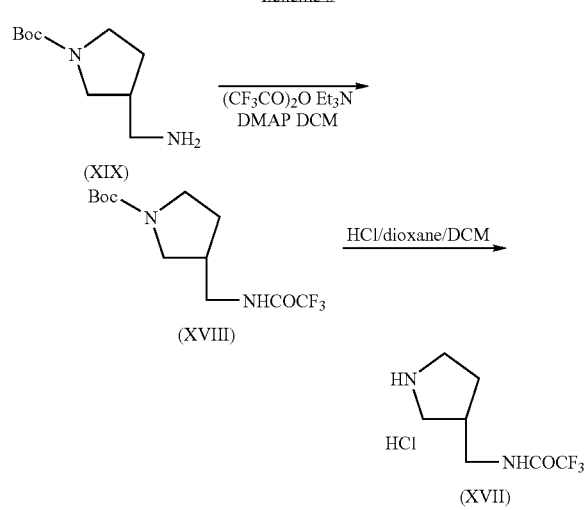

Further details for the preparation of compounds of formula (I) are found in the examples.

The antibacterial compounds according to the invention may be formulated for administration in any convenient way for use in human or veterinary medicine, by analogy with other antibacterials.

The pharmaceutical compositions of the invention include those in a form adapted for oral, topical or parenteral use and may be used for the treatment of bacterial infection in mammals including humans.

The composition may be formulated for administration by any route. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-1000 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 30 mg/kg per day.

The compound of formula (I) may be the sole therapeutic agent in the compositions of the invention or a combination with other antibacterials. If the other antibacterial is a β-lactam then a β-lactamase inhibitor may also be employed.

Compounds of formula (I) may be used in the treatment of bacterial infections caused by a wide range of organisms including both Gram-negative and Gram-positive organisms.

Some compounds of formula (I) may be active against more than one organism. This may be determined by the methods described herein.

All publications, including but not limited to patents and patent applications, cited in this specification are herein incorporated by reference as if each individual publication were specifically and individually indicated to be incorporated by reference herein as though fully set forth.

The following examples illustrate the preparation of certain compounds of formula (I) and the activity of certain compounds of formula (I) against various bacterial organisms.

EXAMPLES AND EXPERIMENTAL

General

Abbreviations in the Examples:
MS=mass spectrum
ES=Electrospray mass spectroscopy
LCMS or LC-MS=Liquid chromatography mass spectroscopy
HPLC=High Performance Liquid Chromatography (Rt refers to retention time)

Certain reagents are also abbreviated herein. DMF refers to N,N-dimethylformamide, TFA refers to trifluoroacetic acid, THF refers to tetrahydrofuran, Pd/C refers to palladium on carbon catalyst, DCM refers to dichloromethane.

Proton nuclear magnetic resonance ($^1$H NMR) spectra were recorded at 400 or 250 Mhz, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. $CDCl_3$ is deuteriochloroform. Mass spectra were obtained using electrospray (ES) ionization techniques. All temperatures are reported in degrees Celsius. MP-carbonate refers to macroporous triethylammonium methylpolystyrene carbonate (Argonaut Technologies). Chiralpak AD and AD-H columns comprise of silica for preparative columns (5 um particle size AD-H, 21×250 mm; 20 uM particle size AD, 101.6×250 mm) coated with Amylose tris (3,5-dimethylphenylcarbamate) (Chiral Technologies USA). Chiralcel OD column comprises of silica for a preparative column (20 um particle size; 77×240 mm) coated with cellulose tris (3,5-dimethylphenylcarbamate). Measured retention times are dependent on the precise conditions of the chromatographic procedures. Where quoted below in the Examples they are indicative of the order of elution.

AD mix alpha is prepared by mixing potassium osmate ($K_2OsO_4.2H_2O$) (0.52 g), (3a,9R,3'''a,4'''b,9'''R)-9,9'-[1,4-phthalazinediylbis(oxy)]bis[6'-(methyloxy)-10,11-dihydrocinchonan][$(DHQ)_2PHAL$] (5.52 g), then adding potassium ferricyanide [$K_3Fe(CN)_6$] (700 g) and powdered potassium carbonate (294 g). This mixture is stirred in a blender for 30 minutes. This provides approximately 1 kg of AD mix alpha, which is commercially available from Aldrich. See K. Barry Sharpless et al, J. Org. Chem., 1992, 57 (10), 2771. AD mix beta is the corresponding mixture prepared with (9S,9'''S)-9,9'-[1,4-phthalazinediylbis(oxy)]bis[6'-(methyloxy)-10,11-dihydrocinchonan][$(DHQD)_2PHAL$].

Where AD mix alpha/beta is referred to, this is a 1:1 mixture of the alpha and beta mix.

Celite® is a filter aid composed of acid-washed diatomaceous silica, and is a trademark of Manville Corp., Denver, Colo.

Chiralcel OD is a polysaccharide based chiral HPLC column (Chiral Technologies Inc.).

Reactions involving metal hydrides including lithium hydride, lithium aluminium hydride, di-isobutylaluminium hydride, sodium hydride, sodium borohydride and sodium triacetoxyborohydride are carried out under argon.

Extraction steps may if desired be carried out with ethyl acetate in place of the specified solvents.

Differential Scanning Calorimetry (DSC)
DSC is conducted on a TA Instrument model Q100 Differential Scanning Calorimeter. The sample is placed and weighed in a Al DSC pan. The pan is sealed using the hand press supplied by the vendor. The sample is ramped from 35° C. to 300° C. at 15° C./minute.

X-Ray Powder Diffraction (XRPD):
PXRD General Area Detector Diffraction System.
The sample is scanned using the following parameters:
  Scan range: 2-56 degrees two-theta
  Generator power: 40 kV, 40 mA
  Radiation Source Cu Ka
  Scan type: Coupled scan
  Number of frames: 4 frames
  Time per frame: 5 min
  Sample Oscillation: 0.1-0.5 mm oscillation depending on sample size
  Detector Distance: 25 cm
  Filter/monochrometer: Single Goebel Mirror
  Detector Type General Area Detector Diffraction As will be understood by the skilled chemist, references to preparations carried out in a similar manner to, or by the general method of, other preparations, may encompass variations in routine parameters such as time, temperature, workup conditions, minor changes in reagent amounts etc.

Example 1

(4S)-4-({4-[(2,3-Dihydro[1,4]dioxino[2,3-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one (E1 enantiomer series) hydrochloride

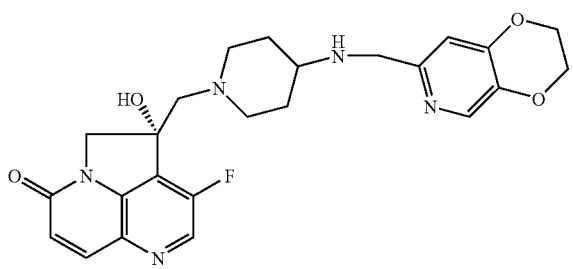

(a) Pyridine-tris(1-methylethenyl)boroxin (1:1)

A suspension of magnesium turnings (20.83 g, 868 mmol) in THF (1.2 litres) under argon at room temperature was treated with 2-bromopropene (20 ml) and the reaction initiated with a little heat. Upon initiation, external heating was stopped and the reaction mixture maintained at around 50-60° C. by the addition of more 2-bromopropene in three portions (53 ml) over a period of around 1.5 h. The mixture, containing isopropenylmagnesium bromide, was allowed to cool to ambient temperature. The remainder of the procedure followed that as described for the corresponding pyridine-tris (triethenyl)boroxin (1:1) (J. Org. Chem. 2002, 67, 4968). The solution of isopropenylinagnesium bromide (approximately 826 mmol in 1.2 litres of THF) and an additional batch of isopropenylmagnesium bromide 250 mmol in 500 ml of THF (commercial material) was added to a solution of trimethyl borate (217 ml, 1937 mmol) in 1 litre THF cooled to −78° C. under argon. After the addition was complete (approximately 1 hour) the mixture was maintained at −78° C. for 1 hour before the addition of 1M HCl (550 ml) over 5 min. The mixture was allowed to warm to ambient temperature, then brine (500 ml) and diethyl ether (500 ml) were added. The aqueous phase was further extracted with diethyl ether (3×500 ml) and the combined organic extracts were washed with water (500 ml), brine (500 ml), dried (sodium sulphate) and evaporated to a volume of approximately ⅛. Pyridine (220 ml) was added and the mixture stirred for a period of 4 hours. Evaporation afforded an oil (86.4 g, 83%).

δH (CDCl$_3$, 400 MHz) 1.80 (9H, s), 5.45 (3H, s), 5.65 (3H, s), 7.62 (2H, t), 8.02 (1H, m), 8.85 (2H, d).

Catalytic iodine may be used to initiate the reaction of 2-bromopropene with magnesium. Excess boric acid and derivatives thereof may be removed from the reaction mixture by filtration through Celite® before addition of pyridine.

(b) 7-Fluoro-8-(1-methylethenyl)-2-(methyloxy)-1,5-naphthyridine

Method A
A solution of 8-bromo-7-fluoro-2-(methoxy)-1,5-naphthyridine (8.53 g, 33.2 mmol) (for a synthesis, see WO2004058144, Example 53(g)) and tetrakis(triphenylphosphine)palladium(0) (1.92 g, 1.7 mmol) in degassed dimethoxyethane (300 ml) was stirred under argon for 30 minutes. Potassium carbonate (4.58 g, 33.2 mmol), water (90 ml) and pyridine-tris(1-methylethenyl)boroxin (1:1) (3.8 g, 13.3 mmol) were added and the mixture was heated to reflux for 10 hours. The mixture was allowed to cool and treated with water (500 ml) and diethyl ether (500 ml). The phases were separated and the aqueous phase further extracted with diethyl ether (3×500 ml). The combined organic extracts were dried over magnesium sulphate and evaporated. The residue was chromatographed on silica eluting with a gradient of 0-50% ethyl acetate in hexane affording a yellow oil (6.9 g, 95%).

MS (+ve ion electrospray) m/z 219 (MH+).

Method B
To a flask were charged THF (50 ml) and magnesium turnings (1.9 g, 2 eq) excluding air. The mixture was stirred at room temperature for 30-60 minutes. A first 10-20% portion of 2-bromopropene (6.9 ml, 9.4 g, 1.3 eq in all) in THF (20 mL) was added. A catalytic amount of iodine and heating to 40° C. were employed to initiate Grignard reaction then allowed to naturally cool. A temperature rise was observed when Grignard reaction initiated. The remaining 2-bromopropene was added in while maintaining temperature below 62° C. The resulting mixture after addition was at ~50° C. and was heated at ~47° C. to ensure the reaction was complete.

To a separate flask was charged THF (20 ml). Solid zinc chloride (20 g, 2.5 eq) was added in one portion and a temperature rise was observed. The mixture was cooled down to ~−10° C.

The above freshly prepared Grignard reagent (in THF) was transferred into the ZnCl$_2$ mixture slowly at a rate maintaining temperature below 25° C. The resulting mixture was warmed up to room temperature, a further 20 ml THF was added and stirred at room temperature for 2 hours.

To the above reaction mixture were added tetrakis(triphenylphosphine)palladium(0) [Pd(PPh3)4, 1.3 g, 2% mol] as a solid in one portion and 8-bromo-7-fluoro-2-(methoxy)-1,5-naphthyridine (15.0 g, 1 eq) as a solid in one portion. No heat was observed. The reaction mixture was heated at reflux until reaction complete monitoring with HPLC.

The reaction was cooled down to ~10° C. and quenched with 100 ml of 10% citric acid aqueous solution (exothermic). Ethyl acetate (100 ml) was added for extraction. The organic layer was washed with 100 ml water and the aqueous layer was extracted with 100 ml ethyl acetate. The combined organic solution was concentrated to dryness to afford a dark oil and further purified by a silica column with heptane/ethyl acetate (1/0, 3/1, 2/1) as the eluent (11.8 g, ~93% yield and ~97% purity per area ratio by HPLC).

Zinc bromide may be substituted for zinc chloride, and the concentration of the palladium catalyst may be reduced to 0.5%. The washing step may be performed with 4% citric acid aqueous solution instead of water.

(c) 8-[1-(Chloromethyl)ethenyl]-7-fluoro-2-(methyloxy)-1,5-naphthyridine

Method A

A solution of 7-fluoro-8-(1-methylethenyl)-2-(methyloxy)-1,5-naphthyridine (7.3 g, 33.5 mmol) in tert-butanol (500 ml) under argon was treated with cerium(III) chloride heptahydrate (12.5 g, 33.5 mmol) followed by a dropwise solution of sodium hypochlorite (12% w/v, 21.1 ml, 33.5 mmol). A yellow suspension was formed. After 15 minutes more sodium hypochlorite (12% w/v, 21.1 ml, 33.5 mmol) was added. After 10 minutes stirring, saturated aqueous sodium sulphite solution (200 ml) was added. After 5 minutes stirring water (500 ml) was added and the mixture extracted with ether (3×500 ml). The combined organic extracts were dried over magnesium sulphate and evaporated. The residue was chromatographed on silica eluting with a gradient of 0-50% ethyl acetate in hexane affording product (4.9 g, 58%).

The organic extracts may be dried by washing with brine and ethyl acetate instead of drying over magnesium sulphate.

Method B

A solution of 7-fluoro-8-(1-methylethenyl)-2-(methyloxy)-1,5-naphthyridine (31.86 g, 146 mmol) in tert-butanol (2 L) was treated with cerium(III) chloride heptahydrate (54.4 g, 146 mmol), stirred for 15 minutes then treated with a solution of sodium hypochlorite (12% w/v, 139 ml, 221 mmol) added over 15 minutes. After 15 minutes stirring saturated aqueous sodium sulphite solution (800 ml) was added. After 30 minutes stirring more water was added and the mixture extracted with diethyl ether (1×500 ml, 2×2 L). The combined organic extracts were dried and evaporated. The residue was chromatographed on silica eluting a gradient of 0-100% dichloromethane in hexane affording product (17.5 g, 48%).

MS (+ve ion electrospray) m/z 253 (MH+).

(d) 3-Fluoro-4-methylidene-4,5-dihydro-7H-pyrrolo[3,2,1-de]-1,5-naphthyridin-7-one A mixture of 8-[1-(chloromethyl)ethenyl]-7-fluoro-2-(methyloxy)-1,5-naphthyridine (4.9 g, 19.5 mmol) and sodium iodide (29 g, 195 mmol) in acetone (100 ml) was heated to reflux for 18 hours. The mixture was evaporated and the residue partitioned between water (200 ml) and dichloromethane (200 ml). The aqueous phase was further extracted with dichloromethane (2×200 ml) and the combined dichloromethane extracts washed with water (2×200 ml) dried over magnesium sulphate and evaporated. The resulting solid was triturated with ethyl acetate (50 ml) and filtered and washed with ethyl acetate (20 ml) affording a brown solid. This material was then dissolved in ethyl acetate and filtered through a plug of silica. Evaporation afforded a solid (1.4 g, 36%).

MS (+ve ion electrospray) m/z 203 (MH+).

If necessary the product may be taken up in n-hexane and precipitated out and the solid purified by stirring with cold acetone.

(e) 3-Fluoro-4-hydroxy-4-(hydroxymethyl)-4,5-dihydro-7H-pyrrolo[3,2,1-de]-1,5-naphthyridin-7-one Method A A mixture of 3-fluoro-4-methylidene-4,5-dihydro-7H-pyrrolo[3,2,1-de]-1,5-naphthyridin-7-one (37.1 g, 183 mmol), tert-butanol (1.5 litres), water (1.5 litres) and AD mix alpha (Aldrich) (246 g) was stirred vigorously for 16 hours at room temperature. Sodium sulphite (300 g) was added and the mixture was stirred for 30 minutes. The phases were separated and the aqueous phase was extracted three times with 10% methanol in ethyl acetate (total volume 1 litre). The combined organic extracts were dried and evaporated affording a solid (45 g, 100%).

MS (+ve ion electrospray) m/z 237 (MH+).

Method B

To a 1 L 3-neck flask was added potassium hexacyanoferrate (III) (24.50 g), potassium carbonate (granular, 10.25 g), potassium osmate (VI) dihydrate (25 mg), and water (125 mL). This mixture was stirred at room temperature for 10 min, to which was added a predissolved solution of hydroquinine anthraquinone-1,4-diyl diether ((DHQ)$_2$AQN) (200 mg) in 2-butanol (125 mL). The resulting mixture was stirred for 15 min, to which was added 3-fluoro-4-methylidene-4,5-dihydro-7H-pyrrolo[3,2,1-de]-1,5-naphthyridin-7-one (4.60 g). The resulting mixture was stirred at ambient temperature for 18 h. To the mixture was added Na$_2$SO$_3$ (37.25 g), and stirred for 30 min at room temperature. To this mixture was added water (100 mL) and methanol (10 mL), extracted with 3×250 mL of ethyl acetate. The combined ethyl acetate fractions were washed with brine, dried over Na$_2$SO$_4$, filtered, and concentrated in vacuo to give title compound as a gum. Chiral HPLC indicated the ratio of 4R/4S to be 13.3/86.7.

t-Butanol may be used in place of 2-butanol in the above reaction with (DHQ)$_2$AQN and also for the extraction step in place of ethyl acetate. If necessary the product may be dissolved in warm toluene and cooled to precipitate the product as a solid.

(f) 1,1-Dimethylethyl {1-[(3-fluoro-4-hydroxy-7-oxo-4,5-dihydro-7H-pyrrolo[3,2,1-de]-1,5-naphthyridin-4-yl)methyl]-4-piperidinyl}carbamate Method A A solution of 3-fluoro-4-hydroxy-4-(hydroxymethyl)-4,5-dihydro-7H-pyrrolo[3,2,1-de]-1,5-naphthyridin-7-one (25.09 g, 106.3 mmol) in dichloromethane (1 litre), THF (1 litre) and N,N-dimethylformamide (100 ml) was treated with triethylamine (22.7 ml, 159 mmol), para-toluenesulphonyl chloride (20.2 g, 106.3 mmol) and dibutyltin oxide (1.32 g, 5.23 mmol). After 16 hours stirring at room temperature, water (400 ml) was added, then the organic phase was separated, washed with aqueous sodium bicarbonate and brine, dried and evaporated to give crude toluenesulphonate (approximately 3:1 4S:4R) containing some corresponding epoxide and DMF (43.8 g). This material was dissolved in ethanol (1.1 litres) and treated with sodium carbonate (33.4 g) and 1,1-dimethylethyl 4-piperidinylcarbamate (28.3 g, 142 mmol). The mixture was stirred over the weekend then evaporated almost to dryness. The residue was partitioned between water and 5% methanol in dichloromethane. The phases were separated and the aqueous phase was further extracted with two portions of 5% methanol in dichloromethane. The combined organic extracts were dried and evaporated. The residue was chromatographed on silica (2 kg) eluting with 2-5% methanol/dichloromethane affording the product (39.94 g, 90%).

MS (+ve ion electrospray) m/z 419 (MH+).

Method B

3-Fluoro-4-hydroxy-4-(hydroxymethyl)-4,5-dihydro-7H-pyrrolo[3,2,1-de]-1,5-naphthyridin-7-one (3.65 g total, 1.32 g with enantiomeric ratio 4R/4S: 15.7/84.3 and 2.33 g with enantiomeric ratio 4R/4S: 17/83), toluenesulfonyl chloride (2.94 g), dibutyltin (IV) oxide (192 mg), tetrahydrofuran (anhydrous, 146 mL), dichloromethane (anhydrous, 146 mL), triethylamine (3.31 mL) and N,N-dimethylformamide (anhydrous, 14.6 mL) was stirred at room temperature as a suspension for 18 h. The mixture was washed with water, saturated aq. NaHCO₃ and brine, dried over Na₂SO₄, filtered and concentrated in vacuo to give the corresponding toluenesulfonate.

A mixture of the above toluenesulfonate, 1,1-dimethylethyl-4-piperidinylcarbamate (4.13 g), Na₂CO₃ (4.87 g) in ethanol (160 mL) was stirred as a suspension at room temperature for 2.5 days. This mixture was combined with another batch prepared analogously from 1.50 g of 3-fluoro-4-hydroxy-4-(hydroxymethyl)-4,5-dihydro-7H-pyrrolo[3,2,1-de]-1,5-naphthyridin-7-one with enantiomeric ratio 4R/4S: 17/83. The resulting mixture was filtered and the Na₂CO₃ cake was washed with ethanol. The filtrate was concentrated in vacuo and taken up in 300 mL of 5% methanol in dichloromethane. The resulting solution was washed with saturated aq. NaHCO₃ (30 mL), dried over Na₂SO₄, filtered and concentrated in vacuo to give a gum. Trituration in dichloromethane gave 1.27 g of the title compound (14% yield, enantiomeric ratio 4R/4S: 15/85). The filtrate was purified by silica gel column chromatography, resulting in 2.00 g of the title compound (22% yield, enantiomeric ratio 4R/4S: 52/48). The Na₂CO₃ cake mentioned above was taken up in water, extracted with 5% methanol in dichloromethane, providing 3.85 g of title compound (42% yield, enantiomeric ratio: 0/100).

2.0 g of title compound (enantiomeric ratio 4R/4S: 15/85) was dissolved in 45 mL of hot ethanol. The solution was aged at room temperature for 1.5 days, chilled at 0° C. for 5 h, −20° C. for 1 day and filtered to give 1.12 g of material that has a measured enantiomeric ratio 4R/4S of 0/100.

1.050 g of title compound with an enantiomeric ratio 4R/4S of 15/85 and 400 mg with an enantiomeric ratio 4R/4S of 52/48 (the measured enantiomeric ratio 4R/4S of this resulting mixture was 24/76) was dissolved in 40 mL of hot ethanol. The solution was cooled gradually to room temperature, aged at ambient temperature for 2.5 days, chilled at 0° C. for 15 min, filtered, and washed with 3×1.5 mL of cold ethanol and dried, resulting in 580 mg of title compound with a measured enantiomeric ratio 4R/4S of 0/100. The filtrate had a measured enantiomeric ratio 4R/4S of 48/52.

Both the reaction with p-toluensulphonyl chloride and the reaction with 1,1-dimethylethyl 4-piperidinylcarbamate may be carried out in dichloromethane. Potassium carbonate may be used in place of sodium carbonate in the reaction with 1,1-dimethylethyl 4-piperidinylcarbamate. If necessary triethylamine may be added in this reaction to promote completion.

A purification protocol for preparing title compound of high enantiomeric purity (4S) from crude product is as follows:

1. Add methanol followed by water to reaction mass and stir for 5-10 min.
2. Separate the organic layer.
3. Extract aqueous layer with 10% methanol in DCM.
4. Combine organic layers and wash with brine solution.
5. Remove solvent under reduced pressure at 25-35° C. to less than $1/10^{th}$ of its volume.
6. Add 10% ethyl acetate in n-hexane to the residue.
7. Stir at room temperature for 10-12 h.
8. Filter the solid and dry the solid at 50-60° C. under vacuum for 6-8 h.
9. Charge stage 8 and acetonitrile.
10. Stir the reaction mass at 60-70° C. for 1-2 h.
11. Stir the reaction mass at room temperature for 10-12 h.
12. Raise temp to 50-60° C. and stir for 2-3 h or until the solid from a filtered sample shows undesired isomer: <1.0% by analytical chiral hplc.
13. Filter the isolated solid at 50-60° C. and wash the solid with acetonitrile.
14. Suck dry the solid for 30-45 min.
15. Dry the material in the oven at 50-60° C. under vacuum.

The resulting (4S)-1,1-Dimethylethyl {1-[(3-fluoro-4-hydroxy-7-oxo-4,5-dihydro-7H-pyrrolo[3,2,1-de]-1,5-naphthyridin-4-yl)methyl]-4-piperidinyl}carbamate may be used in stage (g) below, obviating the need for the chiral chromatography step (g) 4-[(4-Amino-1-piperidinyl)methyl]-3-fluoro-4-hydroxy-4,5-dihydro-7H-pyrrolo[3,2,1-de]-1,5-naphthyridin-7-one A solution of 1,1-dimethylethyl {1-[(3-fluoro-4-hydroxy-7-oxo-4,5-dihydro-7H-pyrrolo[3,2,1-de]-1,5-naphthyridin-4-yl)methyl]-4-piperidinyl}carbamate (47.94 g, 115 mmol) in dichloromethane/methanol (870 ml/610 ml) was cooled in an ice bath and treated with a solution of hydrochloric acid in 1,4-dioxane (4M, 1.5 litres). The resulting mixture was stirred at room temperature for 1.5 hours then partially evaporated. Filtration, washing with a little dichloromethane and drying in vacuo afforded the hydrochloride of the title compound as a solid (51.55 g). Title compound hydrochloride (50.5 g) was dissolved in water (500 ml) and treated with saturated aqueous sodium carbonate solution until pH8 was obtained (ca 100 ml). The mixture was evaporated to dryness and the resulting solid extracted with 15% methanol in chloroform (3×500 ml). The extracts were evaporated separately affording 22 g, 10 g, and 4 g of solid materials which were essentially identical by spectroscopic analysis.

Title compound (96.5 g) was chromatographed on a Chiralpak AD column eluting with acetonitrile:isopropyl alcohol:isopropylamine 80:20:0.1 affording firstly the E1 enantiomer (4S)-4-[(4-amino-1-piperidinyl)methyl]-3-fluoro-4-hydroxy-4,5-dihydro-7H-pyrrolo[3,2,1-de]-1,5-naphthyridin-7-one (66.1 g) then the E2 enantiomer (4R)-4-

[(4-amino-1-piperidinyl)methyl]-3-fluoro-4-hydroxy-4,5-dihydro-7H-pyrrolo[3,2,1-de]-1,5-naphthyridin-7-one (24.4 g).

MS (+ve ion electrospray) m/z 319 (MH+).

This reaction may alternatively be performed using c.HCl in dichloromethane as solvent. The product as the hydrochloride salt may be precipitated from acetone and used directly in stage (h) below after neutralisation using anhydrous sodium acetate.

(h) Title Compound

Method A

A solution of 4-[(4-amino-1-piperidinyl)methyl]-3-fluoro-4-hydroxy-4,5-dihydro-7H-pyrrolo[3,2,1-de]-1,5-naphthyridin-7-one (5.7 g, 18 mmol) and 2,3-dihydro[1,4]dioxino[2,3-c]pyridine-7-carboxaldehyde (for a synthesis see WO2004058144, Example 2(c) or WO03/087098, Example 19(d)) (3.0 g, 18 mmol) in dichloromethane/methanol (75 ml/7 ml) was cooled in an ice bath under argon, stirred and treated with sodium triacetoxyborohydride (7.6 g, 35.9 mmol). More dichloromethane/methanol (50 ml/5 ml) was added and the mixture stirred at 0° C. for 1 hour. Saturated aqueous sodium bicarbonate solution (150 ml) and then brine (100 ml) were added. The resulting mixture was extracted with 10% methanol/dichloromethane (2×100 ml) then 20% methanol/dichloromethane (100 ml). The organic extracts were dried over magnesium sulphate and evaporated to give a yellow foam (7.6 g). This was chromatographed on silica eluting with 0-25% 2M ammonia in methanol/ethyl acetate affording the free base of the title compound (approx 3:1 4S:4R) (6.8 g, 81%).

Method B

A solution of (4S)-4-[(4-amino-1-piperidinyl)methyl]-3-fluoro-4-hydroxy-4,5-dihydro-7H-pyrrolo[3,2,1-de]-1,5-naphthyridin-7-one (E1 enantiomer) (1.0 g, 3.14 mmol) and 2,3-dihydro[1,4]dioxino[2,3-c]pyridine-7-carboxaldehyde (for a synthesis see WO2004058144, Example 2(c) or WO03/087098, Example 19(d)) (0.52 g, 3.14 mmol) in dichloromethane/methanol (13 ml/1 ml) under argon was treated at 0° C. with sodium triacetoxyborohydride (1.33 g, 6.29 mmol). The reaction was then allowed to warm to room temperature and stirred at room temperature for 2.5 h. Saturated aqueous sodium bicarbonate solution (20 ml) and then brine (25 ml) were added. The resulting mixture was extracted with 10% methanol/dichloromethane (3×20 ml) then 20% methanol/dichloromethane (15 ml) then 10% methanol/dichloromethane (20 ml). The organic extracts were dried with magnesium sulphate and evaporated to give a yellow solid/oil (1.42 g). This was chromatographed on silica eluting with 0-10% 2M ammonia in methanol/dichloromethane affording the free base of the title compound (0.969 g, 66%).

The reductive alkylation reaction may also be conducted in DMF instead of DCM/methanol. Molecular sieves may be included in the reaction mass.

The extraction may be carried out with 10% methanol in chloroform and the product may be purified by precipitation from acetone instead of chromatography on silica.

NMR of title compound, free base

δH (CDCl$_3$, 400 MHz) 1.35-1.55 (2H, m), 1.85-1.95 (2H, m), 2.37 (1H, t), 2.45-2.60 (2H, m), 2.85-2.92 (2H, m), 2.95-3.02 (1H, d), 3.20 (1H, d), 3.75 (2H, s), 4.25-4.29 (2H, m), 4.32-4.35 (2H, m), 4.38-4.42 (2H, m), 6.75-6.80 (2H, m), 7.88 (1H, d), 8.05 (1H, s), 8.35 (1H, s).

MS (+ve ion electrospray) m/z 468 (MH+).

To amorphous free base of the title compound (361.0 mg), tetrahydrofuran (1.5 mL) was added. The input material dissolved completely in the solvent. The solution was left undisturbed and within a few minutes, crystals started to appear. The slurry was left undisturbed overnight and the solid was analysed using polarised light microscopy which showed the presence of crystalline material. The solid was filtered, washed with tetrahydrofuran and dried in a vacuum oven overnight at 50 C with a slight flow of nitrogen. The weight of the crystalline free base material obtained was about 271.9 mg.

Melting Onset: 184.7° C. (measured by DSC).

XRPD peaks (values given in degrees two-theta): 9.5±0.2 (2θ), 12.5±0.2 (2θ), 13.2±0.2 (2θ), 14.7±0.2 (2θ), 17.6±0.2 (2θ), 19.7±0.2 (2θ).

A solution of (4S)-4-({4-[(2,3-dihydro[1,4]dioxino[2,3-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one (E1 enantiomer series) (25 mg, 0.05 mmol) was treated with an excess of hydrochloric acid in ether affording the dihydrochloride salt (21 mg).

MS (+ve ion electrospray) m/z 468 (MH+).

Acetonitrile (500 μL) was added to crystalline free base of the title compound (10.1 mg). To the slurry, fumaric acid (1.0 equivalent, 0.2 M solution in ethanol) was added. The slurry in the HPLC vial was shaken for 48 hours at room temperature (24° C.). The solids were then filtered and dried in a vacuum oven at 50° C. overnight to afford fumarate salt.

Melting Onset: 140.6° C. (measured by DSC).

A solution of (4S)-4-({4-[(2,3-dihydro[1,4]dioxino[2,3-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one (E1 enantiomer series) (919 mg) in dichloromethane (25 ml) was treated with hydrochloric acid in ether (1M, 2.4 ml, 2.4 mmol) affording the title hydrochloride salt as a solid (1.0 g).

MS (+ve ion electrospray) m/z 468 (MH+).

(4S)-4-({4-[(2,3-dihydro[1,4]dioxino[2,3-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one (E1 enantiomer series) (48 g) was dissolved in 500 ml of refluxing methanol. The solution was cooled to 50° C. and HCl 6N (17.1 ml, 1 equivalent) was added in one portion. The solution was further cooled to 30° C. and concentrated under reduced pressure at 50° C. The resulting yellow solid was dried for 18 hours under high vacuum at 50° C. to afford 54 g of title hydrochloride salt.

The title hydrochloride salt may alternatively be prepared by treatment of the free base with pyridine hydrochloride in methanol and the product precipitated out by slowly adding the solution to acetone.

The stereochemistry of the title compound (recrystallised by slow evaporation from a solution in methanol and toluene to give monoclinic needles) was determined from 3-dimensional X-ray diffraction data to be 4S.

Acetone (3000 μL) was added to amorphous free base (367.0 mg). The resulting solution was stirred at room temperature for 30 mins and then hydrochloric acid (1M solution in 1,4-dioxane, 1.0 equivalent) was added. The slurry was stirred overnight at room temperature. The solid was filtered, washed with acetone and dried in a vacuum oven at 50° C. with a slow flow of nitrogen. The yield of title crystalline HCl salt was 87.5% (346.7 mg).

Melting Onset: 215.6° C. (measured by DSC).

XRPD peaks (values given in degrees two-theta): 5.3±0.2 (2θ), 9.2±0.2 (2θ), 13.4±0.2 (2θ), 13.9±0.2 (2θ), 14.9±0.2 (2θ), 16.0±0.2 (2θ), 16.6±0.2 (2θ).

1,4 Dioxane: 10 vol % Water (500 uL) was added to title crystalline HCl salt (~30 mg). The resulting slurry was, under a vortex speed of 750 rpm, held at 40° C. for 1 h then was temperature-cycled from 0-40° C. for ~48 hours (ramp at −1° C./min to 0° C., hold for 1 h, +1° C./min to 40° C., hold for 1 h). Finally the product was ramped at −1° C./min to 23° C. and held for 1 h at a vortex speed of 500 rpm. The resulting solids and supernatant were separated by filtration at room temperature. The solid were vacuum dried under ambient laboratory conditions.

Melt/decomposition onset at approximately 229° C. (measured by DSC).

Example 1B (4R/S)-4-({4-[(2,3-Dihydro[1,4]dioxino[2,3-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one dihydrochloride

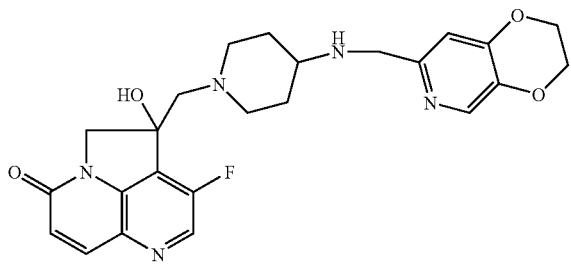

(a) [(4R/S)-3-Fluoro-4-hydroxy-7-oxo-4,5-dihydro-7H-pyrrolo[3,2,1-de]-1,5-naphthyridin-4-yl]methyl 4-methylbenzenesulfonate A mixture of (4R/S)-3-fluoro-4-hydroxy-4-(hydroxymethyl)-4,5-dihydro-7H-pyrrolo[3,2,1-de]-1,5-naphthyridin-7-one (553 mg, 2.3 mmol) (racemic material, prepared from 3-fluoro-4-methylidene-4,5-dihydro-7H-pyrrolo[3,2,1-de]-1,5-naphthyridin-7-one using AD mix alpha/beta in a similar manner to Example 1(e) Method A) in dichloromethane/tetrahydrofuran/N,N-dimethylformamide (19 ml19 ml/2 ml) was treated with triethylamine (0.5 ml, 3.5 mmol), paratoluenesulphonyl chloride (446 mg, 2.3 mmol) and dibutyltin oxide (29 mg, 0.1 mmol) and stirred at room temperature overnight. Water was then added, the organic phase was separated and washed with saturated aqueous sodium bicarbonate, separated, dried over magnesium sulphate and evaporated under vacuum. The residue was chromatographed on silica eluting with 0-100% ethyl acetate in dichloromethane then 0-10% methanol in ethyl acetate affording a white solid (321 mg, 35%).

MS (+ve ion electrospray) m/z 391 (MH+).

(b) 1,1-Dimethylethyl (2,3-dihydro[1,4]dioxino[2,3-c]pyridin-7-ylmethyl)(1-{[(4R/S)-3-fluoro-4-hydroxy-7-oxo-4,5-dihydro-7H-pyrrolo[3,2,1-de]-1,5-naphthyridin-4-yl]methyl}-4-piperidinyl)carbamate A mixture of [(4R/S)-3-fluoro-4-hydroxy-7-oxo-4,5-dihydro-7H-pyrrolo[3,2,1-de]-1,5-naphthyridin-4-yl]methyl 4-methylbenzenesulfonate (100 mg, 0.25 mmol), 1,1-dimethylethyl (2,3-dihydro[1,4]dioxino[2,3-c]pyridin-7-ylmethyl)-4-piperidinylcarbamate (84 mg, 0.24 mmol) (for a synthesis, see WO2004058144, Example 99(h)), sodium carbonate (77 mg, 0.7 mmol) and ethanol (2.5 ml) was stirred at room temperature overnight then evaporated under vacuum. The residue was treated with water and the mixture extracted twice with dichloromethane. The combined organic extracts were dried over magnesium sulphate and evaporated under vacuum. The residue was chromatographed on silica eluting with 0-100% ethyl acetate in dichloromethane then 0-10% methanol in ethyl acetate affording a yellow oil (88 mg, 64%).

MS (+ve ion electrospray) m/z 568 (MH+).

(c) Title Compound

A solution of 1,1-dimethylethyl (2,3-dihydro[1,4]dioxino[2,3-c]pyridin-7-ylmethyl)(1-{[(4R/S)-3-fluoro-4-hydroxy-7-oxo-4,5-dihydro-7H-pyrrolo[3,2,1-de]1,5-naphthyridin-4-yl]methyl}-4-piperidinyl)carbamate (88 mg, 0.15 mmol) in dichloromethane (1.5 ml) was treated with trifluoroacetic acid (1.5 ml). After 1 hour under stirring the mixture was evaporated under vacuum. The residue was dissolved in 1:1 methanol:dichloromethane and treated with MP-carbonate resin. After 2 hours stirring (pH7) the mixture was filtered, washing alternately with methanol and 1:1 dichloromethane:methanol. Evaporation afforded a yellow oil (56 mg, 77%). The spectroscopic data of this racemic material was identical to the chiral material described above (Example 1). This material was treated with excess hydrochloric acid (1M) in diethyl ether and the resulting solid was isolated to give the title compound (66 mg).

Example 2

(4R)-4-({4-[(2,3-Dihydro[1,4]dioxino[2,3-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one (E2 enantiomer series) dihydrochloride

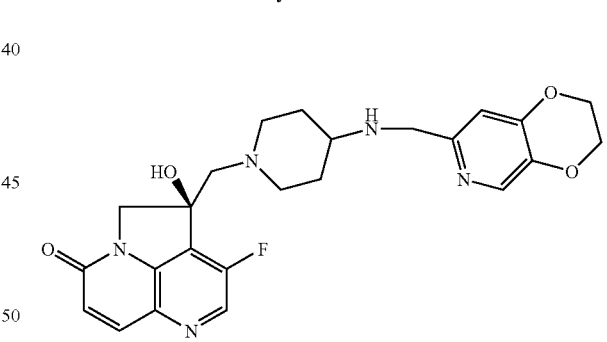

A solution of (4R)-4-[(4-amino-1-piperidinyl)methyl]-3-fluoro-4-hydroxy-4,5-dihydro-7H-pyrrolo[3,2,1-de]-1,5-naphthyridin-7-one (E2 enantiomer) (127 mg, 0.4 mmol) and 2,3-dihydro[1,4]dioxino[2,3-c]pyridine-7-carboxaldehyde (for a synthesis see WO2004058144, Example 2(c)) (66 mg, 0.4 mmol) in chloroform/methanol (1 ml/1 ml) was heated at 65° C. in the presence of 3 Å molecular sieves for 4 hours. The cooled mixture was treated with sodium triacetoxyborohydride (169 mg, 0.8 mmol) and stirred for 16 hours. The mixture was filtered through Kieselguhr, evaporated, then the residue partitioned between 20% methanol in dichloromethane and saturated aqueous sodium bicarbonate solution. The aqueous phase was further extracted (twice) with 20% methanol in dichloromethane and the combined extracts were dried and evaporated. This was chromatographed on silica eluting with dichloromethane/methanol/saturated aqueous ammonia (95:5:5) affording the free base of the title compound (144 mg, 77%), showing identical spectroscopic properties to the corresponding E1 enantiomer (Example 1).

This material (144 mg, 0.31 mmol) was dissolved in chloroform and treated with hydrochloric acid in ether then evaporated to dryness affording the title compound as a solid (163 mg).

Example 3A (4S)-4-({4-[(2,3-Dihydro-1,4-benzodioxin-6-ylmethyl)amino]-1-piperidinyl}methyl)-3-fluoro-4-hydroxy-4,5-dihydro-7H-pyrrolo[3,2,1-de]-1,5-naphthyridin-7-one (E1 enantiomer series) dihydrochloride

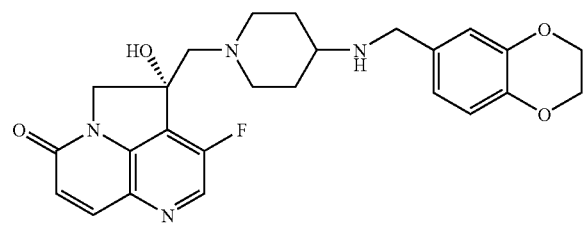

A solution of (4S)-4-[(4-amino-1-piperidinyl)methyl]-3-fluoro-4-hydroxy-4,5-dihydro-7H-pyrrolo[3,2,1-de]-1,5-naphthyridin-7-one (E1 enantiomer) (40 mg, 0.126 mmol) and 2,3-dihydro-1,4-benzodioxin-6-carbaldehyde (20 mg, 0.126 mmol) in N,N-dimethylformamide (2 ml) was treated with sodium triacetoxyborohydride (80 mg, 0.375 mmol). After stirring overnight the mixture was basified with saturated aqueous sodium carbonate solution and extracted with 10% methanol in dichloromethane. The combined organic extracts were dried and evaporated. The residue was chromatographed on silica eluting with 0-20% methanol in ethyl acetate affording the free base of the title compound (25 mg, 42%).

δH (CDCl$_3$, 400 MHz) 1.45-1.65 (2H, m), 1.90-2.00 (2H, m), 2.40 (1H, t), 2.55-2.65 (2H, m), 2.85 (1H, d), 2.95 (2H, m), 3.28 (1H, d), 3.72 (2H, s), 4.28 (4H, s), 4.35 (1H, d), 4.42 (1H, d), 6.75-6.88 (3H, m), 7.92 (1H, d), 8.38 (1H, s).

MS (+ve ion electrospray) m/z 467 (MH+).

This material was dissolved in dichloromethane and treated with hydrochloric acid in 1,4-dioxane, followed by trituration of the resultant solid with ether to give the title compound (22 mg).

Example 3B (4S)-4-({4-[(2,3-Dihydro-1,4-benzodioxin-6-ylmethyl)amino]-1-piperidinyl}methyl)-3-fluoro-4-hydroxy-4,5-dihydro-7H-pyrrolo[3,2,1-de]-1,5-naphthyridin-7-one (E1 enantiomer series) hydrochloride (4S)-4-({4-[(2,3-Dihydro-1,4-benzodioxin-6-ylmethyl)amino]-1-piperidinyl}methyl)-3-fluoro-4-hydroxy-4,5-dihydro-7H-pyrrolo[3,2,1-de]-1,5-naphthyridin-7-one (E1 enantiomer series) was treated with hydrochloric acid (1 equivalent) and then evaporated to afford the hydrochloride salt.

Example 4A (4S)-4-({4-[(3,4-Dihydro-2H-pyrano[2,3-c]pyridin-6-ylmethyl)amino]-1-piperidinyl}methyl)-3-fluoro-4-hydroxy-4,5-dihydro-7H-pyrrolo[3,2,1-de]-1,5-naphthyridin-7-one (E1 enantiomer series) dihydrochloride

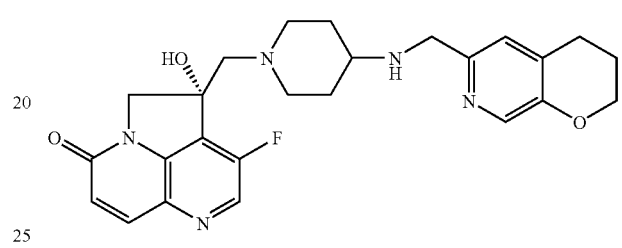

This was prepared from (4S)-4-[(4-amino-1-piperidinyl)methyl]-3-fluoro-4-hydroxy-4,5-dihydro-7H-pyrrolo[3,2,1-de]-1,5-naphthyridin-7-one (E1 enantiomer) (40 mg, 0.126 mmol) and 3,4-dihydro-2H-pyrano[2,3-c]pyridine-6-carbaldehyde (for a synthesis, see WO2004058144, Example 126 (e)) in a similar manner to Example 10 (sodium triacetoxyborohydride with N,N-dimethylformamide as solvent), affording the free base of the title compound as an oil (28 mg, 47%)

δH (CDCl$_3$, 250 MHz) 1.45-1.65 (2H, m), 1.90-2.10 (4H, m), 2.40 (1H, t), 2.50-2.65 (3H, m), 2.75 (1H, t), 2.85 (1H, d), 3.00 (2H, m), 3.28 (1H, d), 3.80 (2H, s), 4.20 (2H, m), 4.35 (1H, d), 4.45 (1H, d), 6.82 (1H, d), 6.98 (1H, s), 7.90 (1H, d), 8.06 (1H, s), 8.36 (1H, s).

MS (+ve ion electrospray) m/z 466 (MH+).

This material was dissolved in dichloromethane and treated with 4M HCl in 1,4-dioxane, followed by trituration of the resultant solid with ether to give the title compound (27 mg).

Example 4B (4S)-4-({4-[(3,4-Dihydro-2H-pyrano[2,3-c]pyridin-6-ylmethyl)amino]-1-piperidinyl}methyl)-3-fluoro-4-hydroxy-4,5-dihydro-7H-pyrrolo[3,2,1-de]-1,5-naphthyridin-7-one (E1 enantiomer series) hydrochloride (4S)-4-({4-[(3,4-Dihydro-2H-pyrano[2,3-c]pyridin-6-ylmethyl)amino]-1-piperidinyl}methyl)-3-fluoro-4-hydroxy-4,5-dihydro-7H-pyrrolo[3,2,1-de]-1,5-naphthyridin-7-one (E1 enantiomer series) was treated with hydrochloric acid in diethyl ether (0.55 ml) and then evaporated to afford the hydrochloride salt.

Example 5

(4R)-4-({4-[(3,4-Dihydro-2H-pyrano[2,3-c]pyridin-6-ylmethyl)amino]-1-piperidinyl}methyl)-3-fluoro-4-hydroxy-4,5-dihydro-7H-pyrrolo[3,2,1-de]-1,5-naphthyridin-7-one (E2 enantiomer series) hydrochloride

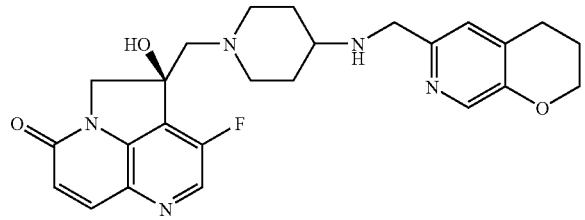

A solution of (4R)-4-[(4-amino-1-piperidinyl)methyl]-3-fluoro-4-hydroxy-4,5-dihydro-7H-pyrrolo[3,2,1-de]-1,5-naphthyridin-7-one (E2 enantiomer) (49 mg, 0.154 mmol) and 3,4-dihydro-2H-pyrano[2,3-c]pyridine-6-carbaldehyde (for a synthesis, see WO2004058144, Example 126(e)) (25 mg, 0.154 mmol) in dichloromethane/methanol (2 ml/0.2 ml) was treated with sodium triacetoxyborohydride (65 mg, 0.31 mmol). After 1 hour the mixture was evaporated and the residue chromatographed on silica eluting with 0-20% methanol in dichloromethane. The partially purified material was rechromatographed in a similar manner affording the monoacetate salt of the free base of the title compound (16 mg, 18%).

δH (CDCl₃, 400 MHz) 1.50-1.70 (2H, m), 1.90-2.10 (7H, m), 2.40 (1H, t), 2.55 (1H, t), 2.65 (1H, m), 2.75 (2H, t), 2.85 (1H, d), 3.00 (2H, m), 3.28 (1H, d), 3.85 (2H, s), 4.20 (2H, m), 4.35 (1H, d), 4.40 (1H, d), 6.82 (1H, d), 6.98 (1H, s), 7.90 (1H, d), 8.06 (1H, s), 8.36 (1H, s).

MS (+ve ion electrospray) m/z 466 (MH+).

This material was converted to the title compound (17 mg) by treatment with one equivalent of hydrochloric acid in 1,4-dioxane.

Example 6

(4S)-3-Fluoro-4-hydroxy-4-[(4-{[(3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one (E1 enantiomer series) dihydrochloride

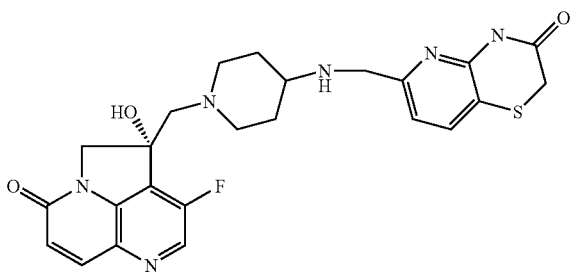

A solution of (4S)-4-[(4-amino-1-piperidinyl)methyl]-3-fluoro-4-hydroxy-4,5-dihydro-7H-pyrrolo[3,2,1-de]-1,5-naphthyridin-7-one (E1 enantiomer) (40 mg, 0.126 mmol) and 3-oxo-3,4-dihydro-2H-pyrido[3,2-b][1,4]thiazine-6-carboxaldehyde (for a synthesis, see WO2004058144, Example 7(d)) in N,N-dimethylformamide (1 ml) was treated with sodium triacetoxyborohydride (82 mg, 0.38 mmol). After stirring overnight more sodium triacetoxyborohydride (30 mg) was added. After 4 hours the mixture was basified with saturated aqueous sodium carbonate solution and extracted with 10% methanol in dichloromethane. The combined organic extracts were dried and evaporated. The residue was chromatographed on silica eluting with 0-20% methanol in dichloromethane affording the free base of the title compound.

δH (CDCl₃, 250 MHz) 1.40-1.65 (2H, m), 1.80-2.00 (2H, m), 2.40 (1H, t), 2.45-2.65 (2H, d), 2.85 (1H, d), 2.90-3.05 (2H, m), 3.25 (1H, d), 3.45 (2H, s), 3.85 (2H, s), 4.40 (2H, q), 6.80 (1H, d), 6.95 (1H, d), 7.58 (1H, d), 7.90 (1H, d), 8.37 (1H, s).

MS (+ve ion electrospray) m/z 497 (MH+).

This material was dissolved in methanol/chloroform and treated with hydrochloric acid in 1,4-dioxane to afford the title compound as a pale yellow solid (43 mg).

Example 7

(4R)-3-Fluoro-4-hydroxy-4-[(4-{[(3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one (E2 enantiomer series) dihydrochloride

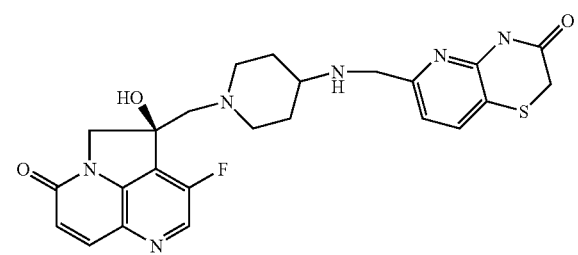

A solution of (4R)-4-[(4-amino-1-piperidinyl)methyl]-3-fluoro-4-hydroxy-4,5-dihydro-7H-pyrrolo[3,2,1-de]-1,5-naphthyridin-7-one (E2 enantiomer) (49 mg, 0.154 mmol) and 3-oxo-3,4-dihydro-2H-pyrido[3,2-b][1,4]thiazine-6-carboxaldehyde (for a synthesis, see WO2004058144, Example 7(d)) (30 mg) in chloroform/methanol (1 ml/1 ml) was treated with 3 A molecular sieves and heated to reflux for 4 hours under argon. The cooled mixture was treated with sodium triacetoxyborohydride (65 mg, 0.30 mmol) was added. The mixture was stirred overnight, filtered through Kieselguhr then partitioned between 20% methanol/dichloromethane and saturated aqueous sodium bicarbonate solution. The aqueous phase was further extracted with 20% methanol/dichloromethane and the combined extracts dried and evaporated. The residue was chromatographed on silica eluting with dichloromethane/methanol/saturated aqueous 880 ammonia (95:5:5) affording the free base of the title compound, the spectroscopic properties of which were identical to that of the corresponding E1 enantiomer (Example 6).

This material was dissolved in chloroform and treated with hydrochloric acid in ether. Evaporation afforded the title compound (53 mg).

Example 8A (4S)-4-({4-[(2,3-Dihydro[1,4]oxathiino[2,3-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one (E1 enantiomer series) dihydrochloride

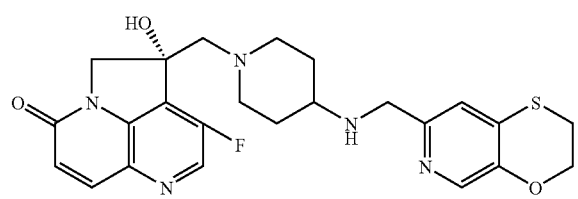

A solution of (4S)-4-[(4-amino-1-piperidinyl)methyl]-3-fluoro-4-hydroxy-4,5-dihydro-7H-pyrrolo[3,2,1-de]-1,5-naphthyridin-7-one (E1 enantiomer) (40 mg, 0.126 mmol) and 2,3-dihydro[1,4]oxathiino[2,3-c]pyridine-7-carbaldehyde (23 mg, 0.13 mmol) (for a synthesis, see WO2004058144, Example 60(i)) in N,N-dimethylformamide (1 ml) was treated with sodium triacetoxyborohydride (82 mg, 0.38 mmol). After stirring overnight the mixture was basified with saturated aqueous sodium carbonate solution and extracted with 10% methanol in dichloromethane. The combined organic extracts were dried and evaporated. The residue was chromatographed on silica eluting with 0-20% methanol in dichloromethane affording the free base of the title compound.

δH (CDCl$_3$, 250 MHz) 1.40-1.65 (2H, m), 1.85-2.00 (2H, m), 2.38 (1H, t), 2.45-2.65 (2H, d), 2.85 (1H, d), 2.90-3.05 (2H, m), 3.15-3.22 (2H, m), 3.25 (1H, d), 3.78 (2H, s), 4.30-4.50 (4H, m), 6.80 (1H, d), 7.00 (1H, s), 7.90 (1H, d), 8.00 (1H, s), 8.37 (1H, s).

MS (+ve ion electrospray) m/z 484 (MH+).

This material was dissolved in methanol/chloroform and treated with hydrochloric acid in 1,4-dioxane to afford the title compound as a pale yellow solid (32 mg).

Example 8B (4S)-4-({4-[(2,3-Dihydro[1,4]oxathiino[2,3-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one (E1 enantiomer series) hydrochloride (4S)-4-({4-[(2,3-Dihydro[1,4]oxathiino[2,3-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one (E1 enantiomer series) was treated with hydrochloric acid in diethyl ether (0.46 ml) and then evaporated to afford the hydrochloride salt.

Example 9

(4R)-4-({4-[(2,3-Dihydro[1,4]oxathiino[2,3-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one (E2 enantiomer series) hydrochloride

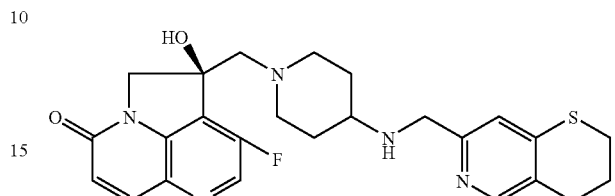

A solution of (4R)-4-[(4-amino-1-piperidinyl)methyl]-3-fluoro-4-hydroxy-4,5-dihydro-7H-pyrrolo[3,2,1-de]-1,5-naphthyridin-7-one (E2 enantiomer) (55 mg, 0.173 mmol) and 2,3-dihydro[1,4]oxathiino[2,3-c]pyridine-7-carbaldehyde (31 mg, 0.173 mmol) (for a synthesis, see WO2004058144, Example 60(i)) in dichloromethane/methanol (2 ml/0.2 ml) was treated with sodium triacetoxyborohydride (73 mg, 0.35 mmol). After 1 hour the mixture was evaporated and the residue chromatographed on silica eluting with 0-20% methanol in dichloromethane affording the monoacetate salt of the free base of the title compound (41 mg, 49%).

δH (CDCl$_3$, 400 MHz) 1.50-1.70 (2H, m), 1.90-2.00 (5H, m), 2.38 (1H, t), 2.50 (1H, t), 2.65 (1H, m), 2.78 (1H, d), 2.95 (1H d), 3.05 (1H, d), 3.15 (2H, m), 3.20 (1H, d), 3.85 (2H, s), 4.46-4.52 (4H, m), 6.80 (1H, d), 7.00 (1H, s), 7.88 (1H, d), 7.98 (1H, s), 8.36 (1H, s).

MS (+ve ion electrospray) m/z 484 (MH+).

This material was converted to the title compound (37 mg) by treatment with one equivalent of hydrochloric acid in 1,4-dioxane.

Example 10A (4S)-3-Fluoro-4-hydroxy-4-({4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one (E1 enantiomer series) dihydrochloride

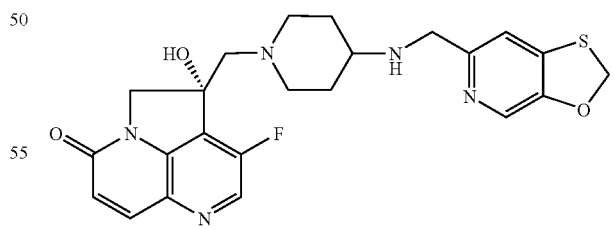

A solution of (4S)-4-[(4-amino-1-piperidinyl)methyl]-3-fluoro-4-hydroxy-4,5-dihydro-7H-pyrrolo[3,2,1-de]-1,5-naphthyridin-7-one (E1 enantiomer) (40 mg, 0.126 mmol) and [1,3]oxathiolo[5,4-c]pyridine-6-carbaldehyde (21 mg, 0.126 mmol) (for a synthesis, see WO2004058144, Example 61) in N,N-dimethylformamide (2 ml) was treated with sodium triacetoxyborohydride (81 mg, 0.382 mmol). After stirring overnight further sodium triacetoxyborohydride was added and the mixture stirred for 7 hours. The mixture was basified with saturated aqueous sodium carbonate solution and extracted with 10% methanol in dichloromethane. The combined organic extracts were dried and evaporated. The residue was chromatographed on silica eluting with 0-20% methanol in ethyl acetate affording the free base of the title compound (32 mg, 54%).

δH (CDCl$_3$, 250 MHz) 1.38-2.03 (6H, m), 2.40 (1H, t), 2.50-2.68 (2H, m), 2.85 (1H, d), 2.90-3.05 (2H, m), 3.29 (1H, d), 3.83 (2H, s), 4.39 (2H, q), 5.73 (2H, s), 6.84 (1H, d), 7.20 (1H, s), 7.90 (1H, d), 8.01 (1H, s), 8.37 (1H, s).

MS (+ve ion electrospray) m/z 470 (MH+).

This material was dissolved in dichloromethane and treated with hydrochloric acid in 1,4-dioxane, followed by trituration of the resultant solid with ether to give the title compound (37 mg).

Example 10B (4S)-3-Fluoro-4-hydroxy-4-({4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one (E1 enantiomer series) hydrochloride (4S)-3-Fluoro-4-hydroxy-4-({4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one was converted to the title compound by treatment with one equivalent of 5M aqueous hydrochloric acid.

Example 11

(4R)-3-Fluoro-4-hydroxy-4-({4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one (E2 enantiomer series) hydrochloride

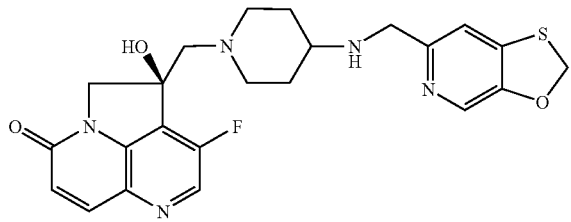

A solution of (4R)-[(4-amino-1-piperidinyl)methyl]-3-fluoro-4-hydroxy-4,5-dihydro-7H-pyrrolo[3,2,1-de]-1,5-naphthyridin-7-one (E2 enantiomer) (48 mg, 0.151 mmol) and [1,3]oxathiolo[5,4-c]pyridine-6-carbaldehyde (25 mg, 0.151 mmol) (for a synthesis, see WO2004058144, Example 61) in dichloromethane/methanol (2 ml/0.2 ml) was treated with sodium triacetoxyborohydride (64 mg, 0.30 mmol). After 1 hour the mixture was evaporated and the residue chromatographed on silica eluting with 0-20% methanol in dichloromethane affording the monoacetate of the free base of the title compound (38 mg, 54%).

δH (CDCl$_3$, 400 MHz) 1.60-1.80 (2H, m), 1.95-2.05 (5H, m), 2.40 (1H, t), 2.50 (1H, t), 2.78 (1H, m), 2.85 (1H, d), 2.95 (1H, d), 3.08 (1H, d), 3.25 (1H, d), 3.95 (2H, s), 4.60 (2H, s), 5.78 (2H, s), 6.82 (1H, d), 7.20 (1H, s), 7.90 (1H, d), 7.98 (1H, s), 8.37 (1H, s).

MS (+ve ion electrospray) m/z 470 (MH+).

This material was converted to the title compound by treatment with one equivalent of hydrochloric acid in 1,4-dioxane (38 mg).

Example 12

(4R/S)-3-Chloro-4-({4-[(2,3-dihydro[1,4]dioxino[2,3-c]pyridin-7-ylmethyl)amino]-1-piperidinyl}methyl)-4-hydroxy-4,5-dihydro-7H-pyrrolo[3,2,1-de]-1,5-naphthyridin-7-one dihydrochloride

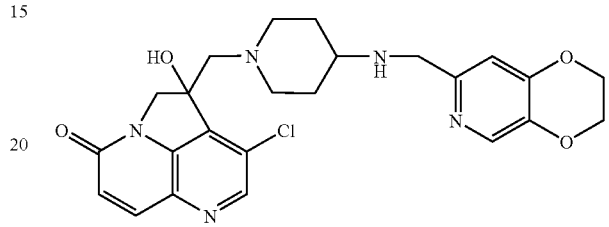

(a) Dimethyl [3-chloro-6-(methyloxy)-1,5-naphthyridin-4-yl]propanedioate

Method 1

To a solution of dimethylmalonate (82 ml, 715 mmol) in N,N-dimethylformamide (1400 ml) at 0° C. was added sodium hydride (60% dispersion in oil) (28.6 g, 715 mmol). The mixture was stirred for 0.5 hour and sonicated for 0.5 hour before adding 1,1,1-trifluoro-methanesulfonic acid 3-chloro-6-methoxy-[1,5]naphthyridin-4-yl ester (for a synthesis see WO2004058144, Example 1(b)) (88.88 g, 238.5 mmol). The reaction mixture was then heated at 50° C. for 12 hours. The reaction was cooled, treated with ethyl acetate, water and HCl (2M) (340 ml). The organic phase was washed twice with water, dried and the solvent was removed under reduced pressure. The residue was treated with toluene and stirred for 1 hour. Filtration gave the desired compound. The toluene solution was subjected to column chromatography on silica gel using a hexane and ethyl acetate gradient to provide more of the desired compound; (total yield: 62.72 g, 81%).

MS (+ve ion electrospray) m/z 325 (MH$^+$).

Method 2

(i) 8-Bromo-7-chloro-2-(methyloxy)-1,5-naphthyridine

To a solution of 3-chloro-6-(methyloxy)-1,5-naphthyridin-4(1H)-one (3-chloro-6-(methoxy)-1,5-naphthyridin-4-ol, for a synthesis see WO2004058144, Example 1(a)) (43 g, 204.8 mmol) in N,N-dimethylformamide (500 ml) at 0° C. was added phosphorous tribromide dropwise (23.3 ml, 245.8 mmol). The reaction mixture was then stirred at 10° C. for 0.5 hour and then at 25° C. for 1 hour. The mixture was then poured onto 1600 ml of water and basified to pH 7 with potassium carbonate. The solid formed was filtered off, washed with water and dried in vacuo to afford the desired compound (51 g, 91%).

MS (+ve ion electrospray) m/z 274 (MH$^+$)

(ii) Dimethyl [3-chloro-6-(methyloxy)-1,5-naphthyridin-4-yl]propanedioate

To a solution of dimethylmalonate (68.6 ml, 600 mmol) in 1,4-dioxane (600 ml) was added sodium hydride (60% dispersion in oil)(22 g, 550 mmol). The mixture was stirred at 75° C. for 2 hours before adding 8-bromo-7-chloro-2-(methyloxy)-1,5-naphthyridine (54.5 g, 200 mmol) and copper(I) bromide (10 g, 69.7 mmol). The reaction mixture was then heated at 100° C. for 12 hours. The reaction was cooled, treated with ethyl acetate, water and HCl (2N) (175 ml). The aqueous phase was extracted with ethyl acetate. The organic phase was washed twice with water, dried and the solvent was removed under reduced pressure. The residue was subjected to column chromatography on silica gel using a hexane and ethyl acetate gradient to provide the desired compound (63 g, 97%).

MS (+ve ion electrospray) m/z 325 (MH$^+$).

(b) Methyl [3-chloro-6-(methyloxy)-1,5-naphthyridin-4-yl]acetate

To a solution of dimethyl [3-chloro-6-(methyloxy)-1,5-naphthyridin-4-yl]propanedioate (56 g, 173 mmol) in dimethylsulfoxide (1210 ml) was added lithium chloride (14.9 g, 350 mmol) and water (3.2 ml, 180 mmol). The mixture was heated to 100° C. for 16 hours then cooled and treated with ethyl acetate and water. The organic phase was washed twice with water, the aqueous extracted with ethyl acetate and this water-washed. The combined organic phases were dried and the solvent was removed under reduced pressure. The residue was subjected to column chromatography on silica gel using a hexane and ethyl acetate gradient to provide the desired compound (43 g, 94%).

MS (+ve ion electrospray) m/z 267 (MH$^+$).

(c) Methyl 2-[3-chloro-6-(methyloxy)-1,5-naphthyridin-4-yl]-2-propenoate

To a solution of methyl [3-chloro-6-(methyloxy)-1,5-naphthyridin-4-yl]acetate (43 g, 162 mmol) in cyclohexane (1060 ml) was added benzyltriethylammonium chloride (71.2 g, 313 mmol), potassium carbonate (42 g, 304 mmol) and paraformaldehyde (42 g). The reaction mixture was then heated at 80° C. for 24 hours, cooled and treated with ethyl acetate and water. The aqueous was extracted with ethyl acetate. The combined organic phases were dried and the solvent was removed under reduced pressure. The residue was subjected to column chromatography on silica gel using a hexane and ethyl acetate gradient to provide the desired compound (40 g, 89%).

MS (+ve ion electrospray) m/z 279 (MH$^+$).

(d) Methyl (2R/S)-2-[3-chloro-6-(methyloxy)-1,5-naphthyridin-4-yl]-3-[(3R,4S)-4-({[(1,1-dimethylethyl)oxy]carbonyl}amino-3-hydroxy-1-piperidinyl}propanoate A mixture of methyl 2-[3-chloro-6-(methyloxy)-1,5-naphthyridin-4-yl]-2-propenoate (10 g), 1,1-dimethylethyl[(3R,4S)-3-hydroxy-4-piperidinyl]carbamate (for a synthesis, see WO2004058144, Example 34(a), cis-4-tert-butoxycarbonylamino-3-hydroxy-piperidine enantiomer 1) (8.05 g) and 1,1,3,3-tetramethylguanidine (1 ml) in N,N-dimethylformamide (40 ml) was heated at 80° C. for 4 hours, cooled and evaporated to dryness. Chromatography, eluting with methanol/dichloromethane, gave the product (17.4 g 98%).

MS (+ve ion electrospray) m/z 495 (MH+).

(e) 1,1-Dimethylethyl ((3R,4S)-1-{(2R/S)-2-[3-chloro-6-(methyloxy)-1,5-naphthyridin-4-yl]-3-hydroxypropyl}-3-hydroxy-4-piperidinyl)carbamate A solution of methyl (2R/S-2-[3-chloro-6-(methyloxy)-1,5-naphthyridin-4-yl]-3-[(3R,4S)-4-({[(1,1-dimethylethyl)oxy]carbonyl}amino-3-hydroxy-1-piperidinyl}propanoate (17.4 g, 35.2 mmol) in THF (400 ml) at −70° C. under argon was treated dropwise with a 1M solution of lithium aluminium hydride in THF (40.5 ml, 40.5 mmol) and allowed to warm gradually to 0° C. The solution was stirred at this temperature for 2 hours, treated with water (3 ml), 2N sodium hydroxide (5.7 ml) and water (6.6 ml), stirred for 1 hour at room temperature and filtered. The filtrate was evaporated and the residue chromatographed, eluting with methanol/dichloromethane to give the product (8.75 g, 53%).

MS (+ve ion electrospray) m/z 467 (MH$^+$).

(f) 3-Chloro-4-methylidene-4,5-dihydro-7H-pyrrolo[3,2,1-de]-1,5-naphthyridin-7-one A solution of 1,1-dimethylethyl ((3R,4S)-1-{(2R/S)-2-[3-chloro-6-(methyloxy)-1,5-naphthyridin-4-yl]-3-hydroxypropyl}-3-hydroxy-4-piperidinyl)carbamate (8.75 g, 18.7 mmol) and diisopropylethylamine (4.9 ml) in dichloromethane (90 ml) was treated at 0° C. under argon with para-toluenesulphonic anhydride (6.7 g, 20.6 mmol). After 3 hours at room temperature more para-toluenesulphonic anhydride (0.7 g) was added. After 2.5 days the mixture was washed with saturated aqueous sodium bicarbonate solution. The aqueous phase was extracted with dichloromethane (2×) and the combined organic extracts dried and evaporated. The residue was chromatographed, eluting with methanol/dichloromethane to give firstly the partially purified title compound (0.84 g, 21%) then 1,1-dimethylethyl {(3R,4S)-1-[(3-chloro-7-oxo-4,5-dihydro-7H-pyrrolo[3,2,1-de]-1,5-naphthyridin-4-yl)methyl]-3-hydroxy-4-piperidinyl}carbamate (3.93 g, 48%). The partially purified title compound (0.84 g) was further purified by chromatography eluting with methanol/dichloromethane affording pure product (0.57 g).

MS (+ve ion electrospray) m/z 219 (MH+).

(g) (4R/S)-3-Chloro-4-hydroxy-4-(hydroxymethyl)-4,5-dihydro-7H-pyrrolo[3,2,1-de]-1,5-naphthyridin-7-one A solution of 3-chloro-4-methylidene-4,5-dihydro-7H-pyrrolo[3,2,1-de]-1,5-naphthyridin-7-one (565 mg, 2.6 mol) in tert-butanol/water (25 ml/25 ml) was treated with AD-mix alpha/beta (3.5 g/3.5 g) and stirred overnight. Sodium sulphite (5 g) was added and the mixture was stirred for 1 hour. Ethyl acetate, saturated aqueous sodium bicarbonate solution and brine were added. The phases were separated and the aqueous phase was extracted twice more with ethyl acetate. The combined organic extracts were dried and evaporated. The crude material was chromatographed affording the product (300 mg).

MS (+ve ion electrospray) m/z 253 (MH+).

(h) [(4R/S)-(3-Chloro-4-hydroxy-7-oxo-4,5-dihydro-7H-pyrrolo[3,2,1-de]-1,5-naphthyridin-4-yl)]methyl 4-methylbenzenesulfonate A suspension of (4R/S)-3-chloro-4-hydroxy-4-(hydroxymethyl)-4,5-dihydro-7H-pyrrolo[3,2,1-de]-1,5-naphthyridin-7-one (300 mg, 1.2 mmol) in dichloromethane/tetrahydrofuran/N,N-dimethylformamide (10 ml/10 ml/2 ml) was treated with triethylamine (0.25 ml, 1.8 mmol), para-toluenesulphonyl chloride (220 mg, 1.2 mol) and dibutyltin oxide (15 mg, 0.06 mmol). After 3 hours water was added and the phases separated. The organic phase was washed with saturated aqueous sodium bicarbonate solution then dried and evaporated affording the product (465 mg).

MS (+ve ion electrospray) m/z 407 (MH+).

(i) 1,1-dimethylethyl (1-{[(4R/S)-3-chloro-4-hydroxy-7-oxo-4,5-dihydro-7H-pyrrolo[3,2,1-de]-1,5-naphthyridin-4-yl]methyl}-4-piperidinyl)carbamate A mixture of [(4R/S)-(3-chloro-4-hydroxy-7-oxo-4,5-dihydro-7H-pyrrolo[3,2,1-de]-1,5-naphthyridin-4-yl)methyl 4-methylbenzenesulfonate (465 mg, 1.15 mmol), 1,1-dimethylethyl 4-piperidinylcarbamate (218 mg, 1.1 mmol) and sodium carbonate (350 mg, 3.3 mmol) in ethanol (12.5 ml). After 1 day more 1,1-dimethylethyl 4-piperidinylcarbamate (100 mg) was added. After 1 hour the mixture was evaporated and the residue was partitioned between 20% methanol/dichloromethane and water. The organic extract was dried and evaporated. The crude material was chromatographed affording the product (410 mg, 82%).

MS (+ve ion electrospray) m/z 435.5 (MH+).

(j) (4R/S)-4-[(4-amino-1-piperidinyl)methyl]-3-chloro-4-hydroxy-4,5-dihydro-7H-pyrrolo[3,2,1-de]-1,5-naphthyridin-7-one 1,1-dimethylethyl (1-{[(4R/S-3-chloro-4-hydroxy-7-oxo-4,5-dihydro-7H-pyrrolo[3,2,1-de]-1,5-naphthyridin-4-yl]methyl}-4-piperidinyl)carbamate (410 mg) was dissolved in dichloromethane/trifluoroacetic acid (5 ml/4 ml). After 30 minutes the mixture was evaporated. The residue was dissolved in methanol and treated with Amberlyst resin. After 1 hour the mixture was filtered and the filtrate evaporated to dryness. The crude material was chromatographed on silica eluting with 0-20% of 2M ammonia/methanol in dichloromethane affording the product (300 mg, 95%).

MS (+ve ion electrospray) m/z 335.5 (MH+).

(k) Title Compound

A solution of (4R/S)-4-[(4-amino-1-piperidinyl)methyl]-3-chloro-4-hydroxy-4,5-dihydro-7H-pyrrolo[3,2,1-de]-1,5-naphthyridin-7-one (50 mg, 0.15 mmol) and 2,3-dihydro[1,4]dioxino[2,3-c]pyridine-7-carboxaldehyde (for a synthesis, see WO2004058144, Example 2(c)) (25 mg, 0.15 mmol) in chloroform/methanol (2 ml/2 ml) was stirred at room temperature for 2 hours then treated with sodium triacetoxyborohydride (96 mg, 0.45 mmol). After 2 hours the reaction mixture was evaporated and the residue chromatographed on silica eluting with 0-20% methanol in dichloromethane affording the monoacetate salt of the free base of the title compound (55 mg, 70%).

δH (CDCl₃, 400 MHz) 1.50 (1H, m), 1.62 (1H, m), 1.85-1.95 (2H, t), 2.00 (3H, s), 2.35 (1H, t), 2.50 (1H, t), 2.65 (1H, m), 2.85 (1H, d), 2.90 (1H, d), 3.05 (1H, d), 3.45 (1H, d), 3.85 (2H, s), 4.39 (2H, m), 4.45 (3H, m), 4.50 (1H, d), 6.84 (1H, s), 6.87 (1H, d), 7.90 (1H, d), 8.01 (1H, s), 8.40 (1H, s).

MS (+ve ion electrospray) m/z 484 (MH+).

This material was dissolved in dichloromethane and treated with hydrochloric acid in 1,4-dioxane, followed by trituration of the resultant solid with ether to give the title compound.

Example 13

(4R/S)-3-Chloro-4-({4-[(3,4-dihydro-2H-pyrano[2,3-c]pyridin-6-ylmethyl)amino]-1-piperidinyl}methyl)-4-hydroxy-4,5-dihydro-7H-pyrrolo[3,2,1-de]-1,5-naphthyridin-7-one dihydrochloride

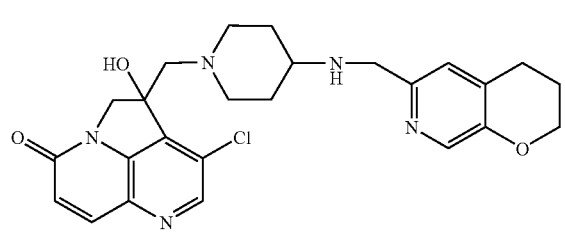

A solution of (4R/S)-4-[(4-amino-1-piperidinyl)methyl]-3-chloro-4-hydroxy-4,5-dihydro-7H-pyrrolo[3,2,1-de]-1,5-naphthyridin-7-one (50 mg, 0.15 mmol) and 3,4-dihydro-2H-pyrano[2,3-c]pyridine-6-carbaldehyde (for a synthesis, see WO2004058144, Example 126(e)) (25 mg, 0.15 mmol) in chloroform/methanol (2 ml/2 ml) was stirred at room temperature for 2 hours then treated with sodium triacetoxyborohydride (96 mg, 0.45 mmol). After 2 hours the reaction mixture was evaporated and the residue chromatographed on silica eluting with 0-20% methanol in dichloromethane affording the monoacetate salt of the free base of the title compound (70 mg, 88%).

δH (CDCl₃, 400 MHz) 1.58 (1H, m), 1.70 (1H, m), 1.85-2.05 (7H, m), 2.38 (1H, t), 2.55 (1H, t), 2.70-2.80 (3H, m), 2.85 (1H, d), 2.90 (1H, d), 3.05 (1H, d), 3.45 (1H, d), 3.90 (2H, s), 4.20 (2H, t), 4.35 (1H, d), 4.50 (1H, d), 6.86 (1H, d), 7.02 (1H, s), 7.90 (1H, d), 8.05 (1H, s), 8.40 (1H, s).

MS (+ve ion electrospray) m/z 482 (MH+).

This material was dissolved in dichloromethane and treated with hydrochloric acid in 1,4-dioxane, followed by trituration of the resultant solid with ether to give the title compound.

Example 14

(4R/S)-3-Chloro-4-hydroxy-4-[(4-{[(3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one dihydrochloride

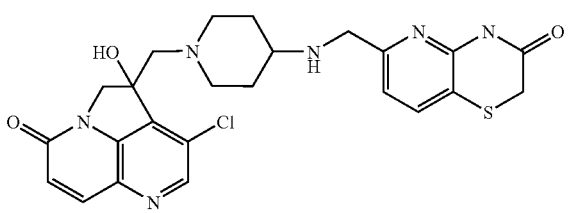

A solution of (4R/S)-4-[(4-amino-1-piperidinyl)methyl]-3-chloro-4-hydroxy-4,5-dihydro-7H-pyrrolo[3,2,1-de]-1,5-naphthyridin-7-one (50 mg, 0.15 mmol) and 3-oxo-3,4-dihydro-2H-pyrido[3,2-b][1,4]thiazine-6-carboxaldehyde (for a synthesis, see WO2004058144, Example 7(d)) (29 mg, 0.15 mmol) in chloroform/methanol (2 ml/2 ml) was stirred at room temperature for 2 hours then treated with sodium triacetoxyborohydride (96 mg, 0.45 mmol). After 2 hours the reaction mixture was evaporated and the residue chromatographed on silica eluting with 0-20% methanol in dichloromethane affording the monoacetate salt of the free base of the title compound (77 mg, 95%).

δH (CDCl$_3$, 400 MHz) 1.58 (1H, m), 1.70 (1H, m), 1.90-2.05 (6H, m), 2.38 (1H, t), 2.50 (1H, t), 2.75 (1H, m), 2.90 (1H, d), 3.10 (1H, d), 3.35 (1H, d), 3.50 (2H, s), 3.95 (2H, s), 4.35 (1H, d), 4.55 (1H, d), 6.85 (1H, d), 6.97 (1H, d), 7.58 (1H, d), 7.90 (1H, d), 8.42 (1H, s).

MS (+ve ion electrospray) m/z 514 (MH+).

This material was dissolved in dichloromethane and treated with hydrochloric acid in 1,4-dioxane, followed by trituration of the resultant solid with ether to give the title compound.

Example 15

(4R/S)-3-Chloro-4-hydroxy-4-({4-[([1,3]oxathiolo [5,4-c]pyridin-6-ylmethyl)amino]-1-piperidinyl}methyl)-4,5-dihydro-7H-pyrrolo[3,2,1-de]-1,5-naphthyridin-7-one dihydrochloride

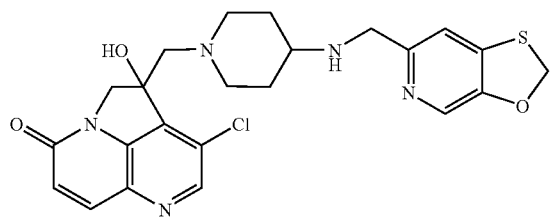

A solution of (4R/S)-4-[(4-amino-1-piperidinyl)methyl]-3-chloro-4-hydroxy-4,5-dihydro-7H-pyrrolo[3,2,1-de]-1,5-naphthyridin-7-one (50 mg, 0.15 mmol) and [1,3]oxathiolo [5,4-c]pyridine-6-carbaldehyde (25 mg, 0.15 mmol) (for a synthesis, see WO2004058144, Example 61) in chloroform/methanol (2 ml/2 ml) was stirred at room temperature for 2 hours then treated with sodium triacetoxyborohydride (96 mg, 0.45 mmol). After 2 hours the reaction mixture was evaporated and the residue chromatographed on silica eluting with 0-20% methanol in dichloromethane affording the monoacetate salt of the free base of the title compound (73 mg, 95%).

δH (CDCl$_3$, 400 MHz) 1.58 (1H, m), 1.68 (1H, m), 1.95 (2H, t), 2.00 (3H, s), 2.38 (1H, t), 2.50 (1H, t), 2.73 (1H, m), 2.85 (1H, d), 2.90 (1H, d), 3.08 (1H, d), 3.35 (1H, d), 3.92 (2H, s), 4.37 (1H, d), 4.50 (1H, d), 5.76 (2H, s), 6.85 (1H, d), 7.20 (1H, s), 7.90 (1H, d), 8.05 (1H, s), 8.42 (1H, s).

MS (+ve ion electrospray) m/z 486 (MH+).

This material was dissolved in dichloromethane and treated with hydrochloric acid in 1,4-dioxane, followed by trituration of the resultant solid with ether to give the title compound.

Example 16A (4S)-3,8-Difluoro-4-hydroxy-4-({4-[([1,3]oxathiolo [5,4-c]pyridin-6-ylmethyl)amino]-1-piperidinyl}methyl)-4,5-dihydro-7H-pyrrolo[3,2,1-de]-1,5-naphthyridin-7-one dihydrochloride

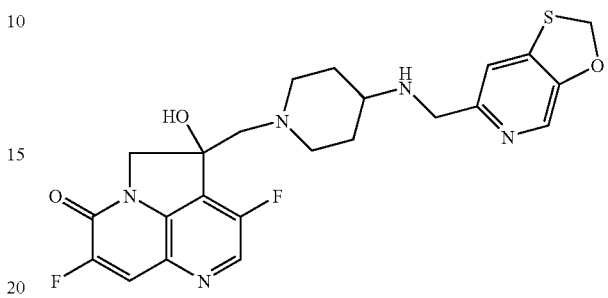

(a) 2-Chloro-5-fluoro-6-(methyloxy)-3-pyridinecarboxylic acid

A solution of 2,6-dichloro-5-fluoro-3-pyridinecarboxylic acid (51.12 g, 243 mmol) in methanol (400 ml) was treated with sodium methoxide in methanol (25% w/v, 100 ml, 535 mmol) and the mixture heated to reflux for 4 hours. The cooled mixture was treated with water (400 ml) and acidified to pH2 with aqueous hydrochloric acid (2M) then concentrated to ca 400 ml. Filtration, washing with water and drying in vacuo over P$_2$O$_5$ for 18 h afforded the product as a white solid (32.65 g, 65%).

MS (+ve ion electrospray) m/z 208 (MH+).

(b) 1,1-Dimethylethyl [2-chloro-5-fluoro-6-(methyloxy)-3-pyridinyl]carbamate

A mixture of 2-chloro-5-fluoro-6-(methyloxy)-3-pyridinecarboxylic acid (32.65 g, 159 mmol) in toluene/triethylamine/tert-butanol (300 ml/26.4 ml/75 ml) was treated with diphenylphosphoryl azide (37.7 ml, 174.8 mmol) and heated to 100° C. for 2 hours. The mixture was treated with saturated aqueous sodium bicarbonate solution (500 ml) then extracted with ethyl acetate (3×500 ml). The combined organic extracts were dried over magnesium sulphate and evaporated. The residue was chromatographed eluting with 0-40% dichloromethane in petrol affording the product as a white solid (36.35 g, 83%).

MS (+ve ion electrospray) m/z 221/223 (M(-t-Bu)H+).

(c) 1,1-Dimethylethyl [2-[1-(ethyloxy)ethenyl]-5-fluoro-6-(methyloxy)-3-pyridinyl]carbamate A degassed solution of 1,1-dimethylethyl [2-chloro-5-fluoro-6-(methyloxy)-3-pyridinyl]carbamate (20 g, 72.2 mmol) in 1,4-dioxane (200 ml) was treated with bis(tri-tert-butylphosphine) palladium(0) (1.05 g), caesium fluoride (21.93 g) and tributyl[1-(ethyloxy)ethenyl]stannane (26.9 ml) then heated to 100° C. overnight. The cooled mixture was treated with 10% aqueous potassium fluoride solution. After 0.5 hour stirring, the mixture was filtered through Kieselguhr, washing with 1,4-dioxane. Ethyl acetate and water were added to the filtrate. The phases were separated and the aqueous phase extracted twice with ethyl acetate. The combined organic extracts were dried over magnesium sulphate and evaporated. The residue was rapidly chromatographed eluting with 25-50% dichloromethane in hexane affording the product as a light brown oil (22.2 g, 99%).

MS (+ve ion electrospray) m/z 313 (MH+).

(d) 1,1-Dimethylethyl [5-fluoro-2-(fluoroacetyl)-6-(methyloxy)-3-pyridinyl]carbamate A mixture of 1,1-dimethylethyl [2-[1-(ethyloxy)ethenyl]-5-fluoro-6-(methyloxy)-3-pyridinyl]carbamate (6.72 g, 21.54 mmol), acetonitrile (70 ml), and saturated aqueous sodium bicarbonate solution (15 ml) was treated portionwise over 5 minutes at 0° C. under argon with [1-(chloromethyl)-4-fluoro-1,4-diazoniabicyclo[2.2.2]octane bis(tetrafluoroborate) (Selectfluor™) (8.9 g, 25.05 mmol). After the addition the mixture was stirred at room temperature for 0.5 hour then treated with saturated aqueous sodium bicarbonate solution (50 ml), stirred for 10 minutes, then diluted with water (100 ml) and extracted with ethyl acetate (3×200 ml). The combined organic extracts were dried over magnesium sulphate and evaporated. The residue was chromatographed eluting with 0-50% dichloromethane in hexane affording the product as a white solid (3.72 g, 57%).

MS (+ve ion electrospray) m/z 247 (M(-t-Bu)H+).

(e) 1,1-Dimethylethyl [2-[3-(dimethylamino)-2-fluoroacryloyl]-5-fluoro-6-(methyloxy)-3-pyridinyl]carbamate A solution of 1,1-dimethylethyl [5-fluoro-2-(fluoroacetyl)-6-(methyloxy)-3-pyridinyl]carbamate (3.72 g, 12.32 mmol) in dry toluene (20 ml) was treated with {(dimethylamino)[(1,1-dimethylethyl)oxy]methyl}dimethylamine (Bredereck's reagent) (3.05 ml, 14.78 mmol) and heated at 40° C. for 2 hours. The mixture was evaporated and the residue triturated with 3×200 ml hexane and the remaining solid dried in vacuo to afford the product (2.15 g, 49%).

MS (+ve ion electrospray) m/z 358 (MH+).

(f) 8-Bromo-3,7-difluoro-2-(methyloxy)-1,5-naphthyridine

A solution of 1,1-dimethylethyl [2-[3-(dimethylamino)-2-fluoroacryloyl]-5-fluoro-6-(methyloxy)-3-pyridinyl]carbamate (2.15 g, 6.02 mmol) in trifluoroacetic acid/dichloromethane (20 ml/20 ml) was stirred at room temperature for 0.5 hour under argon and evaporated. The residue was treated with ~50 ml 2M ammonia in methanol until basic and evaporated. This residue was dried in vacuo then chromatographed eluting with 0-10% methanol in ethyl acetate affording a solid (3.64 g), 8-hydroxy-3,7-difluoro-2-(methyloxy)-1,5-naphthyridine. 8-Hydroxy-3,7-difluoro-2-(methyloxy)-1,5-naphthyridine (3.64 g) was dissolved in N,N-dimethylformamide (20 ml) and treated with phosphorus tribromide (0.68 ml, 7.22 mmol). After 1 hour, more phosphorus tribromide (0.68 ml, 7.22 mmol) was added. After 0.5 hour the mixture was diluted with water and basified with solid potassium carbonate. Filtration and drying in vacuo afforded the product (0.95 g, 57%).

MS (+ve ion electrospray) m/z 275/277 (MH+).

(g) 3,7-Difluoro-8-(1-methylethenyl)-2-(methyloxy)-1,5-naphthyridine

A solution of 8-bromo-3,7-difluoro-2-(methyloxy)-1,5-naphthyridine (1.14 g, 4.15 mmol) and tetrakis(triphenylphosphine)palladium(0) (240 mg, 0.21 mmol) in degassed dimethoxyethane (40 ml) was stirred under argon for 30 minutes. Potassium carbonate (570 mg, 4.2 mmol), water (12 ml) and pyridine-tris(1-methylethenyl)boroxin (1:1) (470 mg, 1.66 mmol) were added the mixture was heated to reflux for 5 hours. The cooled mixture was treated with water (100 ml) and ether (200 ml). The phases were separated and the aqueous phase further extracted with ether (2×200 ml). The combined organic extracts were dried over magnesium sulphate and evaporated. The residue was chromatographed on silica eluting with a gradient of 0-50% ethyl acetate in hexane affording a white solid (820 mg, 84%).

MS (+ve ion electrospray) m/z 237 (MH+).

(h) 8-[1-(Chloromethyl)ethenyl]-3,7-difluoro-2-(methyloxy)-1,5-naphthyridine A solution of 3,7-difluoro-8-(1-methylethenyl)-2-(methyloxy)-1,5-naphthyridine (820 mg, 3.5 mmol) in tert-butanol (50 ml) under argon was treated with cerium(III) chloride heptahydrate (1.29 g, 3.5 mmol) followed by a solution of sodium hypochlorite (12% w/v, 2.6 ml, 4.2 mmol). After 30 minutes stirring, saturated aqueous sodium sulphite solution (20 ml) was added. After 15 minutes stirring the mixture was extracted with ether (3×200 ml). The combined organic extracts were dried over magnesium sulphate and evaporated. The residue was chromatographed on silica eluting a gradient of 0-50% ethyl acetate in hexane affording a white solid (320 mg, 34%).

MS (+ve ion electrospray) m/z 271/273 (MH+).

(i) 3,8-Difluoro-4-methylidene-4,5-dihydro-7H-pyrrolo[3,2,1-de]-1,5-naphthyridin-7-one A mixture of 8-[1-(chloromethyl)ethenyl]-3,7-difluoro-2-(methyloxy)-1,5-naphthyridine (320 mg, 1.18 mmol) and sodium iodide (885 mg) in acetonitrile (20 ml) was heated to reflux for 20 hours. The cooled mixture was evaporated then diluted with water and extracted with dichloromethane. The organic extracts were dried over magnesium sulphate and evaporated. The residue was chromatographed on silica eluting with a gradient of 0-100% ethyl acetate in hexane affording product (168 mg, 65%).

MS (+ve ion electrospray) m/z 221 (MH+).

(j) 3,8-Difluoro-4-hydroxy-4-(hydroxymethyl)-4,5-dihydro-7H-pyrrolo[3,2,1-de]-1,5-naphthyridin-7-one A solution of 3,8-difluoro-4-methylidene-4,5-dihydro-7H-pyrrolo[3,2,1-de]-1,5-naphthyridin-7-one (631 mg, 2.9 mmol) in tert-butanol/water (30 ml/30 ml) was treated with AD mix alpha (4.3 g) under argon. After 18 hours stirring the reaction mixture was treated with saturated sodium sulphite solution (30 ml). After 10 minutes stirring the mixture was extracted with 20% methanol in dichloromethane (3×300 ml). The organic extracts were dried over magnesium sulphate and evaporated affording a white solid (710 mg, 97%).

MS (+ve ion electrospray) m/z 255 (MH+).

(k) [3,8-difluoro-4-hydroxy-7-oxo-4,5-dihydro-7H-pyrrolo[3,2,1-de]-1,5-naphthyridin-4-yl]methyl 4-methylbenzenesulfonate A solution of 3,8-difluoro-4-hydroxy-4-(hydroxymethyl)-4,5-dihydro-7H-pyrrolo[3,2,1-de]-1,5-naphthyridin-7-one (710 mg, 2.79 mmol) in dichloromethane (35 ml) and tetrahydrofuran (35 ml) was treated with triethylamine (0.58 ml, 4.19 mmol), para-toluenesulphonyl chloride (586 mg, 3.07 mmol) and dibutyltin oxide (35 mg, 0.14 mmol). After 6 hours stirring at room temperature under argon, the mixture was evaporated and water (200 ml) was added. The aqueous phase was extracted with dichloromethane (3×200 ml) and the combined organic extracts dried over magnesium sulphate and evaporated to give the desired compound (1.2 g, 100%) which was used without further purification.

MS (+ve ion electrospray) m/z 409 (MH+).

(l) 1,1-dimethylethyl (1-{[3,8-difluoro-4-hydroxy-7-oxo-4,5-dihydro-7H-pyrrolo[3,2,1-de]-1,5-naphthyridin-4-yl]methyl}-4-piperidinyl)carbamate A solution of crude [3,8-difluoro-4-hydroxy-7-oxo-4,5-dihydro-7H-pyrrolo[3,2,1-de]-1,5-naphthyridin-4-yl]methyl 4-methylbenzenesulfonate (1.2 g, 2.79 mmol) in ethanol (40 mL) was treated with sodium carbonate (889 mg, 8.38 mmol) and 1,1-dimethylethyl 4-piperidinylcarbamate (615 mg, 3.07 mmol). The reaction mixture was stirred at room temperature for 18 hours under argon, evaporated and treated with water (200 mL). The aqueous layer was extracted with a 10% solution of methanol in dichloromethane (3×200 mL) and the combined organic extracts dried over magnesium sulphate and evaporated. The residue was chromatographed eluting with a 0-10% gradient of methanol in dichloromethane affording a yellow solid (1.1 g, 91%).

MS (+ve ion electrospray) m/z 437 (MH+).

(m) (4S)-4-[(4-amino-1-piperidinyl)methyl]-3,8-difluoro-4-hydroxy-4,5-dihydro-7H-pyrrolo[3,2,1-de]-1,5-naphthyridin-7-one To a solution of 1,1-dimethylethyl (1-{[3,8-difluoro-4-hydroxy-7-oxo-4,5-dihydro-7H-pyrrolo[3,2,1-de]-1,5-naphthyridin-4-yl]methyl}-4-piperidinyl)carbamate (1.11 g, 2.5 mmol) in chloroform (20 mL) was added a 4M solution of HCl in 1,4-dioxane (20 mL). The reaction mixture was stirred for 15 min then methanol (20 mL) was added and stirred for 15 min, evaporated and redissolved in water (40 mL). Sodium carbonate (~1 g) was added until basic. The aqueous layer was extracted with a 20% solution of methanol in dichloromethane (4×200 mL). The combined organic extracts were dried over magnesium sulphate and evaporated affording the crude product (864 mg, 100%).

MS (+ve ion electrospray) m/z 337 (MH+).

A portion of this material (740 mg, estimated ratio of E1:E2 ca. 3:1) was resolved by preparative chiral HPLC into the two enantiomers E1 and E2, using a Chiralpak AD column, eluting with 50:50:0.1-CH$_3$CN:isopropylalcohol:isopropylamine affording 553 mg of the desired E1 (4S) enantiomer (>99.5% ee) as the first eluting enantiomer.

(n) Title Compound

Method A

A solution of 4-[(4-amino-1-piperidinyl)methyl]-3,8-difluoro-4-hydroxy-4,5-dihydro-7H-pyrrolo[3,2,1-de]-1,5-naphthyridin-7-one (109 mg, 0.32 mmol) and [1,3]oxathiolo[5,4-c]pyridine-6-carbaldehyde (54 mg, 0.32 mmol) (for a synthesis, see WO2004058144, Example 61) in chloroform/methanol (5 ml/0.5 ml) was stirred for 1 h under argon and then treated with sodium triacetoxyborohydride (206 mg, 0.97 mmol). After 10 min stirring the reaction mixture was treated with saturated sodium bicarbonate (20 mL). The aqueous layer was extracted with a 10% solution of methanol in dichloromethane (3×100 mL). The combined organic extracts were dried over magnesium sulphate and evaporated. The residue was chromatographed eluting with a 0-20% gradient of methanol in dichloromethane affording the free base of the title compound (enantiomeric ratio uncharacterised) as a yellow solid (100 mg, 63%).

δH (CDCl$_3$, 400 MHz) 1.50 (2H, m), 1.93 (2H, m), 2.42-2.60 (4H, m), 2.80-3.00 (3H, m), 3.25 (1H, d), 3.80 (2H, s), 4.40 (2H, s), 5.30 (1H, s), 5.74 (2H, s), 7.17 (1H, s), 7.64 (1H, d), 7.94 (1H, s), 8.41 (1H, s).

MS (+ve ion electrospray) m/z 488 (MH+).

This material was treated with 4M hydrochloric acid in 1,4-dioxane (103 ul, 2 equivalent) to give the title compound (57 mg).

Method B

A solution of (4S)-4-[(4-amino-1-piperidinyl)methyl]-3,8-difluoro-4-hydroxy-4,5-dihydro-7H-pyrrolo[3,2,1-de]-1,5-naphthyridin-7-one (E1 enantiomer) (180 mg, 0.536 mmol) and [1,3]oxathiolo[5,4-c]pyridine-6-carbaldehyde (89 mg, 0.536 mmol) (for a synthesis, see WO2004058144, Example 61) in chloroform/methanol (5 ml/0.5 ml) was stirred at room temperature under argon for 1 h before treatment with sodium triacetoxyborohydride (341 mg, 1.608 mmol). After 1 h stirring the reaction mixture was treated with saturated sodium bicarbonate (20 ml). The aqueous layer was extracted with a 10% solution of methanol in dichloromethane (3×200 ml). The combined organic extracts were dried over magnesium sulphate and evaporated. The residue was chromatographed eluting with a 0-20% gradient of methanol in dichloromethane to yield 82 mg initially and 13 mg by re-chromatographing mixed fractions of the free base of the title compound as a yellow solid (95 mg, 36%).

δH (CDCl$_3$, 400 MHz) 1.44-1.50 (2H, m), 1.87-1.96 (2H, m), 2.42-2.60 (3H, m), 2.80-3.00 (3H, m), 3.25 (1H, d), 3.80 (2H, s), 4.44 (2H, s), 5.30 (1H, s), 5.74 (2H, s), 7.17 (1H, s), 7.64 (1H, d), 7.94 (1H, s), 8.41 (1H, s).

MS (+ve ion electrospray) m/z 488 (MH+).

This material was converted to the title compound by treatment with HCl (yellow solid, 12 mg).

Example 16B

(4S)-3,8-Difluoro-4-hydroxy-4-({4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one hydrochloride (4S)-3,8-Difluoro-4-hydroxy-4-({4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one in methanol was treated with 6N hydrochloric acid (1 equivalent) and then evaporated to afford the hydrochloride salt.

Example 17

(4S)-4-({4-[(6,7-Dihydro-5H-pyrano[2,3-c]py-ridazin-3-ylmethyl)amino]-1-piperidinyl}methyl)-3-fluoro-4-hydroxy-4,5-dihydro-7H-pyrrolo[3,2,1-de]-1,5-naphthyridin-7-one (E1 enantiomer series) dihydrochloride

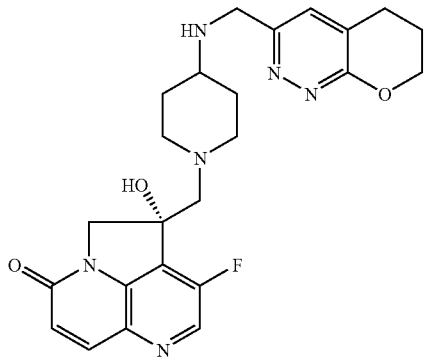

(a) 4-Bromo-2-{[4-(methyloxy)phenyl]methyl}-6-({[4-(methyloxy)phenyl]methyl}oxy)-3(2H)-pyridazinone and 5-bromo-2-{[4-(methyloxy)phenyl]methyl}-6-({[4-(methyloxy)phenyl]methyl}oxy)-3(2H)-pyridazinone A solution of 4-methoxybenzyl alcohol (6.2 ml, 50 mmol) in dry ether (120 ml) was treated dropwise with phosphorus tribromide (2.07 ml, 22 mmol), refluxed for 1 hour, cooled, washed twice with water, dried and the solvent evaporated. The 4-methoxybenzyl bromide thus produced was added to a mixture of 4-bromo-1,2-dihydro-3,6-pyridazinedione (for a preparation, see B. Kasnar et al, Nucleosides & Nucleotides (1994), 13(1-3), 459-79 or Example 30(a)) (4 g, 21 mmol) and potassium carbonate (8.28 g, 60 mmol) in dry DMF (60 ml) and stirred overnight at room temperature. The mixture was diluted with ethyl acetate, washed 3 times with water, dried over magnesium sulfate and evaporated to low volume. Some solid was filtered off and washed with ethyl acetate. The filtrate was evaporated to dryness and the residue chromatographed on silica gel, eluting with 20% ethyl acetate/hexane and then 100% ethyl acetate. This gave the less polar of the 2 desired products (3.233 g), the more polar of the 2 desired products (1.626 g) and a mixture of these (1.351 g). Total yield 6.30 g, 70%.

Less polar product MS (+ve ion electrospray) m/z 431 and 433 (MH$^+$, 15%), 121 (100%).

More polar product MS (+ve ion electrospray) m/z 431 and 433 (MH$^+$, 15%), 121 (100%).

(b) Butyl (2E)-3-[2-{[4-(methyloxy)phenyl]methyl}-6-({[4-(methyloxy)phenyl]methyl}oxy)-3-oxo-2,3-dihydro-4-pyridazinyl]-2-propenoate and butyl (2E)-3-[1-{[4-(methyloxy)phenyl]methyl}-3-({[4-(methyloxy)phenyl]methyl}oxy)-6-oxo-1,6-dihydro-4-pyridazinyl]-2-propenoate Argon was bubbled through a mixture of 4-bromo-2-{[4-(methyloxy)phenyl]methyl}-6-({[4-(methyloxy)phenyl]methyl}oxy)-3(2H)-pyridazinone and 5-bromo-2-{[4-(methyloxy)phenyl]methyl}-6-({[4-(methyloxy)phenyl]methyl}oxy)-3(2H)-pyridazinone (1.35 g, 3.14 mmol) in dry 1,4-dioxane (7.5 ml) for 20 minutes. The solution was then treated with bis(tri-t-butylphosphine)palladium(0) (32 mg, 0.0628 mmol), tris(dibenzylideneacetone)dipalladium(0) (29 mg, 0.0314 mmol), dicyclohexylmethylamine (0.74 ml, 3.45 mmol) and n-butyl acrylate (0.543 ml, 3.78 mmol), stirred under argon at room temperature for 1 hour and heated at 95° C. overnight. The mixture was cooled and partitioned between ethyl acetate and water, separated, and the aqueous re-extracted with ethyl acetate. The combined organic solution was dried and evaporated and the residue chromatographed, eluting with 15% ethyl acetate/hexane and then 35% ethyl acetate/hexane.

Less polar product (butyl (2E)-3-[2-{[4-(methyloxy)phenyl]methyl}-6-({[4-(methyloxy)phenyl]methyl}oxy)-3-oxo-2,3-dihydro-4-pyridazinyl]-2-propenoate) (838 mg, 55%).

MS (+ve ion electrospray) m/z 479 (MH$^+$, 70%), 121 (100%).

More polar product (butyl (2E)-3-[1-{[4-(methyloxy)phenyl]methyl}-3-({[4-(methyloxy)phenyl]methyl}oxy)-6-oxo-1,6-dihydro-4-pyridazinyl]-2-propenoate) (580 mg, 39%).

MS (+ve ion electrospray) m/z 479 (MH$^+$, 70%), 121 (100%).

(c) Butyl 3-(2-{[4-(methyloxy)phenyl]methyl}-3,6-dioxo-1,2,3,6-tetrahydro-4-pyridazinyl)propanoate A solution of butyl (2E)-3-[2-{[4-(methyloxy)phenyl]methyl}-6-({[4-(methyloxy)phenyl]methyl}oxy)-3-oxo-2,3-dihydro-4-pyridazinyl]-2-propenoate (838 mg) in ethanol (15 ml)/1,4-dioxane (10 ml) was treated with 10% Pd/C (400 mg) and stirred under hydrogen at atmospheric pressure and room temperature for 2 hours. The catalyst was filtered off using kieselguhr and the filtrate evaporated and redissolved in 1,4-dioxane and the solution evaporated to dryness to give the product as a colourless oil (0.56 g, 89%).

MS (+ve ion electrospray) m/z 361 (MH$^+$, 60%), 121 (100%).

(d) 5-(3-Hydroxypropyl)-1-{[4-(methyloxy)phenyl]methyl}-1,2-dihydro-3,6-pyridazinedione Butyl 3-(2-{[4-(methyloxy)phenyl]methyl}-3,6-dioxo-1,2,3,6-tetrahydro-4-pyridazinyl)propanoate (0.56 g, 1.56 mmol) was dissolved in dry THF (30 ml). The solution, under argon, was cooled to −30° C., and treated dropwise with a 1M solution of lithium aluminium hydride in THF (1.8 ml, 1.8 mmol), allowed to warm gradually to 0° C. and stirred in an ice bath for 30 minutes. 2M hydrochloric acid was added until the pH was 3 and the mixture was partitioned between water and ethyl acetate. The aqueous was re-extracted with ethyl acetate and the combined organic solution dried and evaporated. Chromatography of the residue, eluting with ethyl acetate, gave the product as a white solid (300 mg, 67%).

MS (+ve ion electrospray) m/z 291 (MH$^+$, 30%), 121 (100%).

(e) 4-(3-Hydroxypropyl)-1,2-dihydro-3,6-pyridazinedione 5-(3-Hydroxypropyl)-1-{[4-(methyloxy)phenyl]methyl}-1,2-dihydro-3,6-pyridazinedione (2.734 g) was treated with anisole (10 ml) and TFA (100 ml) and stirred at 40° C. overnight. The solution was cooled, evaporated to dryness and kept under high vacuum for 30 minutes. The residue was taken up in methanol (150 ml), refluxed for 12 hours, cooled and evaporated. The residue was kept 1 hour under high vacuum, triturated under ether and the solid filtered off. Drying under vacuum gave the product as a solid (1.48 g, 92%).

MS (+ve ion electrospray) m/z 171 (MH$^+$, 100%).

(f) 6,7-Dihydro-2H-pyrano[2,3-c]pyridazin-3(5H)-one

A suspension of 4-(3-hydroxypropyl)-1,2-dihydro-3,6-pyridazinedione (1.48 g, 8.7 mmol) in THF (105 ml) was held in an ultrasound bath for 5 minutes, then cooled under argon in an ice bath. Triphenylphosphine (3.67 g, 14 mmol) was added, followed by diisopropyl azodicarboxylate (2.76 ml, 14 mmol). After 30 minutes the solvent was evaporated and the residue kept under high vacuum overnight. Chromatography, eluting first with 2.5% methanol/dichloromethane until triphenylphosphine oxide was removed and then with 5% methanol/dichloromethane, gave the product as an off-white solid (1.049 g, 79%).

MS (+ve ion electrospray) m/z 153 (MH$^+$, 100%).

(g) Butyl 3-(1-{[4-(methyloxy)phenyl]methyl}-3,6-dioxo-1,2,3,6-tetrahydro-4-pyridazinyl)propanoate A solution of butyl (2E)-3-[1-{[4-(methyloxy)phenyl]methyl}-3-({[4-(methyloxy)phenyl]methyl}oxy)-6-oxo-1,6-dihydro-4-pyridazinyl]-2-propenoate (580 mg) in ethanol (15 ml)/1,4-dioxane (5 ml) was treated with 10% Pd/C (400 mg) and stirred under hydrogen at atmospheric pressure and room temperature for 2 hours. The catalyst was filtered off using kieselguhr and the filtrate evaporated and redissolved in 1,4-dioxane and the solution evaporated to dryness to give the product (0.43 g, 98%).

MS (+ve ion electrospray) m/z 361 (MH$^+$, 50%), 121 (100%).

(h) 4-(3-Hydroxypropyl)-1-{[4-(methyloxy)phenyl]methyl}-1,2-dihydro-3,6-pyridazinedione Butyl 3-(1-{[4-(methyloxy)phenyl]methyl}-3,6-dioxo-1,2,3,6-tetrahydro-4-pyridazinyl)propanoate (0.43 g, 1.19 mmol) was dissolved in dry THF (20 ml). The solution under argon was cooled to −30° C., treated dropwise with a 1M solution of lithium aluminium hydride in THF (1.4 ml, 1.4 mmol), allowed to warm gradually to 0° C. and stirred in an ice bath for 30 minutes. 2M Hydrochloric acid was added until the pH was 3 and the mixture was partitioned between water and ethyl acetate. The aqueous was re-extracted with ethyl acetate and the combined organic solution dried and evaporated. The resulting solid was triturated under ethyl acetate, filtered off, washed with ethyl acetate and dried under vacuum to give the product (241 mg, 70%).

MS (+ve ion electrospray) m/z 291 (MH$^+$, 10%), 121 (100%).

(i) 2-{[4-(Methyloxy)phenyl]methyl}-6,7-dihydro-2H-pyrano[2,3-c]pyridazin-3(5H)-one A suspension of 4-(3-hydroxypropyl)-1-{[4-(methyloxy)phenyl]methyl}-1,2-dihydro-3,6-pyridazinedione (2.624 g, 9.1 mmol) in THF (100 ml) was held in an ultrasound bath for 15 minutes. Triphenylphosphine (3.57 g, 13.6 mmol) was added under argon, the reaction mixture was then cooled to −10° C. and diisopropyl azodicarboxylate (2.68 ml, 13.6 mmol) was added and the mixture allowed to warm gradually to room temperature. After 1 hour the solvent was evaporated. Chromatography on silica gel, eluting first with ethyl acetate to remove byproducts and then with 10% ethanol/ethyl acetate, gave the product (2.55 g) contaminated with a little triphenylphosphine oxide.

MS (+ve ion electrospray) m/z 273 (MH$^+$, 50%), 121 (100%).

(j) 6,7-Dihydro-2H-pyrano[2,3-c]pyridazin-3(5H)-one

2-{[4-(Methyloxy)phenyl]methyl}-6,7-dihydro-2H-pyrano[2,3-c]pyridazin-3(5H)-one (2.75 g, 10.1 mmol) was treated with anisole (10 ml) and TFA (100 ml) and heated at 70° C. for 24 hours. The solution was cooled and evaporated and the residue taken up in 2.5% methanol/dichloromethane. This was applied to a silica gel column, and then elution with this solvent mixture followed by 5% methanol/dichloromethane gave the product as an off white solid (1.36 g, 88%).

MS (+ve ion electrospray) m/z 153 (MH$^+$, 100%).

(k) 6,7-Dihydro-5H-pyrano[2,3-c]pyridazin-3-yl trifluoromethanesulfonate

A solution of 6,7-dihydro-2H-pyrano[2,3-c]pyridazin-3(5H)-one (152 mg, 1 mmol) in DMF (2.5 ml) under argon was ice-cooled, treated with sodium hydride (60 mg of a 60% dispersion in oil, 1.5 mmol) and stirred for 1 hour, allowing to warm to room temperature. N-Phenyl-bis(trifluoromethanesulfonimide) (505 mg, 1.4 mmol) was added and stirring was continued for 2 hours. The mixture was diluted with ethyl acetate, washed with saturated aqueous sodium bicarbonate solution and water (twice), aqueous was reextracted with ethyl acetate and this was in turn washed with water. The combined organics were dried and evaporated. Chromatography on silica gel, eluting with 40% ethyl acetate/hexane, gave the product as a white solid (228 mg, 80%).

MS (+ve ion electrospray) m/z 285 (MH$^+$, 100%).

(l) 3-Ethenyl-6,7-dihydro-5H-pyrano[2,3-c]pyridazine

Argon was bubbled for 15 minutes through a solution of 6,7-dihydro-5H-pyrano[2,3-c]pyridazin-3-yl trifluoromethanesulfonate (228 mg, 0.8 mmol) in 1,2-dimethoxyethane (6.5 ml). Tetrakis(triphenylphosphine)palladium(0) (50 mg, 0.0435 mmol) was added and the solution stirred for 20 minutes under argon. The mixture was then treated with potassium carbonate (111 mg, 0.8 mmol), water (1.9 ml) and 2,4,6-trivinylcyclotriboroxane:pyridine complex (180 mg, 0.75 mmol) (for a preparation of this reagent see F. Kerins and D. F. O'Shea, *J. Org. Chem.* 2002, 67, 4968-4971). After stirring for 2 hours at 80° C., the mixture was cooled and partitioned between dichloromethane and saturated aqueous sodium bicarbonate solution. The layers were separated and the aqueous fraction was extracted twice with 20% methanol/dichloromethane. The combined organic solution was dried, evaporated and the residue chromatographed on silica gel, eluting with ethyl acetate to give product as a white solid (100 mg, 77%).

MS (+ve ion electrospray) m/z 163 (MH$^+$, 100%).

(m) 6,7-Dihydro-5H-pyrano[2,3-c]pyridazine-3-carbaldehyde

A solution of 3-ethenyl-6,7-dihydro-5H-pyrano[2,3-c]pyridazine (100 mg, 0.617 mmol) in 1,4-dioxane (5.5 ml)/water (1.1 ml) was cooled in ice/water and treated with sodium periodate (306 mg, 1.43 mmol) and a 4% aqueous solution of osmium tetroxide (0.55 ml). The mixture was allowed to warm to room temperature after an hour, and after a total of 4.75 hours stirring, the solvent was evaporated. 1,4-Dioxane was added and evaporated, followed by dichloromethane and the mixture briefly held in an ultrasonic bath. The whole mixture was applied to a silica gel column and eluted with ethyl acetate to give product (55 mg, 54%).

MS (+ve ion electrospray) m/z 165 (MH$^+$, 100%).

(n) Title Compound

A solution of (4S)-4-[(4-amino-1-piperidinyl)methyl]-3-fluoro-4-hydroxy-4,5-dihydro-7H-pyrrolo[3,2,1-de]-1,5-naphthyridin-7-one (E1 enantiomer) (40 mg, 0.126 mmol), 6,7-dihydro-5H-pyrano[2,3-c]pyridazine-3-carbaldehyde (25.7 mg, 0.157 mmol) and 3 A molecular sieves in chloroform/methanol (1 mL/1 mL) at 65° C., under argon was stirred for 5 hours then cooled and treated with sodium triacetoxyborohydride (53 mg, 0.25 mmol). After stirring overnight at room temperature, the mixture was filtered through Kieselguhr, washed through with a 1:1 mixture of dichloromethane:methanol, filtered, evaporated and partitioned between bicarbonate and a 20% solution of methanol in dichloromethane. The aqueous layer was extracted twice. The combined organic layers were dried and evaporated. The residue was chromatographed eluting with a mixture of dichloromethane/methanol/NH$_4$OH 95/510.5 affording the free base of the title compound (20 mg, 34%).

δH (CDCl$_3$, 250 MHz) 1.35-1.60 (2H, m), 1.90-2.00 (2H, m), 2.02-2.08 (2H, m), 2.39 (1H, dt, J 11.2 and 2.4 Hz)), 2.50-2.63 (2H, m), 2.82-3.01 (5H, m), 3.26 (1H, d, J=13.6 Hz), 3.98 (2H, s), 4.37-4.45 (4H, m), 6.81 (1H, d, J=10.0 Hz), 7.28 (1H, s), 7.89 (1H, d, J=10.0 Hz), 8.37 (1H, d. J 1.6 Hz).

MS (+ve ion electrospray) m/z 467 (MH+).

This material was dissolved in chloroform/methanol and treated with 1M hydrochloric acid in diethyl ether (2 equivalents), and evaporated to give the title compound as a white solid (30 mg).

Example 18

(4S)-4-({4-[(6,7-Dihydro[1,4]oxathiino[2,3-c]pyridazin-3-ylmethyl)amino]-1-piperidinyl}methyl)-3-fluoro-4-hydroxy-4,5-dihydro-7H-pyrrolo[3,2,1-de]-1,5-naphthyridin -7-one (E1 enantiomer series) dihydrochioride

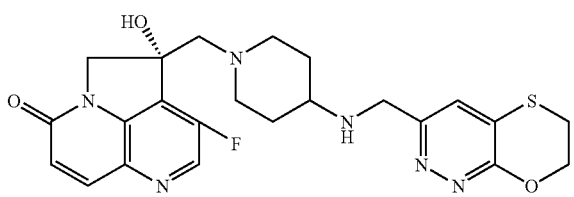

(a) 2-[(3,6-Dichloro-4 pyridazinyl)thio]ethanol

A solution of 3,4,6-trichioropyridazine (25 g) in tetrahydrofuran (200 ml) and triethylamine (19 ml) was treated at 0° C. (ice bath cooling) with 2-mercaptoethanol (8.33 ml) over 5 minutes. After the addition was complete, the mixture was stirred at room temperature for 72 hours. The mixture was stirred with aqueous sodium bicarbonate solution and dichloromethane and the solid was collected, washed with water, ether and pentane and dried in vacuo, giving (22.9 g). The combined aqueous and organic fraction was evaporated to half volume giving further solid, which was washed and dried as above (5.0 g). The total yield of solid (27.9 g; 91%) contained some bromo-analogue (5-10%) by NMR.

(b) 3-Chloro-6,7-dihydro[1,4]oxathiino[2,3-c]pyridazine

A solution of 2-[(3,6-Dichloro-4-pyridazinyl)thio]ethanol (13 g) (previously dried at 50° C. in vacuo) in dry 1,4-dioxane (250 ml) was treated with lithium hydride (3 g) in portions and heated at 105-110° C. for 24 hours. The reaction mixture was cooled and quenched with iced-water. The solution was taken to pH 10-11 with 5M hydrochloric acid and evaporated. Water was added and the mixture was extracted 4× with dichloromethane, dried (sodium sulphate), evaporated, and chromatographed on silica gel, eluting with 0-100% ethyl acetate-hexane, to afford a white solid (1.61 g) (containing ca. 10% of the bromo species).

MS (+ve ion electrospray) m/z 189/91 (Cl MH+); 233/5 (Br MH+).

δH (CDCl3, 400MHz) 3.23 (2H, m), 4.67 (2H, m), 7.26 (1H, s) (for major chloro-compound).

(c) 3-Ethenyl-6,7-dihydro[1,4]oxathiino[2,3-c]pyridazine

A solution of 3-chloro-6,7-dihydro[1,4]oxathiino[2,3-c]pyridazine (1.0 g) in dimethoxyethane (25 ml) was degassed under argon then tetrakis(triphenylphosphine)palladium (0) (135 mg), potassium carbonate (0.695 g), 2,4,6-trivinylcyclotriboroxane pyridine complex (0.8 g) and water (3.7 ml) were added. The mixture was heated at 105° C., overnight. More 2,4,6-trivinylcyclotriboroxane pyridine complex (0.4 g) and tetrakis(triphenylphosphine)palladium (0) (30 mg) were added and heating was continued for 24 hours. The mixture was cooled, treated with aqueous sodium bicarbonate solution, extracted (4×) with DCM, dried (sodium sulphate), evaporated and chromatographed on silica gel (70 g), eluting with 0-100% ethyl acetate-hexane, affording a solid (0.56 g) (87% pure by LC-MS).

MS (+ve ion electrospray) m/z 181 (MH+).

(d) 6,7-Dihydro[1,4]oxathiino[2,3-c]pyridazine-3-carbaldehyde

A solution of 3-ethenyl-6,7-dihydro[1,4]oxathiino[2,3-c] pyridazine (320 mg) in 1,4-dioxane/water (20 ml/5 ml) was treated with an aqueous solution of osmium tetroxide (4% w/v, 2 ml) and sodium periodate (1.08 g), initially stirred in an ice-bath, then allowed to warm to room temperature. After 2.5 hours the mixture was evaporated to dryness and dissolved in 1,4-dioxane and chloroform. Silica gel was added and the mixture was evaporated to dryness, added to a silica column (50 g) and chromatographed, eluting with 0-100% ethyl acetate in hexane, to afford a white solid (116 mg, 36%).

MS (+ve ion electrospray) m/z 183 (MH+).

(e) Title Compound

A solution of (4S)-4-[(4-amino-1-piperidinyl)methyl]-3-fluoro-4-hydroxy-4,5-dihydro-7H-pyrrolo[3,2,1-de]-1,5-naphthyridin-7-one (E1 enantiomer) (50 mg, 0.16 mmol) and 6,7-dihydro[1,4]oxathiino[2,3-c]pyridazine-3-carbaldehyde (32 mg, 0.18 mmol) in N,N-dimethylformamide (2 ml) was stirred for 2.5 hours then treated with sodium triacetoxyborohydride (100 mg). After a further 1.5 hours more aldehyde (8 mg), sodium triacetoxyborohydride (100 mg) and methanol (2 ml) were added. After stirring overnight the mixture was basified with saturated aqueous sodium bicarbonate solution and extracted four times with 10% methanol in dichloromethane. The combined organic extracts were dried and evaporated. The residue was chromatographed on silica eluting with 0-20% methanol in ethyl acetate affording the free base of the title compound (25 mg, 42%).

δH (CDCl$_3$, 250 MHz) 1.35-1.60 (2H, m), 1.85-2.00 (2H, m), 2.38 (1H, t), 2.45-2.65 (3H, m), 2.85-3.05 (3H, m), 3.18-3.25 (2H, m), 3.95 (2H, s), 4.35-4.45 (2H, m), 4.60-4.68 (2H, m), 6.80 (1H, d), 7.30 (1H, s), 7.88 (1H, d), 8.35 (1H, s).

MS (+ve ion electrospray) m/z 485 (MH+).

This material was dissolved in methanol/dichloromethane and treated with 4M hydrochloric acid in 1,4-dioxane followed by trituration of the resulting solid with ether affording the title compound (41 mg).

Example 19

(4S)-4-({4-[(6,7-Dihydro[1,4]oxathiino[3,2-c]pyridazin-3-ylmethyl)amino]-1-piperidinyl}methyl)-3-fluoro-4-hydroxy-4,5-dihydro-7H-pyrrolo[3,2,1-de]-1,5-naphthyridin-7-one (E1 enantiomer series) dihydrochloride

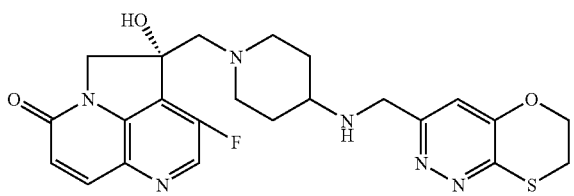

(a) 3-Chloro-6,7-dihydro[1,4]oxathiino[3,2-c]pyridazine

A solution of 2-[(3,6-dichloro-4-pyridazinyl)thio]ethanol (34 g, 0.15 mol) in dry 1,4-dioxane (700 ml) was treated with lithium hydride (1.52 g, 0.18 mol) and heated at reflux overnight. More lithium hydride (1.15 g) was added and the mixture was heated again at reflux overnight. The reaction mixture was cooled, quenched with ice-water and filtered. The filtrate was evaporated to a quarter of its volume. Water was added. The aqueous layer was acidified, extracted 4× with dichloromethane, dried (sodium sulphate), evaporated and chromatographed on silica gel eluting with 0-50% ethyl acetate in dichloromethane affording a yellow solid (170 mg, 0.5%), in the early fractions. Trituration with ethyl acetate-hexane gave the pure product (98 mg).

MS (+ve ion electrospray) m/z 189/91 (MH+).

δH (CDCl$_3$, 400 MHz) 3.29 (2H, m), 4.51 (2H, m), 6.86 (1H, s).

[Later fractions gave the isomeric 3-chloro-6,7-dihydro[1,4]oxathiino[2,3-c]pyridazine (4.2 g)—see Example 18b]

(b) 3-Ethenyl-6,7-dihydro[1,4]oxathiino[3,2-c]pyridazine

A solution of 3-chloro-6,7-dihydro[1,4]oxathiino[3,2-c]pyridazine (450 mg, 2.4 mmol) in dimethoxyethane (12 ml) was treated with tetrakis(triphenylphosphine)palladium (0) (61 mg), potassium carbonate (313 mg), 2,4,6-trivinylcyclotriboroxane pyridine complex (375 mg) and water (1.5 ml). The mixture was heated at 96° C., overnight. The mixture was evaporated to dryness, treated with aqueous sodium bicarbonate solution, extracted (4×) with DCM, dried (sodium sulphate), evaporated and chromatographed on silica gel (50 g), eluting with 1:1 ethyl acetate-hexane, affording a solid (200 mg, 46%), containing slightly impure product.

MS (+ve ion electrospray) m/z 181 (MH+).

(c) 6,7-Dihydro[1,4]oxathiino[3,2-c]pyridazine-3-carbaldehyde

A solution of 3-ethenyl-6,7-dihydro[1,4]oxathiino[3,2-c]pyridazine (200 mg, 1.11 mmol) in 1,4-dioxane/water (10 ml/2 ml) was treated with an aqueous solution of osmium tetroxide (4% w/v, 1 ml) and sodium periodate (0.55 g), initially stirred in an ice-bath for 1.5 hours, then allowed to warm to room temperature. After 1.5 hours the mixture was treated with sodium bicarbonate solution, evaporated to dryness and dissolved in 1,4-dioxane and chloroform. Silica gel was added and the mixture was evaporated to dryness, added to a silica column (20 g), and chromatographed, eluting with 0-100% ethyl acetate in hexane, to afford a pale yellow solid (63 mg, 31%).

MS (+ve ion electrospray) m/z 183 (MH+).

(d) Title Compound

A mixture of (4S)-4-[(4-amino-1-piperidinyl)methyl]-3-fluoro-4-hydroxy-4,5-dihydro-7H-pyrrolo[3,2,1-de]-1,5-naphthyridin-7-one (E1 enantiomer) (46 mg, 0.14 mmol), 6,7-dihydro[1,4]oxathiino[3,2-c]pyridazine-3-carbaldehyde (26 mg, 0.14 mmol) and 3 A molecular sieves in N,N-dimethylformamide (2 ml) was stirred for 4 hours then treated with methanol (4 ml). After a further 3 hours sodium triacetoxyborohydride (92 mg) was added. After stirring overnight the mixture was heated at 65° C. and after 0.5 hours more sodium triacetoxyborohydride (92 mg) was added. The mixture was heated at 65° C. for 4 hours then cooled to room temperature, basified with saturated aqueous sodium bicarbonate solution and extracted four times with 10% methanol in dichloromethane. The combined organic extracts were dried and evaporated. The residue was chromatographed on silica eluting with 0-25% methanol in ethyl acetate affording the free base of the title compound.

δH (CDCl$_3$, 250 MHz) 1.40-1.60 (2H, m), 1.90-2.00 (2H, m), 2.40 (1H, t), 2.50 (1H, t), 2.62 (1H, m), 2.88 (1H, d), 2.90-3.05 (2H, m), 3.22-3.30 (3H, m), 4.00 (2H, s), 4.40 (2H, m), 4.48-4.52 (2H, m), 6.80 (1H, d), 6.88 (1H, s), 7.88 (1H, d), 8.35 (1H, s).

MS (+ve ion electrospray) m/z 485 (MH+).

This material was dissolved in methanol/dichloromethane and treated with 4M hydrochloric acid in 1,4-dioxane followed by trituration of the resulting solid with ether affording the title compound (28 mg).

Examples 20A and 21

(4S)- and (4R)-4-({4-[(2,3-Dihydro[1,4]dioxino[2,3-c]pyridin-7-ylmethyl)amino]-1-piperidinyl}methyl)-3,8-difluoro-4-hydroxy-4,5-dihydro-7H-pyrrolo[3,2,1-de]-1,5-naphthyridin-7-one (E1 and E2 enantiomer series) hydrochloride

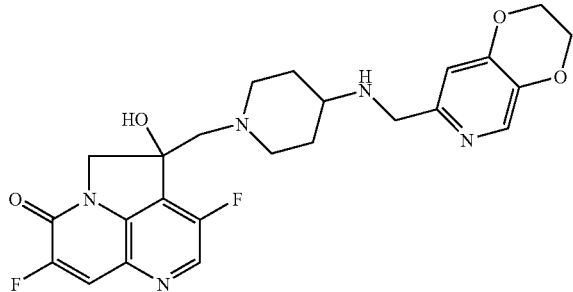

(a) (4R/S)-3,8-Difluoro-4-liydroxy-4-(hydroxymethyl)-4,5-dihydro-7H-pyrrolo[3,2,1-de]-1,5-naphthyridin-7-one A solution of 3,8-difluoro-4-methylidene-4,5-dihydro-7H-pyrrolo[3,2,1-de]-1,5-naphthyridin-7-one (219 mg, 1 mmol) in tert-butanol/water (10 ml/10 ml) was treated with AD mix alpha/beta (0.75 g/0.75 g). After 6 hours the reaction mixture was treated with saturated sodium sulphite solution (10 ml). After 10 minutes the mixture was extracted with 20% methanol in dichloromethane (3×200 ml). The aqueous phase was concentrated (to ca 20 ml) and further extracted with 20% methanol in dichloromethane (3×200 ml). The organic extracts were dried and evaporated affording a white solid (206 mg, 82%).

(b) 1,1-Dimethylethyl (1-{[(4R/S)-3,8-difluoro-4-hydroxy-7-oxo-4,5-dihydro-7H-pyrrolo[3,2,1-de]-1,5-naphthyridin-4-yl]methyl}-4-piperidinyl)(2,3-dihydro[1,4]dioxino[2,3-c]pyridin-7-ylmethyl) carbamate A solution of (4R/S)-3,8-difluoro-4-hydroxy-4-(hydroxymethyl)-4,5-dihydro-7H-pyrrolo[3,2,1-de]-1,5-naphthyridin-7-one (206 mg, 0.811 mmol) in dichloromethane (10 ml), THF (10 ml) and N,N-dimethylformamide (1 ml) was treated with triethylamine (0.17 ml, 1.2 mmol), para-toluenesulphonyl chloride (170 mg, 0.9 mmol) and dibutyltin oxide (10 mg, 0.04 mmol). After 6 hours stirring at room temperature, water (100 ml) was added and the organic phase was separated. The aqueous phase was further extracted with dichloromethane (3×100 ml) and the combined organic extracts dried and evaporated affording an oil (0.42 g). This was dissolved in ethanol (10 ml) then treated with 1,1-dimethylethyl (2,3-dihydro[1,4]dioxino[2,3-c]pyridin-7-ylmethyl)-4-piperidinylcarbamate (284 mg, 0.8 mmol) (see WO2004058144, Example 99(h) for a preparation of this intermediate) and sodium bicarbonate (258 mg, 2.43 mmol). After 18 hours more sodium bicarbonate (258 mg, 2.43 mmol) was added. After a further 24 hours the reaction mixture was diluted with water and extracted with 10% methanol in dichloromethane (3×100 ml). The organic extracts were dried and evaporated. The residue was chromatographed on silica eluting a gradient of 0-10% methanol in dichloromethane affording a yellow oil (400 mg, 84%).

MS (+ve ion electrospray) m/z 586 (MH+).

(c) (4R/S)-4-({4-[(2,3-Dihydro[1,4]dioxino[2,3-c]pyridin-7-ylmethyl)amino]-1-piperidinyl}methyl)-3,8-difluoro-4-hydroxy-4,5-dihydro-7H-pyrrolo[3,2,1-de]-1,5-naphthyridin-7-one dihydrochlioride A solution of 1,1-dimethylethyl (1-{[(4R/S)-3,8-difluoro-4-hydroxy-7-oxo-4,5-dihydro-7H-pyrrolo[3,2,1-de]-1,5-naphthyridin-4-yl]methyl}-4-piperidinyl)(2,3-dihydro[1,4]dioxino[2,3-c]pyridin-7-ylmethyl)carbamate (400 mg, 0.68 mmol) in dichloromethane/methanol (20 ml/5 ml) was treated with hydrochloric acid in 1,4-dioxane (4M, 20 ml). After 0.5 hour the mixture was evaporated. The residue was treated with saturated aqueous sodium bicarbonate solution (50 ml) and extracted three times with 20% methanol in dichloromethane. The combined organic extracts were dried and evaporated. The residue was chromatographed on silica eluting with 0-20% methanol in ethyl acetate affording the free base of the racemic title compound as a yellow solid (214 mg, 65%).

δH (CDCl$_3$, 400 MHz) 1.40-1.65 (2H, m), 1.92-2.00 (2H, m), 2.40 (1H, t), 2.55-2.68 (2H, m), 2.85 (1H, d), 2.95-3.00 (2H, m), 3.30 (1H, d), 3.80 (2H, s), 4.30 (2H, m), 4.35 (2H, m), 4.40 (1H, d), 4.48 (1H, d), 6.82 (1H, s), 7.65 (1H, d), 8.10 (1H, s), 8.45 (1H, s).

MS (+ve ion electrospray) m/z 486 (MH+).

This material was converted to the title racemic dihydrochloride salt (196 mg) by treating a solution of the free base (214 mg) with hydrochloric acid in 1,4-dioxane (4M, 0.22 ml) followed by evaporation.

(d) Title Compounds

A portion of (4R/S)-4-({4-[(2,3-Dihydro[1,4]dioxino[2,3-c]pyridin-7-ylmethyl)amino]-1-piperidinyl}methyl)-3,8-difluoro-4-hydroxy-4,5-dihydro-7H-pyrrolo[3,2,1-de]-1,5-naphthyridin-7-one dihydrochloride (157 mg) was resolved by preparative HPLC into the two enantiomers E1 and E2 using a Chiralpak AD-H column eluting with 0.1:25:75 isopropylamine:isopropanol:acetonitrile affording the E1 enantiomer (Rt 5.6 minutes) then the E2 enantiomer (Rt 12.8 minutes) as free bases (each >98% ee). Each was converted to the title hydrochloride salts E1 (47 mg) and E2 (45 mg) by dissolving in methanol, adding 1 equivalent of aqueous 6.0N HCl and evaporating to dryness.

Example 20B (4S)-4-({4-[(2,3-Dihydro[1,4]dioxino[2,3-c]pyridin-7-ylmethyl)amino]-1-piperidinyl}methyl)-3,8-difluoro-4-hydroxy-4,5-dihydro-7H-pyrrolo[3,2,1-de]-1,5-naphthyridin-7-one (E1 enantiomer series) dihydrochloride (4S)-4-({4-[(2,3-Dihydro[1,4]dioxino[2,3-c]pyridin-7-ylmethyl)amino]1-piperidinyl}methyl)-3,8-difluoro-4-hydroxy-4,5-dihydro-7H-pyrrolo[3,2,1-de]-1,5-naphthyridin-7-one Enantiomer E1 was converted to the dihydrochloride salt by treatment with HCl.

Example 22

(4S)-3-Fluoro-4-hydroxy-4-({4-[(2-quinoxalinylmethyl)amino]-1-piperidinyl}methyl)-4,5-dihydro-7H-pyrrolo[3,2,1-de]-1,5-naphthyridin-7-one (Enantiomer E1) dihydrochloride

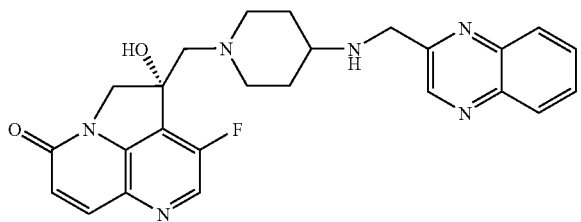

A mixture of (4S)-4-[(4-amino-1-piperidinyl)methyl]-3-fluoro-4-hydroxy-4,5-dihydro-7H-pyrrolo[3,2,1-de]-1,5-naphthyridin-7-one (E1 enantiomer) (80 mg, 0.25 mmol) and 2-quinoxalinecarbaldehyde (30 mg, 0.20 mmol) in dichloromethane/methanol (0.5 mL/0.1 mL) was treated with sodium triacetoxyborohydride (127 mg, 06 mL). After one hour, the reaction mixture was treated with a saturated aqueous solution of sodium bicarbonate (2 mL) and chloroform (1 mL). The mixture was shaken for 5 minutes. The aqueous layer was further extracted with dichloromethane/methanol (1 mL/0.2 mL). The combined organic extracts were added to the top of a column and chromatographed eluting with a 0-30% gradient of methanol/dichloromethane affording the free base of the title compound as a clear oil (30 mg, 33%).

δH (CDCl$_3$, 250 MHz) 1.45-1.73 (2H, m), 1.90-2.10 (2H, m), 2.40 (1H, t), 2.55 (1H, t), 2.70 (1H, m), 2.90 (1H, d), 2.95-3.07 (2H, m), 3.27 (1H, d), 4.25 (2H, s), 4.35 (1H, d), 4.45 (1H, d), 6.85 (1H, d), 7.25-7.32 (2H, m), 7.88 (1H, d), 8.05-8.15 (2H, m), 8.38 (1H, s), 8.90 (1H, s).

MS (+ve ion electrospray) m/z 461 (MH+).

This material was converted to the title dihydrochloride salt (30 mg) by treating a solution of the free base (30 mg) in chloroform (1 mL) with a solution of hydrochloric acid in diethylether (1M, 1 ml) followed by dilution with diethylether (~5 mL), cooling to 0° C. for 5 minutes, centrifugation, decantation of the supernatant and drying the remaining white solid in vacuo.

Example 23A (4S)-4-({4-[(2,3-Dihydro[1,4]oxathiino[3,2-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one (Enantiomer E1) dihydrochloride

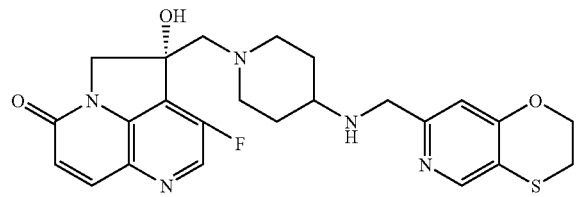

(a) {5-({[4-(Methyloxy)phenyl]methyl}oxy)-4-[(phenylmethyl)oxy]-2-pyridinyl}methyl acetate A solution of triphenylphosphine (39.3 g, 150 mmol) in tetrahydrofuran (600 ml) was treated at 0° C. with bis(1-methylethyl) (E)-1,2-diazenedicarboxylate (30 ml, 152 mmol). After 10 minutes [5-({[4-(methoxy)phenyl]methyl}oxy)-4-oxo-1,4-dihydro-2-pyridinyl]methyl acetate (33.5 g, 110 mmol) (for a synthesis, see WO2004058144, Example 60(c)) was added. After 10 minutes benzyl alcohol (12.4 ml, 120 mmol) was added and the mixture was stirred overnight. Evaporation and chromatography on silica eluting with 20-50% ethyl acetate in hexane afforded an oil (26.3 g, 61%).

MS (+ve ion electrospray) m/z 394 (MH+).

(b) {5-Hydroxy-4-[(phenylmethyl)oxy]-2-pyridinyl}methyl acetate trifluoroacetate salt A solution of {5-({[4-(methyloxy)phenyl]methyl}oxy)-4-[(phenylmethyl)oxy]-2-pyridinyl}methyl acetate (26.3 g, 67 mmol) in dichloromethane (700 ml) was treated with triethylsilane (10 ml, 62.6 mmol) and trifluoroacetic acid (35 ml). After 16 hours the mixture was evaporated and triturated with toluene/ethyl acetate (250 ml/5 ml) affording a white solid that was isolated by filtration and dried in vacuo (22.5 g).

MS (+ve ion electrospray) m/z 274 (MH+).

(c) (4-[(Phenylmethyl)oxy]-5-{[(trifluoromethyl)sulfonyl]oxy}-2-pyridinyl)methyl acetate A solution of 5-hydroxy-4-[(phenylmethyl)oxy]-2-pyridinyl}methyl acetate trifluoroacetate salt (22.5 g) and triethylamine (24 ml) in dichloromethane (700 ml) was treated with 1,1,1-trifluoro-N-phenyl-N-[(trifluoromethyl)sulfonyl]methanesulfonamide (22.8 g). After 4 hours the reaction mixture was washed with water, brine, then dried and evaporated affording an oil. Chromatography on silica gel, eluting with 20-50%% ethyl acetate in petrol afforded a white solid (23.3 g).

MS (+ve ion electrospray) m/z 406 (MH+).

(d) (5-[(1,1-Dimethylethyl)thio]-4-[(phenylmethyl)oxy]-2-pyridinyl}methyl acetate To a solution of (4-[(phenylmethyl)oxy]-5-{[(trifluoromethyl)sulfonyl]oxy}-2-pyridinyl)methyl acetate (12.15 g, 30 mmol) in toluene (500 ml) was added (R)-(+)-2,2'-bis(diphenylphosphino)-1,1'-binaphthyl (1.87 g, 3 mmol). The reaction mixture was purged with argon. Palladium acetate (663 mg, 3 mmol) was added and the mixture was stirred for 10 minutes. 2-Methyl-2-propanethiol sodium salt (4.69, 41.8 mmol) was added and the reaction mixture was flushed again with argon then heated to 80° C. for 7 hours then cooled. The solvent was evaporated. The residue was partitioned between a 1:1 mixture of water and EtOAc. The organic layer was separated and washed with brine, dried over magnesium sulphate and filtered through Kieselguhr. The residue was chromatographed eluting with s 4:1 mixture of hexane:EtOAc affording the product (8.3 g, 80%).

MS (+ve ion electrospray) m/z 346 (MH+).

(e) {5-[(1,1-Dimethylethyl)thio]-4-oxo-1,4-dihydro-2-pyridinyl}methyl acetate A solution of (5-[(1,1-dimethylethyl)thio]-4-[(phenylmethyl)oxy]-2-pyridinyl}methyl acetate (6 g) in 1,4-dioxane/water (100 ml/50 ml) was hydrogenated at atmospheric pressure with 10% palladium on charcol (7 g) overnight. Filtration and evaporation afforded a white solid (4.46 g, 95%).

MS (+ve ion electrospray) m/z 255 (MH+).

(f) 2-(Hydroxymethyl)-5-mercapto-4(1H)-pyridinol hydrochloride salt

A mixture of {5-[(1,1-dimethylethyl)thio]-4-oxo-1,4-dihydro-2-pyridinyl}methyl acetate (240 mg, 0.94 mmol) and concentrated hydrochloric acid (2 ml) was heated to 80° C. overnight. The solvent was evaporated affording a pale yellow solid.

MS (+ve ion electrospray) m/z 158 (MH+).

(g) 2,3-Dihydro[1,4]oxathiino[3,2-c]pyridine-7-carboxaldehyde

A mixture of 2-(hydroxymethyl)-5-mercapto-4(1H)-pyridinol hydrochloride salt (2.0 g), dibromoethane (2.2 ml), potassium carbonate (5.26 g, 38 mmol) in N,N-dimethylformamide (120 ml) was heated to 70° C. overnight. The reaction mixture was then heated to 80° C. for a further 24 hours then cooled. The solvent was evaporated and the residue was partitioned between water and ethyl acetate. The aqueous layer was washed with ethyl acetate (3×) and the combined organic layers were dried over magnesium sulphate then evaporated affording an oil (2.5 g). This material (2.5 g) and manganese dioxide (5 g) in dichloromethane (200 ml) was stirred at room temperature overnight. The mixture was filtered through Kieselguhr, washing with dichloromethane. The filtrate was evaporated and the residue chromatographed eluting with a 50-100% gradient of ethyl acetate in hexane affording a yellow oil. A second chromatographic purification was carried out eluting with a 0-100% gradient of ethyl acetate in hexane affording the desired compound as a white solid (350 mg).

MS (+ve ion electrospray) m/z 182 (MH+).

(h) Title Compound

A solution of (4S)-4-[(4-amino-1-piperidinyl)methyl]-3-fluoro-4-hydroxy-4,5-dihydro-7H-pyrrolo[3,2,1-de]-1,5-naphthyridin-7-one (E1 enantiomer) (225 mg, 0.71 mmol) in methanol/dichloromethane (0.5 ml/5 ml) was treated with 2,3-dihydro[1,4]oxathiino[3,2-c]pyridine-7-carboxaldehyde (129 mg, 0.71 mmol) After 10 minutes, the solution was cooled in an ice-water bath, treated with sodium triacetoxyborohydride (300 mg, 1.42 mmol) and stirred at 0-10° C. for 1 hour. Saturated sodium bicarbonate (10 ml) was added then brine and the aqueous layer was extracted with 10% methanol in dichloromethane (3×30 ml). The combined organic layers were dried over magnesium sulphate, evaporated and chromatographed eluting with a 0-10% gradient of 2M NH₃/methanol in dichloromethane affording the product as a pale yellow solid (250 mg, 58%).

δH (CDCl₃, 400 MHz) 1.40-1.60 (2H, m), 1.70-2.00 (2H, m), 2.35 (1H, dt), 2.55 (2H, m), 2.85 (1H, d), 2.95 (2H, dt), 3.10 (2H, m), 3.25 (1H, d), 3.80 (2H, s), 4.45 (2H, m), 4.50 (2H, m), 6.73 (1H, s), 6.81 (1H, d), 7.88 (1H, d), 8.11 (1H, s), 8.37 (1H, s).

MS (+ve ion electrospray) m/z 484 (MH+).

This material was converted to the title dihydrochloride salt by treating a solution of the free base with a 1M solution of hydrochloric acid in diethylether.

Example 23B (4S)-4-({4-[(2,3-Dihydro[1,4]oxathiino[3,2-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one (Enantiomer E1) hydrochloride (4S)-4-({4-[(2,3-Dihydro[1,4]oxathiino[3,2-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one (Enantiomer E1) was treated with hydrochloric acid (1 equivalent) and then evaporated to afford the hydrochloride salt.

Example 24

(4R/S)-8-Chloro-4-({4-[(2,3-dihydro[1,4]dioxino[2,3-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one dihydrochloride

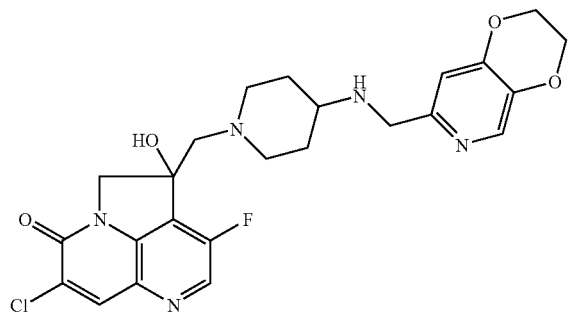

(a) (4R/S)—S-Chloro-3-fluoro-4-hydroxy-4-(hydroxymethyl)-4,5-dihydro-7H-pyrrolo[3,2,1-de]-1,5-naphthyridin-7-one A mixture of (4R/S)-3-fluoro-4-hydroxy-4-(hydroxymethyl)-4,5-dihydro-7H-pyrrolo[3,2,1-de]-1,5-naphthyridin-7-one (1.44 g, 6.1 mmol) and N-chlorosuccinimide (2.04 g, 15.25 mmol) in acetic acid (40 mL) and water (25 mL) was heated at 100° C. for 1 hour. An additional 2.5 equivalent of N-chlorosuccinimide (2.04 g, 15.25 mmol) was added and the reaction mixture was stirred for a further hour, evaporated, treated with an aqueous solution of sodium carbonate (100 mL) and extracted with a 10% solution of methanol in dichloromethane (3×500 mL). The aqueous layer was reduced to ~20 mL and extracted further with a 20% solution of methanol in dichloromethane (3×500 mL). The combined organic layers were dried over magnesium sulphate and evaporated affording the product with extra salts (2.2 g, 130%).

MS (+ve ion electrospray) m/z 271/273 (MH+).

(b) ((4R/S)-8-Chloro-3-fluoro-4-hydroxy-7-oxo-4,5-dihydro-7H-pyrrolo[3,2,1-de]-1,5-naphthyridin-4-yl) methyl 4-methylbenzenesulfonate To a suspension of impure (4R/S)-8-chloro-3-fluoro-4-hydroxy-4-(hydroxymethyl)-4,5-dihydro-7H-pyrrolo[3,2,1-de]-1,5-naphthyridin-7-one (2.20 g, assumed 6.10 mmol) in dichloromethane/tetrahydrofuran/N,N-dimethylformamide (50 mL/50 mL/5 mL) was added para-toluenesulphonyl chloride (1.16 g, 6.10 mmol), dibutyltin oxide (76 mg, 0.31 mmol) and finally triethylamine (1.27 mL, 9.15 mmol). The reaction mixture was stirred at room temperature, under argon, for 3 hours, treated with water (100 mL) and extracted with dichloromethane (3×200 mL). The combined organic layers were dried over magnesium sulphate, evaporated and further dried in vacuo affording the crude product (46%), epoxide (8'-chloro-3'-fluoro-7'H-spiro[oxirane-2,4'-pyrrolo[3,2,1-de][1,5]naphthyridin]-7'-one) (10%) and unknown material (30%).

MS (+ve ion electrospray) m/z 425/427 (MH+).

(c) 1,1-dimethylethyl {1-[((4R/S)-8-chloro-3-fluoro-4-hydroxy-7-oxo-4,5-dihydro-7H-pyrrolo[3,2,1-de]-1,5-naphthyridin-4-yl)methyl]-4-piperidinyl}carbamate To a solution of crude ((4R/S)-8-chloro-3-fluoro-4-hydroxy-7-oxo-4,5-dihydro-7H-pyrrolo[3,2,1-de]-1,5-naphthyridin-4-yl)methyl 4-methylbenzenesulfonate (~2.5 g, assumed 6.10 mmol) in ethanol (50 mL), at room temperature, under argon was added 1,1-dimethylethyl 4-piperidinylcarbamate (1.22 g, 6.10 mmol) and sodium hydrogenocarbonate (1.94 g, 18.31 mmol). The reaction mixture was stirred for 8 hours. A further 0.5 equivalent of 1,1-dimethylethyl 4-piperidinylcarbamate (0.61 g, 3.05 mmol) and 1.5 equivalent of sodium hydrogenocarbonate (0.97 g, 9.15 mmol) were added. The reaction mixture was stirred for an additional 18 hours, treated with water (200 mL) and extracted with a 10% solution of methanol in dichloromethane (3×200 mL). The combined organic layers were dried over magnesium sulphate, evaporated and chromatograped affording an impure material which used crude in the following step.

(d) (4R/S)-4-[(4-amino-1-piperidinyl)methyl]-8-chloro-3-fluoro-4-hydroxy-4,5-dihydro-7H-pyrrolo[3,2,1-de]-1,5-naphthyridin-7-one A solution of crude 1,1-dimethylethyl {1-[((4R/S)-8-chloro-3-fluoro-4-hydroxy-7-oxo-4,5-dihydro-7H-pyrrolo[3,2,1-de]-1,5-naphthyridin-4-yl)methyl]-4-piperidinyl}carbamate (~1 g, 2 mmol) in dichloromethane/methanol (20 mL/20 mL) was treated with a 4M solution of HCl in 1,4-dioxane ((20 mL) was stirred at room temperature, under argon, for 30 min. The reaction mixture was evaporated, dissolved in water (~10 mL), basified by addition of solid sodium carbonate and evaporated. The residue was stirred with a 15% solution of methanol in dichloromethane (3×200 mL). The combined organic layers were dried over magnesium sulphate, evaporated and chromatographed eluting with a gradient of dichloromethane and 2M ammonia/methanol affording the product (215 mg, 27%).

MS (+ve ion electrospray) m/z 353/355 (MH+).

(e) Title Compound

A solution of (4R/S)-4-[(4-amino-1-piperidinyl)methyl]-8-chloro-3-fluoro-4-hydroxy-4,5-dihydro-7H-pyrrolo[3,2,1-de]-1,5-naphthyridin-7-one (118 mg, 0.33 mmol) and 2,3-dihydro[1,4]dioxino[2,3-c]pyridine-7-carboxaldehyde (for a synthesis see WO2004058144, Example 2(c)) (55 mg, 0.33 mmol) in chloroform/methanol (4 mL/0.4 mL) was stirred at room temperature, under argon for 30 min. Sodium triacetoxyborohydride (142 mg, 0.67 mmol) was added and the reaction mixture was stirred for a further 30 min, evaporated and chromatographed eluting with a 0-20% gradient of methanol in dichloromethane affording the monoacetate salt of the free base of the title compound as a yellow oil (129 mg, 77%).

δH (CDCl₃, 400 MHz) 1.50-1.70 (2H, m), 1.90-2.00 (2H, m), 2.02 (3H, s), 2.40 (1H, t), 2.52 (1H, t), 2.65 (1H, m), 2.88 (1H, d), 2.95 (1H, m), 3.03 (1H, m), 3.25 (1H, d), 3.85 (2H, s), 4.25-4.35 (4H, m), 4.40-4.48 (2H, m), 6.82 (1H, s), 8.08 (1H, s), 8.12 (1H, s), 8.40 (1H, s).

MS (+ve ion electrospray) m/z 502/504 (MH+).

This material was converted to the title dihydrochloride salt by treating a solution of the free base in DCM/methanol with 4M hydrochloric acid (2 equivalents).

Example 25

(4R/S)-8-Chloro-3-fluoro-4-hydroxy-4-({4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one dihydrochloride

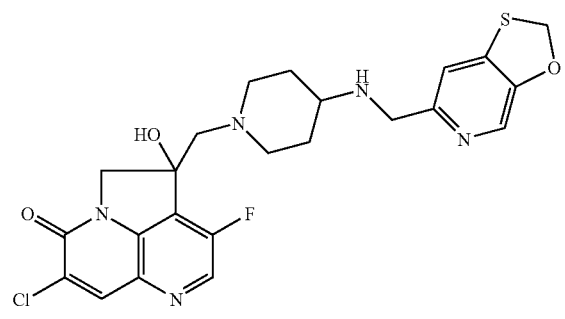

A solution of (4R/S)-4-[(4-amino-1-piperidinyl)methyl]-8-chloro-3-fluoro-4-hydroxy-4,5-dihydro-7H-pyrrolo[3,2,1-de]-1,5-naphthyridin-7-one (97 mg, 0.27 mmol) and [1,3]oxathiolo[5,4-c]pyridine-6-carbaldehyde (46 mg, 0.27 mmol) (for a synthesis, see WO2004058144, Example 61) in chloroform/methanol (4 mL/0.4 mL) was stirred at room temperature, under argon for 30 min. Sodium triacetoxyborohydride (117 mg, 0.55 mmol) was added and the reaction mixture was stirred for a further 30 min, evaporated and chromatographed eluting with a 0-20% gradient of methanol in dichloromethane affording the monoacetate salt of the free base of the title compound (60 mg, 43%).

δH (CDCl₃, 250 MHz) 1.52-1.80 (2H, m), 1.90-2.20 (5H, m), 2.30-2.55 (2H, m), 2.75 (1H, m), 2.88 (1H, d), 2.95 (1H, m), 3.05 (1H, m), 3.25 (1H, d), 3.90 (2H, s), 4.45 (2H, s), 5.28 (2H, s), 7.20 (1H, s), 7.95 (1H, s), 8.13 (1H, s), 8.40 (1H, s).

MS (+ve ion electrospray) m/z 503 (MH+).

This material was converted to the title dihydrochloride salt by treating a solution of the monoacetate salt with hydrochloric acid in dioxin.

Examples 26A and 27

4-({4-[(2,3-Dihydro[1,4]dioxino[2,3-c]pyridin-7-ylmethyl)amino]-1-piperidinyl}methyl)-3,4-difluoro-4,5-dihydro-7H-pyrrolo[3,2,1-de]-1,5-naphthyridin-7-one hydrochloride (E1 and E2 enantiomers)

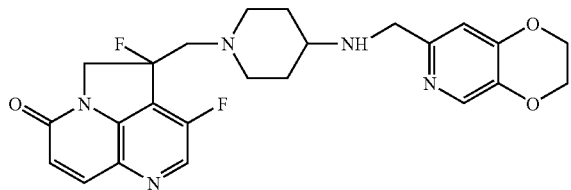

(a) 1,1-Dimethylethyl {1-[((4R/S)-3,4-difluoro-7-oxo-4,5-dihydro-7H-pyrrolo[3,2,1-de]-1,5-naphthyridin-4-yl)methyl]-4-piperidinyl}carbamate A solution of 1,1-dimethylethyl {1-[(3-fluoro-4-hydroxy-7-oxo-4,5-dihydro-7H-pyrrolo[3,2,1-de]-1,5-naphthyridin-4-yl)methyl]-4-piperidinyl}carbamate (15.93 g, 38.1 mmol) in dichloromethane (320 ml) was cooled in an ice bath and treated with (diethylamino)sulphur trifluoride (10.1 ml, 75.9 mmol). After 2.5 hours at room temperature saturated aqueous sodium bicarbonate solution was added, then the phases separated. The aqueous phase was extracted twice more with dichloromethane and the combined organic extracts combined and evaporated. Chromatography eluting with a methanol in dichloromethane gradient afforded the product (5.35 g, 33%).

MS (+ve ion electrospray) m/z 421 (MH+).

(b) (4R/S)-4-[(4-amino-1-piperidinyl)methyl]-3,4-difluoro-4,5-dihydro-7H-pyrrolo[3,2,1-de]-1,5-naphthyridin-7-one dihydrochloride A solution of 1,1-dimethylethyl {1-[((4R/S)-3,4-difluoro-7-oxo-4,5-dihydro-7H-pyrrolo[3,2,1-de]-1,5-naphthyridin-4-yl)methyl]-4-piperidinyl}carbamate (98 mg, 0.23 mmol) in dichloromethane (2 ml) and methanol (1.5 ml), was treated with hydrochloric acid in 1,4-dioxane (4M, 3.5 ml, 14 mmol). After 1.5 hours the mixture was evaporated affording the product (82 mg).

MS (+ve ion electrospray) m/z 321 (MH+).

(c) Title Compounds

A mixture of (4R/S)-4-[(4-amino-1-piperidinyl)methyl]-3,4-difluoro-4,5-dihydro-7H-pyrrolo[3,2,1-de]-1,5-naphthyridin-7-one dihydrochloride (82 mg, 0.21 mmol), 2,3-dihydro[1,4]dioxino[2,3-c]pyridine-7-carboxaldehyde (for a synthesis, see WO2004058144, Example 2(c)) (35 mg, 0.21 mmol), sodium acetate (86 mg, 1.05 mmol) and acetic acid (8 drops) in methanol/chloroform (2.5 ml/2.5 ml) was stirred with 3 A molecular sieves for 1 hour then sodium triacetoxyborohydride (51 mg) was added. After 5 hours saturated aqueous sodium bicarbonate solution was added, then the phases were separated. The aqueous phase was twice extracted with 10% methanol in dichloromethane. The combined organic extracts were dried and evaporated. The residue was chromatographed eluting with 0-10% methanol in dichloromethane affording the racemic free base of the title compounds (70 mg, 71%).

δH (CDCl$_3$, 250 MHz) 1.40-1.60 (2H, m), 1.70 (1H, m), 2.25-2.45 (2H, m), 2.60 (1H, m), 2.78 (1H, m), 2.95 (1H, d), 3.10 (1H, d), 3.35 (1H, t), 3.80 (2H, s), 4.25-4.35 (4H, m), 4.55 (1H, t), 4.68 (1H, d), 4.80 (1H, t), 6.82 (1H, s), 6.88 (1H, d), 7.90 (1H, d), 8.10 (1H, s), 8.45 (1H, s).

MS (+ve ion electrospray) m/z 470 (MH+).

(4R/S)-4-({4-[(2,3-dihydro[1,4]dioxino[2,3-c]pyridin-7-ylmethyl)amino]-1-piperidinyl}methyl)-3,4-difluoro-4,5-dihydro-7H-pyrrolo[3,2,1-de]-1,5-naphthyridin-1-one (43 mg) was resolved by preparative chiral HPLC into the two enantiomers E1 and E2 using a Chiralpak AD-H column, eluting with 50:50:0.1 acetonitrile:methanol:isopropylamine, affording enantiomers E1 (first eluting) and E2 (second eluting) which were converted to the mono hydrochloride salts by dissolving in methanol, adding 1 equivalent of aqueous 6.0N HCl and evaporating to dryness.

E1(HCl salt) net: 15 mg, >99% ee, alpha D+100.6 deg (methanol, 20 deg C., c=1.00).

E2 (HCl salt) net: 18 mg, >99% ee, alpha D −102.0 deg (methanol, 20 deg C., c=1.00).

Example 26B 4-({4-[(2,3-Dihydro[1,4]dioxino[2,3-c]pyridin-7-ylmethyl)amino]-1-piperidinyl}methyl)-3,4-difluoro-4,5-dihydro-7H-pyrrolo[3,2,1-de]-1,5-naphthyridin-7-one dihydrochloride (E1 enantiomer)

A solution of 4-({4-[(2,3-dihydro[1,4]dioxino[2,3-c]pyridin-7-ylmethyl)amino]-1-piperidinyl}methyl)-3,4-difluoro-4,5-dihydro-7H-pyrrolo[3,2,1-de]-1,5-naphthyridin-7-one (E1 enantiomer) was treated with HCl in ether to give the dihydrochloride salt.

Example 28

4-({4-[(6,7-Dihydro[1,4]oxathiino[2,3-c]pyridazin-3-ylmethyl)amino]-1-piperidinyl}methyl)-3,4-difluoro-4,5-dihydro-7H-pyrrolo[3,2,1-de]-1,5-naphthyridin-7-one dihydrochloride (E1 enantiomer)

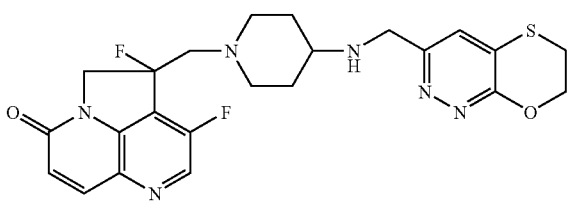

(a) 4-[(4-Amino-1-piperidinyl)methyl]-3,4-difluoro-4,5-dihydro-7H-pyrrolo[3,2,1-de]-1,5-naphthyridin-7-one enantiomers E1 and E2

4.3 g of the free base of (4R/S)-4-[(4-amino-1-piperidinyl)methyl]-3,4-difluoro-4,5-dihydro-7H-pyrrolo[3,2,1-de]-1,5-naphthyridin-7-one dihydrochloride was resolved by preparative chiral HPLC into the two enantiomers E1 and E2 using a Cliralpak AD column, eluting with 50:50:0.1 acetonitrile:methanol:isopropylamine, affording enantiomers E1 (first eluting) and E2 (second eluting).

E1 net: 1.5 g, >99% ee

E2 net: 2.0 g, >99% ee

(b) Title Compound

A solution of 4-[(4-amino-1-piperidinyl)methyl]-3,4-difluoro-4,5-dihydro-7H-pyrrolo[3,2,1-de]-1,5-naphthyridin-7-one E1 enantiomer (60 mg, 0.19 mmol) 6,7-dihydro[1,4]oxathiino[2,3-c]pyridazine-3-carbaldehyde (36 mg, 0.2 mmol) and acetic acid (8 drops) in anhydrous chloroform (2.5 mL) and methanol (2.5 mL), in the presence of 3 A molecular sieves was stirred at room temperature for 1 hour. Sodium cyanoborohydride (50 mg) was added and the reaction mixture was stirred for a further 7.5 hours. Aqueous sodium bicarbonate was added to reach basicity and the phases were separated. The aqueous phase was extracted with a 10% solution of methanol in dichloromethane (3×). The combined organics layers were dried, evaporated and chromatographed on 5 g of silica eluting with a 0-20% gradient of methanol in dichloromethane affording the free base of the title compound (42 mg, 45.5%).

δH (CDCl$_3$, 250 MHz) 1.38 (2H, m), 1.85 (2H, m), 2.36 (2H, m), 2.52 (1H, m), 2.74 (2H, d), 3.00 (1H, t), 3.08 (1H, d), 3.21 (2H, m), 3.350 (1H, t), 3.96 (2H, s), 4.55 (1H, t), 4.65 (2H, m), 4.73 (1H, d), 4.80 (1H, t), 6.88 (1H, d), 7.33 (1H, s), 7.93 (1H, d), 8.43 (1H, s).

MS (+ve ion electrospray) m/z 487 (MH+).

This material was converted to the title dihydrochloride salt (46 mg) by treating a solution of the free base (42 mg) with hydrochloric acid in 1,4-dioxane (0.4M, 0.43 ml) followed by evaporation, trituration with diethyl ether (2×).

Example 29

4-({4-[(6,7-Dihydro[1,4]oxathiino[2,3-e]pyridazin-3-ylmethyl)amino]-1-piperidinyl}methyl)-3,4-difluoro-4,5-dihydro-7H-pyrrolo[3,2,1-de]-1,5-naphthyridin-7-one dihydrochloride (E2 enantiomer)

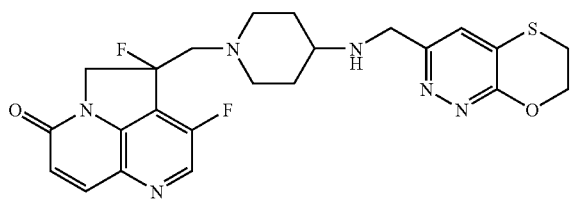

A solution of 4-[(4-amino-1-piperidinyl)methyl]-3,4-difluoro-4,5-dihydro-7H-pyrrolo[3,2,1-de]-1,5-naphthyridin-7-one E2 enantiomer (60 mg, 0.19 mmol), 6,7-dihydro[1,4]oxathiino[2,3-c]pyridazine-3-carbaldehyde (36 mg, 0.2 mmol) and acetic acid (8 drops) in anhydrous chloroform (2.5 mL) and methanol (2.5 mL), in the presence of 3 A molecular sieves was stirred at room temperature for 1 hour. Sodium cyanoborohydride (50 mg) was added and the reaction mixture was stirred for a further 7.5 hours. Aqueous sodium bicarbonate was added to reach basicity and the phases were separated. The aqueous phase was extracted with a 10% solution of methanol in dichloromethane (4×). The combined organics layers were dried, evaporated and chromatographed on 5 g of silica eluting with a 0-20% gradient of methanol in dichloromethane affording the free base of the title compound (32.6 mg, 29%).

δH (CDCl$_3$, 250 MHz) 1.38 (2H, m), 1.85 (2H, m), 2.36 (2H, m), 2.52 (1H, m), 2.74 (2H, d), 3.00 (1H, t), 3.08 (1H, d), 3.21 (2H, m), 3.35 (1H, t), 3.96 (2H, s), 4.55 (1H, t), 4.65 (2H, m), 4.73 (1H, d), 4.80 (1H, t), 6.88 (1H, d), 7.33 (1H, s), 7.93 (1H, d), 8.43 (1H, s).

MS (+ve ion electrospray) m/z 487 (MH+).

This material was converted to the title dihydrochloride salt (26.6 mg) by treating a solution of the free base (32.6 mg) with hydrochloric acid in 1,4-dioxane (0.4M, 0.35 ml) followed by evaporation, trituration with diethyl ether (2×).

Examples 30 and 31

4-({4-[(6,7-Dihydro[1,4]dioxino[2,3-c]pyridazin-3-ylmethyl)amino]-1-piperidinyl}methyl)-3,4-difluoro-4,5-dihydro-7H-pyrrolo[3,2,1-de]-1,5-naphthyridin-7-one monohydrochloride (E1 enantiomer and E2 enantiomer)

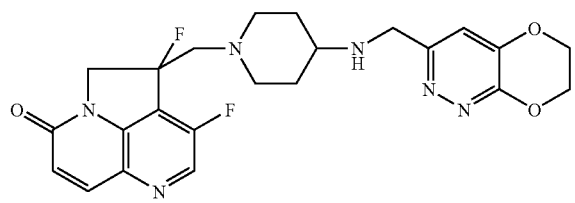

(a) 3,4,6-Trichloropyridazine

This was prepared by a slight variation on the method of Kasnar et al, Nucleosides & Nucleotides (1994), 13(1-3), 459-79.

Hydrazine sulphate salt (51 g) was suspended in water (250 ml), heated to reflux and bromomaleic anhydride (90.38 g) was added dropwise. The mixture was heated at reflux for 4 hours then cooled to room temperature. The reaction was repeated with 29 g hydrazine sulphate, 53 g bromomaleic anhydride and 130 ml water. The precipitates were collected by filtration, washed with water and acetone and dried as a combined batch in vacuo to afford 4-bromo-1,2-dihydro-3,6-pyridazinedione as a white solid (113 g).

The solid in two batches was treated with phosphorus oxychloride (2×200 ml) and heated to reflux for 3.5 hours. The mixture was cooled, evaporated and azeotroped with toluene. The residue was partitioned between dichloromethane and saturated aqueous sodium bicarbonate solution and extracted with DCM twice more. The organic extracts were dried and evaporated. This residue was re-dissolved in dichloromethane, and chromatographed on silica gel (300 g) (DCM as eluent) to give a white solid (101.5 g, 87%).

(LC/MS analysis showed ca 20-30% impurity, isomers of bromo-dichloropyridazine).

MS (+ve ion electrospray) m/z 184/185/186 (MH+), trichloropyridazine.

MS (+ve ion electrospray) m/z 228/229/231 (MH+), bromo-dichloropyridazine.

(b) 2-[(3,6-Dichloro-4-pyridazinyl)oxy]ethanol

A solution of ethylene glycol (55 ml) in tetrahydrofuran (200 ml) was treated at around 0° C. (ice bath cooling) with sodium hydride (60% dispersion in oil, 5.9 g) over 40 minutes. After the addition was complete, 3,4,6-trichloropyridazine (27 g) containing isomers of bromo-dichloropyridazine as impurity was added portionwise and washed in with more dry THF (50 ml) and the mixture was stirred at 0° C. for 1 hour and then at room temperature overnight. The mixture was concentrated (to ⅓ volume) then diluted with aqueous sodium bicarbonate solution and extracted with chloroform (5×) and ethyl acetate (3×). The combined organic extracts were washed with water, dried over sodium sulphate and evaporated and the solids filtered off and washed with CHCl₃ (×3) and dried in a vacuum oven overnight at 40° C. affording a white solid (25.5 g, 83%), containing some bromo-derivative (10-15%).

MS (+ve ion electrospray) m/z 209/211 (MH+).

MS (+ve ion electrospray) m/z 255/7 (MH+), bromo-derivative.

(c) 3-Chloro-6,7-dihydro[1,4]dioxino[2,3-c]pyridazine

A solution of 2-[(3,6-dichloro-4-pyridazinyl)oxy]ethanol containing some bromo-derivative (15.46 g; 0.0703 mol) in dry 1,4-dioxane (1.2 L) was treated with lithium hydride (2.3 g; 0.28 mol) in portions and stirred at room temperature for 1 hour under argon, then heated at 110° C. overnight. The reaction mixture was quenched with wet 1,4-dioxane, then iced-water. The solution was evaporated to half volume, taken to pH 8 with 5M hydrochloric acid and evaporated to dryness. Water was added and the residue was extracted 5× with chloroform, dried (sodium sulphate) and evaporated to afford a white solid (12.4 g, ca. 77%) (containing ca. 15% of a bromo species).

MS (+ve ion electrospray) m/z 173/5 (Cl MH+); 217/9 (Br MH+)

(d) 3-Ethenyl-6,7-dihydro[1,4]dioxino[2,3-c]pyridazine

A solution of 3-chloro-6,7-dihydro[1,4]dioxino[2,3-c]pyridazine (13.6 g, 0.079 mol) containing ca. 15% of a bromo species in dimethoxyethane (400 ml) was degassed under argon for 10 min then tetrakis(triphenylphosphine)palladium (0) (2 g), potassium carbonate (10.33 g), 2,4,6-trivinylcyclotriboroxane pyridine complex (11.32 g) and water (55 ml) were added. The mixture was heated at 95° C. for 48 hours and cooled and evaporated to dryness. The mixture was treated with aqueous sodium bicarbonate solution and extracted (5×) with DCM. Extracts were dried (sodium sulphate), evaporated and the residue chromatographed on silica gel (500 g), eluting with 0-100% ethyl acetate-hexane, affording the product (6.43 g, 50%); [also some impure fractions (1.8 g)].

MS (+ve ion electrospray) m/z 165 (MH+).

(e) 6,7-Dihydro[1,4]dioxino[2,3-c]pyridazine-3-carbaldehyde

A solution of 3-ethenyl-6,7-dihydro[1,4]dioxino[2,3-c]pyridazine (11.58 g) in 1,4-dioxane/water (600 ml/180 ml), cooled in ice, was treated with an aqueous solution of osmium tetroxide (4% w/v, 25 ml) and sodium periodate (43 g). This mixture was allowed to warm to room temperature and after 7 hours under stirring the mixture was evaporated to dryness and azeotroped with 1,4-dioxane. Silica gel, 1,4-dioxane and chloroform were added and the mixture was evaporated to dryness overnight, then added to a silica column (400 g) and chromatographed, eluting with chloroform then 0-100% ethyl acetate in hexane, to afford a white solid (7.55 g, 64%).

MS (+ve ion electrospray) m/z 167 (MH+).

(f) Title Compounds

A solution of (4R/S)-4-[(4-amino-1-piperidinyl)methyl]-3,4-difluoro-4,5-dihydro-7H-pyrrolo[3,2,1-de]-1,5-naphthyridin-7-one (63 mg, 0.20 mmol), 6,7-dihydro[1,4]dioxino[2,3-c]pyridazine-3-carbaldehyde (33 mg, 0.2 mmol) and acetic acid (8 drops) in anhydrous chloroform (2.5 mL) and methanol (2.5 mL), in the presence of 3 A molecular sieves was stirred at room temperature for 1 hour. Sodium cyanoborohydride (50 mg) was added and the reaction mixture was stirred for a further 6 hours. More 6,7-dihydro[1,4]dioxino[2,3-c]pyridazine-3-carbaldehyde (22 mg) and acetic acid (6 drops) were added followed by sodium cyanoborohydride (35 mg) after 30 min of stirring. After a further 6 hours, 6,7-dihydro[1,4]dioxino[2,3-c]pyridazine-3-carbaldehyde (25 mg) was added. The mixture as stirred for 1 hour then sodium cyanoborohydride (35 mg) was added and stirring continued for 7 hours. An aqueous solution of sodium bicarbonate was added to reach basicity and the phases were separated. The aqueous phase was extracted with a 10% solution of methanol in dichloromethane. The combined organics layers were dried, evaporated and chromatographed on 9 g of silica eluting with a 0-10% gradient of methanol in dichloromethane affording the racemic free base of the title compound (36 mg, 389%).

δH (CDCl₃, 250 MHz) 1.44 (2H, m), 1.87 (2H, m), 2.37 (2H, in), 2.53 (1H, m), 2.78 (2H, d), 3.01 (1H, t), 3.10 (1H, d), 3.36 (1H, 7), 3.83 (2H, s), 4.54 (1H, t), 4.63 (2H, m), 4.68 (1H, d), 4.81 (1H, t), 6.84 (1H, d), 6.93 (1H, d), 7.20 (1H, d), 7.92 (1H, d), 8.43 (1H, s).

MS (+ve ion electrospray) m/z 508 (MH+).

This material (36 mg) of the free base of the title compound was resolved by chiral HPLC using a Chiralpak AD-H column, eluting with 50:50:0.1 cetonitrile:methanol: isopropylamine, affording isomers E1 and E2.

E1 net: 9 mg, 100% ee.

E2 net: 8.6 mg, 99% ee.

Each of these materials was converted to the corresponding monohydrochloride salts by dissolving in methanol, adding 1 equivalent of aqueous 6.0NHC1 and evaporating to dryness.

Example 32

3,4-Difluoro-4-[(4-{[(3-oxo-3,4-dihydro-2H-pyrido [3,2-b][1,4]oxazin-6-yl)methyl]amino}-1-piperidinyl)methyl]-4,5-dihydro-7H-pyrrolo[3,2,1-de]-1,5-naphthyridin-7-one dihydrochloride (E1 enantiomer)

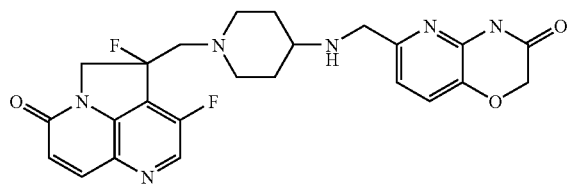

A solution of 4-[(4-amino-1-piperidinyl)methyl]-3,4-difluoro-4,5-dihydro-7H-pyrrolo[3,2,1-de]-1,5-naphthyridin-7-one E1 enantiomer (60 mg, 0.19 mmol), 3-oxo-3,4-dihydro-2H-pyrido[3,2-b][1,4]oxazine-6-carboxaldehyde (for a synthesis, see WO2004058144, Example 1(1)) (36 mg, 0.2 mmol) and acetic acid (8 drops) in anhydrous chloroform (2.5 mL) and methanol (2.5 mL), in the presence of 3 A molecular sieves was stirred at room temperature for 1 hour. Sodium cyanoborohydride (50 mg) was added and the reaction mixture was stirred for a further 8 hours. Aqueous sodium bicarbonate was added to reach basicity and the phases were separated. The aqueous phase was extracted with a 10% solution of methanol in dichloromethane (3×). The combined organics layers were dried, evaporated and chromatographed on 5 g of silica eluting with a 0-20% gradient of methanol in dichloromethane affording the free base of the title compound (65 mg, 71%).

δH (CDCl$_3$, 250 MHz) 1.39 (2H, m), 1.84 (2H, m), 2.35 (2H, m), 2.52 (1H, m), 2.24 (1H, d), 3.00 (1H, t), 3.08 (1H, d), 3.35 (1H, t), 4.00 (2H, s), 4.37 (2H, m), 4.51 (2H, m), 4.55 (1H, t), 4.68 (1H, d), 4.80 (1H, t), 6.88 (1H, d), 7.04 (1H, s), 7.93 (1H, d), 8.43 (1H, s).

MS (+ve ion electrospray) m/z 556 (MH+).

This material was converted to the title dihydrochloride salt (68 mg) by treating a solution of the free base (32.6 mg) with hydrochloric acid in 1,4-dioxane (0.4M, 0.65 ml) followed by evaporation.

Example 33

4-({4-[(6,7-Dihydro-5H-pyrano[2,3-c]pyridazin-3-ylmethyl)amino]-1-piperidinyl}methyl)-3,4-difluoro-4,5-dihydro-7H-pyrrolo[3,2,1-de]-1,5-naphthyridin-7-one dihydrochloride (E1 enantiomer)

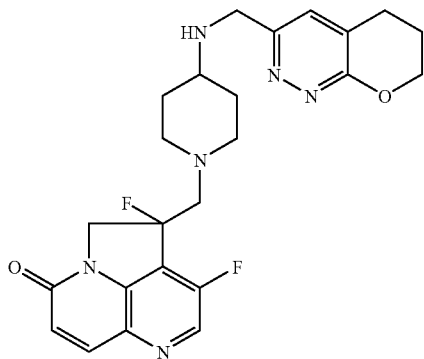

A solution of 4-[(4-amino-1-piperidinyl)methyl]-3,4-difluoro-4,5-dihydro-7H-pyrrolo[3,2,1-de]-1,5-naphthyridin-7-one E1 enantiomer (40 mg, 0.125 mmol) and 6,7-dihydro-5H-pyrano[2,3-c]pyridazine-3-carbaldehyde (25.4 mg, 0.156 mmol) in chloroform (15 mL) and methanol (1 mL), in the presence of 3 A molecular sieves was stirred at 65° C., under argon, for 5 hours. The reaction mixture was cooled down, sodium triacetoxtyborohydride (53 mg, 0.25 mmol) was added and the reaction mixture was stirred for a further 18 hours. The mixture was then filtered through Kieselguhr, washed through with dichloromethane/methanol (1/1), filtered, evaporated and partitioned between sodium bicarbonate and a 20% solution of methanol in dichloromethane (3×). The combined organics layers were dried, evaporated and chromatographed eluting with a dichloromethane/methanol/NH$_4$OH 95/5/0.5 affording the free base of the title compound as a yellow foam (3 mg, 56%).

δH (CDCl$_3$, 250 MHz) 1.30-1.50 (2H, m), 1.86 (2H, broad t), 2.06 (2H, quintet), 2.30-2.43 (2H, m), 2.50-2.60 (1H, m), 2.74 (1H, d), 2.86 (2H, t), 2.97-3.10 (2H, m), 3.35 (1H, t), 4.37 (2H, m), 3.99 (2H, s), 4.44 (2H, t), 4.58 (1H, dd), 4.78 (1H, ddt), 6.88 (1H, d), 7.28 (1H, s), 7.93 (1H, d), 8.43 (1H, s).

MS (+ve ion electrospray) m/z 542 (MH+).

This material was converted to the title dihydrochloride salt (39 mg) by treating the free base (32.6 mg) with a 1M solution of hydrochloric acid in diethylether (0.15 ml) followed by evaporation.

TABLE 1

Examples 34-57 were made from (4S)-4-[(4-amino-1-piperidinyl)methyl]-3-fluoro-4-hydroxy-4,5-dihydro-7H-pyrrolo[3,2,1-de-]-1,5-naphthyridin-7-one (E1 enantiomer) and the specified aldehyde by the general method of Example 1(h), except for Examples 38 and 39 which used the specified alkyl halide under typical alkylation conditions (K$_2$CO$_3$, KI, DMF, 40° C., 1 h).

| Example number | Salt form tested | Structure | Aldehyde/alkyl halide | MS* |
|---|---|---|---|---|
| 34 | hydrochloride | 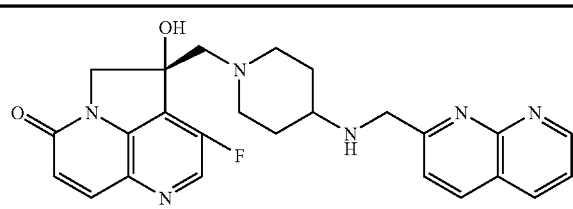 | 1,8-naphthyridine-2-carbaldehyde | 461 |
| 35 | dihydrochloride | 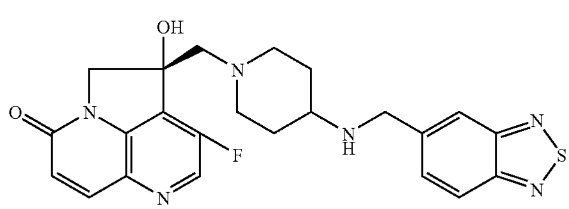 | 2,1,3-benzothiadiazole-5-carbaldehyde | 467 |

TABLE 1-continued

Examples 34-57 were made from (4S)-4-[(4-amino-1-piperidinyl)methyl]-3-fluoro-4-hydroxy-4,5-dihydro-7H-pyrrolo[3,2,1-de-]-1,5-naphthyridin-7-one (E1 enantiomer) and the specified aldehyde by the general method of Example 1(h), except for Examples 38 and 39 which used the specified alkyl halide under typical alkylation conditions (K$_2$CO$_3$, KI, DMF, 40° C., 1 h).

| Example number | Salt form tested | Structure | Aldehyde/alkyl halide | MS* |
|---|---|---|---|---|
| 36 | dihydro-chloride | 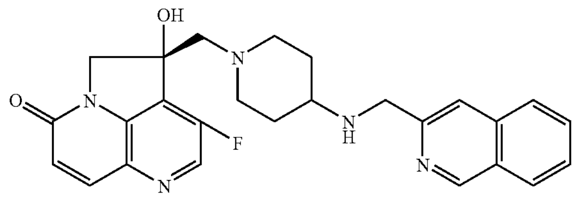 | 3-isoquinoline-carbaldehyde | 460 |
| 37 | dihydro-chloride | 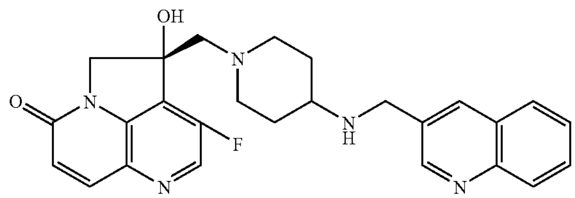 | 3-quinoline-carbaldehyde | 460 |
| 38 | dihydro-chloride | 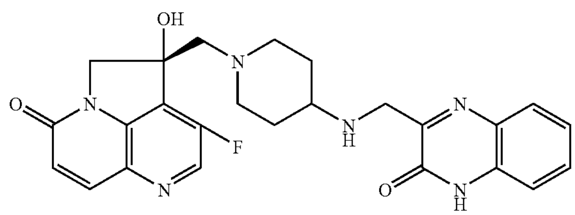 | 3-(bromomethyl)-2(1H)-quinoxalinone | 477 |
| 39 | dihydro-chloride | 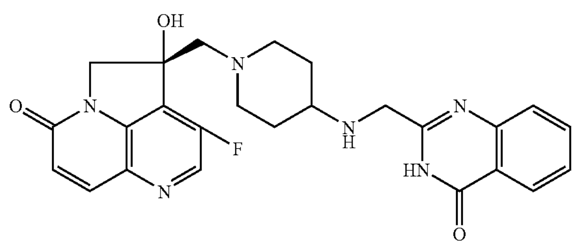 | 2-(chloromethyl)-4(1H)-quinazolinone | 477 |
| 40 | dihydro-chloride | 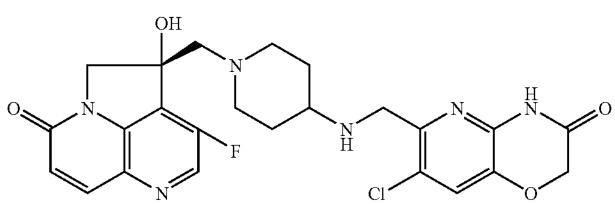 | 7-chloro-3-oxo-3,4-dihydro-2H-pyrido[3,2-b][1,4]oxazine-6-carboxaldehyde (for a synthesis see WO2003064421, Example 15(c)) | 515/517 |
| 41 | dihydro-chloride | 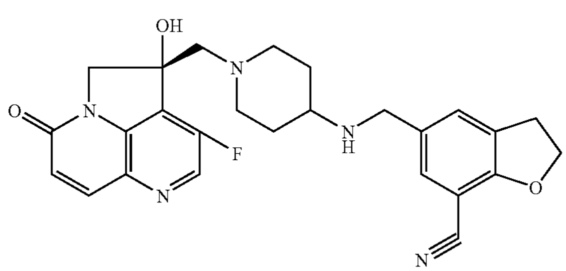 | 5-formyl-2,3-dihydro-1-benzofuran-7-carbonitrile (for a synthesis see Preparation (A) below) | 476 |

TABLE 1-continued

Examples 34-57 were made from (4S)-4-[(4-amino-1-piperidinyl)methyl]-3-fluoro-4-hydroxy-4,5-dihydro-7H-pyrrolo[3,2,1-de-]-1,5-naphthyridin-7-one (E1 enantiomer) and the specified aldehyde by the general method of Example 1(h), except for Examples 38 and 39 which used the specified alkyl halide under typical alkylation conditions ($K_2CO_3$, KI, DMF, 40° C., 1 h).

| Example number | Salt form tested | Structure | Aldehyde/alkyl halide | MS* |
|---|---|---|---|---|
| 42 | dihydrochloride | 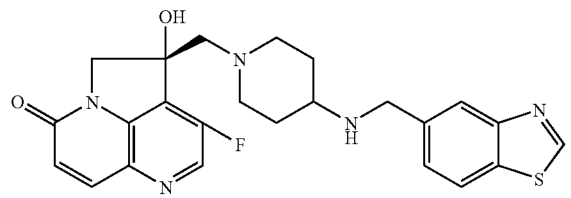 | 1,3-benzothiazole-5-carbaldehyde (for a synthesis see WO2004058144, example 82(c)) | 466 |
| 43 | dihydrochloride | 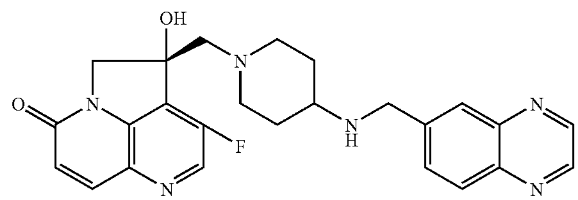 | 6-quinoxaline-carbaldehyde | 461 |
| 44 | monohydrochloride | 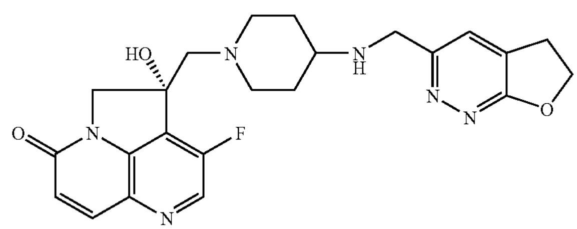 | 5,6-dihydrofuro[2,3-c]pyridazine-3-carbaldehyde (for a synthesis see Preparation (B) below) | 453 |
| 45 | dihydrochloride | 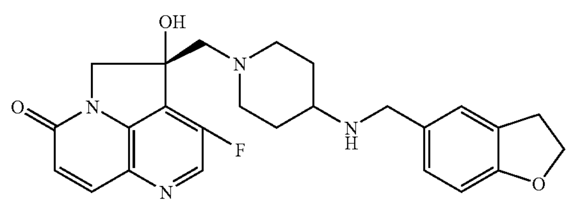 | 2,3-dihydro-1-benzofuran-5-carbaldehyde | 451 |
| 46 | dihydrochloride | 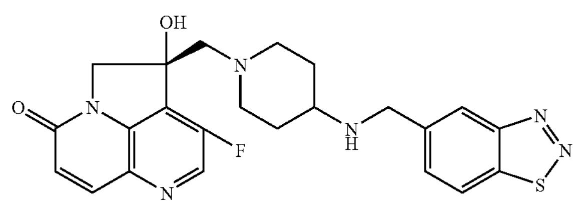 | 1,2,3-benzothiadiazole-5-carbaldehyde (benzo[1,2,3]thiadiazole-5-carboxaldehyde, for a synthesis see WO2003087098, example 152(a)) | 467 |
| 47 | dihydrochloride | 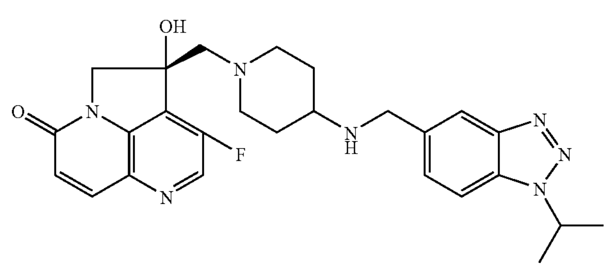 | 1-(1-methylethyl)-1H-1,2,3-benzotriazole-5-carbaldehyde | 492 |

TABLE 1-continued

Examples 34-57 were made from (4S)-4-[(4-amino-1-piperidinyl)methyl]-3-fluoro-4-hydroxy-4,5-dihydro-7H-pyrrolo[3,2,1-de-]-1,5-naphthyridin-7-one (E1 enantiomer) and the specified aldehyde by the general method of Example 1(h), except for Examples 38 and 39 which used the specified alkyl halide under typical alkylation conditions (K$_2$CO$_3$, KI, DMF, 40° C., 1 h).

| Example number | Salt form tested | Structure | Aldehyde/alkyl halide | MS* |
|---|---|---|---|---|
| 48 | dihydro-chloride | 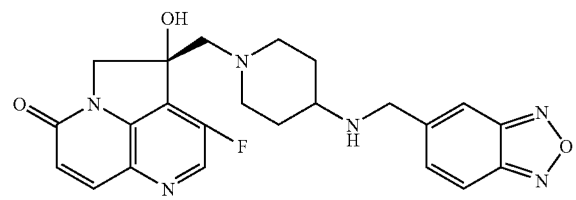 | 2,1,3-benzoxadiazole-5-carbaldehyde | 451 |
| 49 | dihydro-chloride | 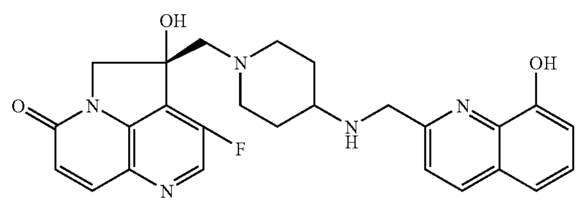 | 8-hydroxy-2-quinolinecarbaldehyde | 476 |
| 50 | dihydro-chloride | 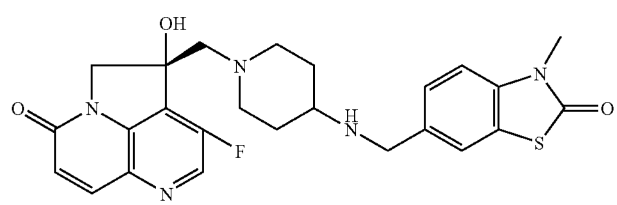 | 3-methyl-2-oxo-2,3-dihydro-1,3-benzothiazole-6-carbaldehyde (prepared from 3-methyl-1,3-benzothiazole-2(3H)-one by formylation with hexamethylene-tetramine and methane sulfonic acid) | 496 |
| 51 | dihydro-chloride | 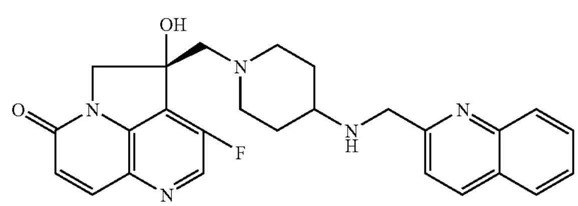 | 2-quinoline-carbaldehyde | |
| 52 | dihydro-chloride | 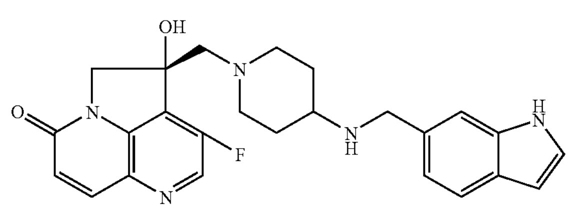 | 1H-indole-6-carbaldehyde | 460 |
| 53 | dihydro-chloride | 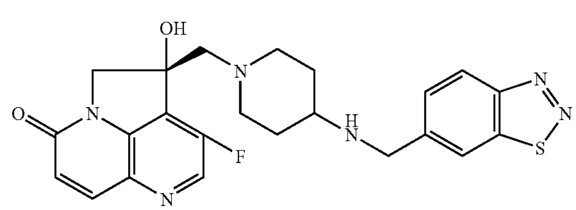 | 1,2,3-benzothiadiazole-6-carbaldehyde (prepared from ethyl 4-aminobenzoate by (a) treatment with S$_2$Cl$_2$, acetic acid followed by treatment with NaNO$_2$, H$_2$SO$_4$ to give ethyl 1,2,3-benzothiadiazole-6-carboxylate, (b) reduction of ethyl 1,2,3-benzothiadiazole-6-carboxylate with lithium aluminium hydride to give 1,2,3-benzothiadiazol-6-ylmethanol, (c) oxidation of 1,2,3-benzothiadiazol-6-ylmethanol with manganese dioxide to give 1,2,3-benzothiadiazole-6-carbaldehyde). | 467 |

TABLE 1-continued

Examples 34-57 were made from (4S)-4-[(4-amino-1-piperidinyl)methyl]-3-fluoro-4-hydroxy-4,5-dihydro-7H-pyrrolo[3,2,1-de-]-1,5-naphthyridin-7-one (E1 enantiomer) and the specified aldehyde by the general method of Example 1(h), except for Examples 38 and 39 which used the specified alkyl halide under typical alkylation conditions (K$_2$CO$_3$, KI, DMF, 40° C., 1 h).

| Example number | Salt form tested | Structure | Aldehyde/alkyl halide | MS* |
|---|---|---|---|---|
| 54 | dihydro-chloride | 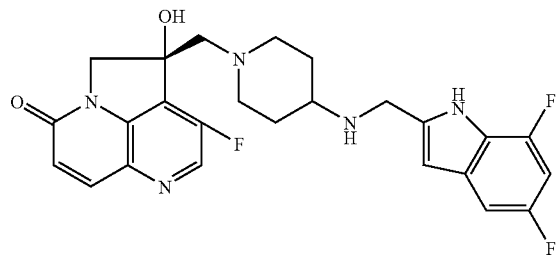 | 5,7-difluoro-1H-indole-2-carbaldehyde (prepared from (2,4-difluorophenyl)hydrazine via (a) treatment with 2-oxopropanoate in acetic acid to give ethyl-2-[(2,4-difluorophenyl) hydrazono]propanoate and then cyclisation with polyphosphoric acid to give ethyl 5,7-difluoro-1H-indole-2-carboxylate, (b) reduction of ethyl 5,7-difluoro-1H-indole-2-carboxylate with lithium aluminium hydride to give (5,7-difluoro-1H-indol-2-yl)methanol, (c) oxidation of (5,7-difluoro-1H-indol-2-yl)methanol with manganese dioxide to give 5,7-difluoro-1H-indole-2-carbaldehyde) | 484 |
| 55 | dihydro-chloride | 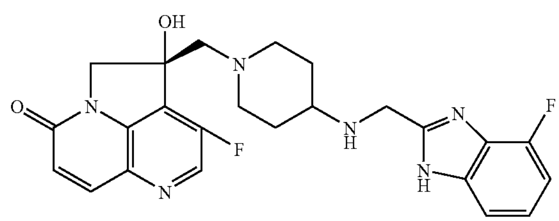 | 4-fluoro-1H-benzimidazole-2-carboxaldehyde (for a synthesis see WO2003087098, Example 320) | 467 |
| 56 | dihydro-chloride | 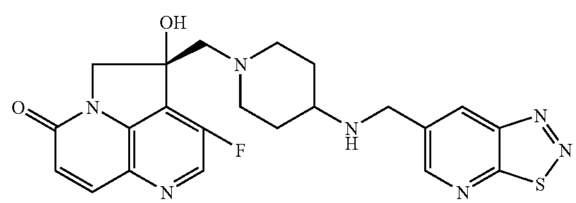 | [1,2,3]thiadiazolo[5,4-b]pyridin-6-ylcarboxaldehyde (for a synthesis see WO2003064431, Example 1(b)) | 468 |
| 57 | fumarate | 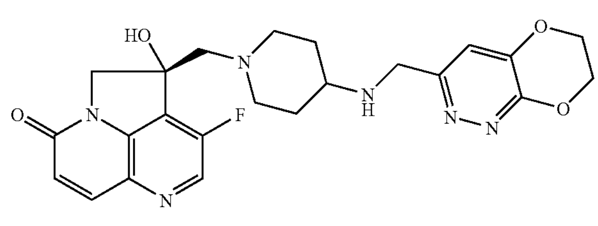 | 6,7-dihydro[1,4]dioxino[2,3-c]pyridazine-3-carbaldehyde | 469 |

*(+ve ion electrospray) m/z (MH+).

TABLE 2

Examples 58-64 were made from the specified tosylate, cyclic amine and aldehyde the general methods of Example 1(f)-(h). Examples 65-68 were made from the specified amine and aldehyde by the general method of Example 1(h).

| Example number | Salt form tested | Structure | Starting materials | MS* |
|---|---|---|---|---|
| 58 | dihydro-chloride | 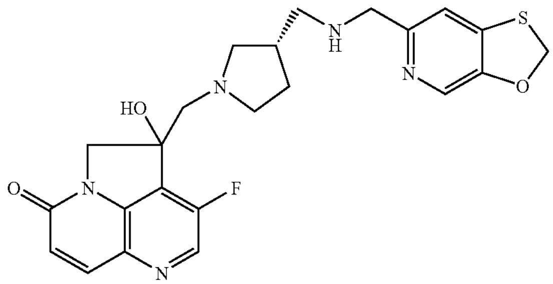 | [(4R/S)-3-fluoro-4-hydroxy-7-oxo-4,5-dihydro-7H-pyrrolo[3,2,1-de]-1,5-naphthyridin-4-yl]methyl 4-methylbenzene-sulfonate 2,2,2-trifluoro-N-[(3R)-3-pyrrolidinylmethyl]acetamide hydrochloride (for a synthesis of the free base, see WO2006002047, Example 1(b)) [1,3]oxathiolo[5,4-c]pyridine-6-carbaldehyde (for a synthesis see WO2004058144, Example 61) | 470 |
| 59 | dihydro-chloride | 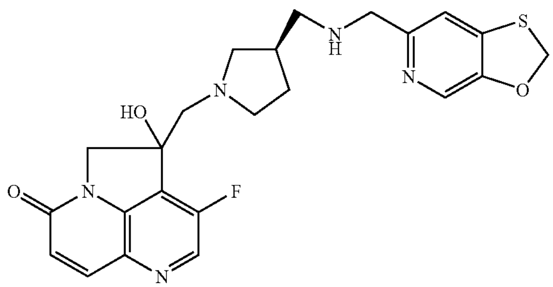 | [(4R/S)-3-fluoro-4-hydroxy-7-oxo-4,5-dihydro-7H-pyrrolo[3,2,1-de]-1,5-naphthyridin-4-yl]methyl 4-methyl-benzenesulfonate 2,2,2-trifluoro-N-[(3S)-3-pyrrolidinylmethyl]-acetamide hydrochloride (may be prepared analogously to its 3R enantiomer, for a synthesis of the free base, see WO2006002047, Example 1(b)) [1,3]oxathiolo[5,4-c]pyridine-6-carbaldehyde (for a synthesis see WO2004058144, Example 61) | 470 |
| 60 | Free base | 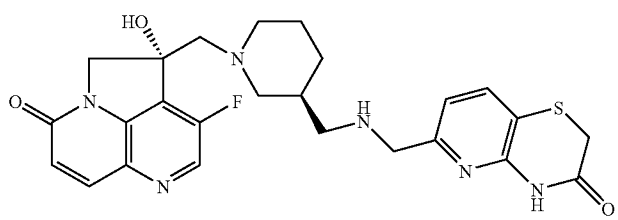 | 3-fluoro-4-hydroxy-7-oxo-4,5-dihydro-7H-pyrrolo[3,2,1-de]-1,5-naphthyridin-4-yl 4-methylbenzene-sulfonate (approximately 3:1 4S:4R) phenylmethyl [(3R)-3-piperidinylmethyl]-carbamate (for a synthesis see Preparation (C) below) 3-oxo-3,4-dihydro-2H-pyrido[3,2-b][1,4]thiazine-6-carboxaldehyde (for a synthesis, see WO2004058144, Example 7(d)) | 511 |
| 61 | free base | 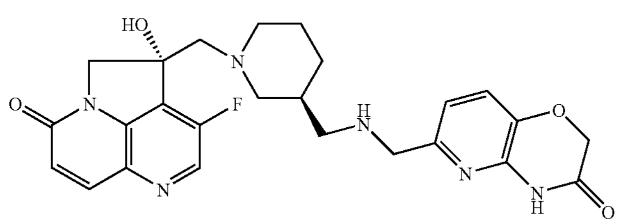 | 3-fluoro-4-hydroxy-7-oxo-4,5-dihydro-7H-pyrrolo[3,2,1-de]-1,5-naphthyridin-4-yl 4-methylbenzene-sulfonate (approximately 3:1 4S:4R) phenylmethyl [(3R)-3-piperidinylmethyl]carbamate (for a synthesis see Preparation (C) below) 3-oxo-3,4-dihydro-2H-pyrido[3,2-b][1,4]oxazine-6-carboxaldehyde (for a synthesis see WO2003087098, Example 31(e)) | 495 |
| 62 | free base | 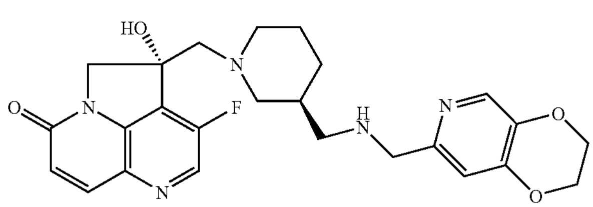 | 3-fluoro-4-hydroxy-7-oxo-4,5-dihydro-7H-pyrrolo[3,2,1-de]-1,5-naphthyridin-4-yl 4-methylbenzene-sulfonate (approximately 3:1 4S:4R) phenylmethyl [(3R)-3-piperidinylmethyl]carbamate (for a synthesis see Preparation (C) below) 2,3-dihydro[1,4]dioxino[2,3-c]pyridine-7-carboxaldehyde (for a synthesis see WO2004058144, Example 2(c)) | 482 |

TABLE 2-continued

*Examples 58-64 were made from the specified tosylate, cyclic amine and aldehyde the general methods of Example 1(f)-(h). Examples 65-68 were made from the specified amine and aldehyde by the general method of Example 1(h).*

| Example number | Salt form tested | Structure | Starting materials | MS* |
|---|---|---|---|---|
| 63 | free base | 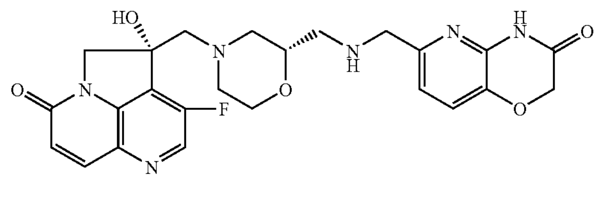 | 3-fluoro-4-hydroxy-7-oxo-4,5-dihydro-7H-pyrrolo[3,2,1-de]-1,5-naphthyridin-4-yl 4-methylbenzene-sulfonate (approximately 3:1 4S:4R) 1,1-dimethylethyl [(2R)-2-morpholinyl-methyl]carbamate (for a synthesis see Preparation (D) below) 3-oxo-3,4-dihydro-2H-pyrido[3,2-b][1,4]oxazine-6-carboxaldehyde (for a synthesis see WO2003087098, Example 31(e)) | 497 |
| 64 | free base | 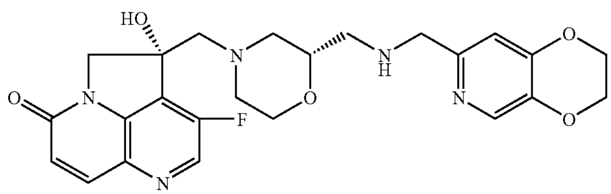 | 3-fluoro-4-hydroxy-7-oxo-4,5-dihydro-7H-pyrrolo[3,2,1-de]-1,5-naphthyridin-4-yl 4-methylbenzene-sulfonate (approximately 3:1 4S:4R) 1,1-dimethylethyl [(2R)-2-morpholinylmethyl]carbamate (for a synthesis see Preparation (D) below) 2,3-dihydro[1,4]dioxino[2,3-c]pyridine-7-carboxaldehyde (for a synthesis see WO2004058144, Example 2(c)) | 484 |
| 65 | dihydro-chloride | 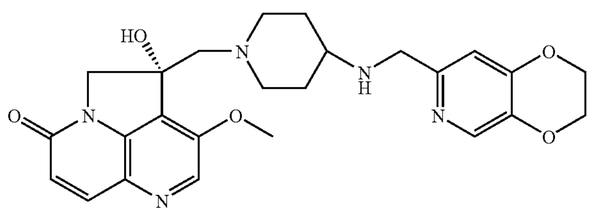 | (4S)-4-[(4-amino-1-piperidinyl)methyl]-4-hydroxy-3-(methyloxy)-4,5-dihydro-7H-pyrrolo[3,2,1-de]-1,5-naphthyridin-7-one (for a synthesis see Preparation (E) below) 2,3-dihydro[1,4]dioxino[2,3-c]pyridine-7-carboxaldehyde (for a synthesis see WO2004058144, Example 2(c)) | 480 |
| 66 | dihydro-chloride | 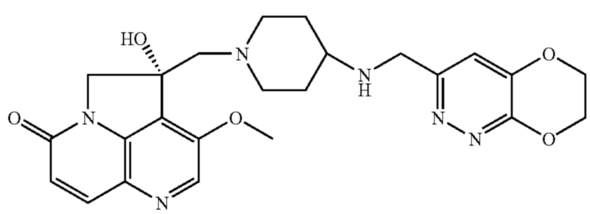 | (4S)-4-[(4-amino-1-piperidinyl)methyl]-4-hydroxy-3-(methyloxy)-4,5-dihydro-7H-pyrrolo[3,2,1-de]-1,5-naphthyridin-7-one (for a synthesis see Preparation (E) below) 6,7-dihydro[1,4]dioxino[2,3-c]pyridazine-3-carbaldehyde | 481 |
| 67 | dihydro-chloride | 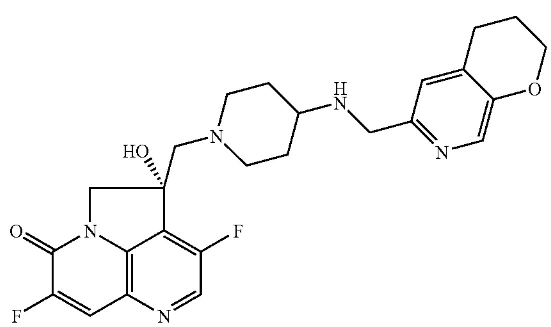 | (4S)-4-[(4-amino-1-piperidinyl)methyl]-3,8-difluoro-4-hydroxy-4,5-dihydro-7H-pyrrolo[3,2,1-de]-1,5-naphthyridin-7-one 3,4-dihydro-2H-pyrano[2,3-c]pyridine-6-carbaldehyde (for a synthesis see WO2004058144, Example 126(e)) | 484 |

TABLE 2-continued

Examples 58-64 were made from the specified tosylate, cyclic amine and aldehyde the general methods of Example 1(f)-(h). Examples 65-68 were made from the specified amine and aldehyde by the general method of Example 1(h).

| Example number | Salt form tested | Structure | Starting materials | MS* |
|---|---|---|---|---|
| 68 | dihydro-chloride | (structure shown) | (4S)-4-[(4-amino-1-piperidinyl)methyl]-3,8-difluoro-4-hydroxy-4,5-dihydro-7H-pyrrolo[3,2,1-de]-1,5-naphthyridin-7-one 2,3-dihydro[1,4]oxathiino[2,3-c]pyridine-7-carbaldehyde (for a synthesis see WO2004058144, Example 60) | 502 |

*(+ve ion electrospray) m/z (MH+).

Preparation (A)
5-formyl-2,3-dihydro-1-benzofuran-7-carbonitrile

(a) 7-bromo-2,3-dihydro-1-benzofuran-5-carbaldehyde

To a solution of 2,3-dihydro-1-benzofuran-5-carbaldehyde (1.0 g, 6.75 mmol) in glacial acetic acid (8 ml) was added sodium acetate (664 mg, 8.1 mmol) and bromine (0.7 ml, 13.5 mmol) at 10° C. slowly. The reaction was stirred for 2 h at room temperature. The reaction was diluted with a saturated aqueous solution of sodium thiosulfate (10 ml), washed with a saturated aqueous solution of sodium bicarbonate, and then extracted with ethyl acetate. Organics were combined, dried over sodium sulfate and dried in vacuo to give the desired compound (1.4 g, 91%).

MS (+ve ion electrospray): m/z 227 (M+H)$^+$.

(b) Title Compound

To a solution of 7-bromo-2,3-dihydro-1-benzofuran-5-carbaldehyde (1.3 g, 4.7 mmol) in dimethylacetamide (2 mL) was added copper(I) cyanide (0.41 g g, 4.7 mmol). The reaction was refluxed for 18 h, and then concentrated under reduced pressure. The residue was washed well with warm ethyl acetate. The combined ethyl acetate layer were concentrated and dried. The crude product was purified by flash column chromatography (silica gel, 4:1 and 2:1 hexane:ethyl acetate gradient) to afford the desired product (0.5 g, 50%).

MS (+ve ion electrospray): m/z 174 (M+H)$^+$.

Preparation (B)
5,6-Dihydrofuro[2,3-c]pyridazine-3-carbaldehyde

(a) (3,6-Dioxo-1,2,3,6-tetrahydro-4-pyridazinyl)acetic acid

A mixture of (2,5-dioxo-2,5-dihydro-3-furanyl)acetic acid (9 g) and hydrazine sulphate (7.2 g) in water was heated to reflux for 4 hours then allowed to cool to ambient temperature. The precipitate was filtered, washing with water then acetone. Drying in vacuo afforded a white solid (8.04 g, 82%).

MS (ES+) m/z 171 (MH+).

(b) Methyl (3,6-dioxo-1,2,3,6-tetrahydro-4-pyridazinyl)acetate

A mixture of (3,6-dioxo-1,2,3,6-tetrahydro-4-pyridazinyl) acetic acid, (5.0 g), methanol (75 ml) and 4M hydrochloric acid in 1,4-dioxane (20 ml) was stirred overnight. Evaporation afforded a white solid.

MS (ES+) m/z 185 (MH+).

(c) 4-(2-Hydroxyethyl)-1,2-dihydro-3,6-pyridazinedione

A suspension of methyl (3,6-dioxo-1,2,3,6-tetrahydro-4-pyridazinyl)acetate (11.1 g, 60.3 mmol) in THF (2 litres) was sonicated to give a fine dispersion. The mixture was called to −15° C. and treated dropwise with a solution of lithium aluminium hydride in THF (1M; 90 ml, 90 mmol). The mixture was stirred at 0° C. for 2 hours. Sodium hydroxide (2M; 15 ml, 30 mmol) was added, then the mixture was acidified with 5M hydrochloric acid to around pH4-5. The supernatant was decanted off and discarded. The oily residue was extracted with water/methanol (500 ml/1 litre). This extract was decanted from the remaining residue, treated with silica and evaporated. The silica residue was added to the top of a column, eluting with 10-30% methanol in DCM affording a pale yellow oil (2.7 g).

MS (ES+) m/z 157 (MH+).

(d) 5,6-Dihydrofuro[2,3-c]pyridazin-3(2H)-one

A mixture of 4-(2-hydroxyethyl)-1,2-dihydro-3,6-pyridazinedione (2.7 g) in THF (200 ml) was treated with triphenylphosphine (6.6 g) and bis(1-methylethyl) (E)-1,2-diazenedicarboxylate (5.0 ml) was warmed to 40° C. After 3 hours the mixture was evaporated and chromatographed onto silica which was added to the top of a column. Chromatography eluting with 0-10% methanol in DCM afforded impure product (420 mg) which was further purified by chromatography in a similar manner affording the product (390 mg).

MS (ES+) m/z 139 (MH+).

(e) 5,6-Dihydrofuro[2,3-c]pyridazin-3-yl trifluoromethanesulfonate

A solution of 5,6-dihydrofuro[2,3-c]pyridazin-3(2H)-one (780 mg) in DMF (15 ml) was treated with sodium hydride (435 mg) then after 2 hours with N-phenyltrifluoromethanesulphonimide (3.62 g). After 2 hours the mixture was diluted with ethyl acetate and washed with saturated aqueous sodium bicarbonate solution. The aqueous phase was further extracted (twice) with ethyl acetate and the combined organic extracts dried and evaporated affording the product (937 mg).
MS (ES+) m/z 271 (MH+).

(f) 3-Ethenyl-5,6-dihydrofuro[2,3-c]pyridazine

A solution of 5,6-dihydrofuro[2,3-c]pyridazin-3-yl trifluoromethanesulfonate (500 mg, 1.85 mmol) in dimethoxyethane (20 ml) was degassed then treated with tetrakis(triphenylphosphine)palladium (0) (116 mg), potassium carbonate (257 mg), 2,4,6-trivinylcyclotriboroxane pyridine complex (for a preparation of this reagent see F. Kerins and D. F. O'Shea, J. Org. Chem. 2002, 67, 4968-4971) (416 mg) and water (3.6 ml). The mixture was stirred at 80° C. for 2 hours then partitioned between DCM and saturated aqueous sodium bicarbonate solution. The aqueous phase was extracted with 10% methanol in DCM then the combined organic extracts dried and evaporated. The residue was chromatographed eluting with ethyl acetate affording a white solid (111 mg, 36%).
MS (ES+) m/z 149 (MH+).

(g) Title Compound

A mixture of 3-ethenyl-5,6-dihydrofuro[2,3-c]pyridazine (110 mg, 0.74 mmol), 4% osmium tetroxide in water (0.66 ml), sodium periodate (367 mg), 1,4-dioxane (6.6 ml) and water (1.3 ml) was stirred for 3 hours. The mixture was evaporated and the residue treated with chloroform and added to the top of a column. Elution with ethyl acetate afforded the product (23 mg).
MS (ES+) m/z 151 (MH+).

Preparation (C) Phenylmethyl [(3R)-3-piperidinylmethyl]carbamate

(a) 1,1-Dimethylethyl (3S)-3-[({[(phenylmethyl)oxy]carbonyl}amino)methyl]-1-piperidinecarboxylate To a solution of 1,1-dimethylethyl (3S)-3-(aminomethyl)-1-piperidinecarboxylate (2.0 g, 9.33 mmol) in DCM (12 ml) at 0° C. were added triethylamine (1.7 ml, 12.1 mmol) followed by N-(benzyloxycarbonyloxy)succinimide (2.56 g, 10.3 mmol). After a few minutes the cooling bath was removed and the reaction was stirred at room temperature for 2 h. The reaction was diluted with ethyl acetate and washed with water (2×), 1N HCl, saturated aq. NaHCO$_3$, brine, dried (Na$_2$SO$_4$) and concentrated. The product was purified on silica gel eluting with 10% ethyl acetate-DCM to give 3.48 g of material containing a small amount of N-(benzyloxycarbonyloxy)succinimide which was used directly in next step.
LC/MS (ES) m/e 349 (M+H)$^+$.

(b) Title Compound 1,1-Dimethylethyl (3S)-3-[({[(phenylmethyl)oxy]carbonyl}amino)methyl]-1-piperidinecarboxylate (~9.3 mmol) was dissolved in DCM (25 mL) and treated with a 4M HCl solution in 1,4-dioxane (24 mL, 96 mmol). The reaction was stirred at room temperature for 3 h, at which time LC/MS indicated that all starting material was consumed. The reaction was concentrated in vacuo to give a thick gum. This material was dissolved in water and extracted with ethyl acetate. The aqueous phase was separated and treated with solid Na$_2$CO$_3$ to bring the pH to ~10. The product was then extracted into CHCl$_3$ (3×) and the combined organic phases were dried (Na$_2$SO$_4$) and concentrated to yield the desired product as an orange oil (2.3 g, 100% for two steps).
LC/MS (ES) m/e 249 (M+H)$^+$.

Preparation (D) 1,1-Dimethylethyl [(2R)-2-morpholinylmethyl]carbamate

(a) Racemic 2-{[(2R,S)-4-(phenylmethyl)-2-morpholinyl]methyl}-1H-isoindole-1,3(2H)-dione To a solution of 4-benzyl-2-(chloromethyl)morpholine (2.0 g, 8.86 mmol) in DMF (10 mL) was added potassium phthalimide (1.96 g, 10.6 mmol) and the mixture was heated at 165° C. for 4 h. Upon cooling, the reaction mixture was poured into water (20 mL) and the product was extracted into CHCl$_3$ (3×) and the combined organic layers were washed with a small amount of water, brine, and dried (Na$_2$SO$_4$). Evaporation of the solvent gave a light tan solid which was used directly in next step.
LC/MS (ES) m/e 337 (M+H)$^+$.

(b) Racemic {[(2R,S)-4-(phenylmethyl)-2-morpholinyl]methyl}amine

Crude racemic 2-{[(2R,S)-4-(phenylmethyl)-2-morpholinyl]methyl}-1H-isoindole-1,3(2R)-dione (~8.8 mmol) was suspended in absolute ethanol (15 mL) and treated with hydrazine monohydrate (0.75 mL, 15.4 mmol). The reaction mixture was heated to reflux during which time the reaction solution turned yellow and homogeneous followed by precipitation of a white solid. After 2 h, the reaction was cooled to room temperature, diluted with CHCl$_3$, and the solids were filtered off. The filtrate was evaporated and the residue was taken up in CHCl$_3$ and washed with a small amount of water, brine, and dried (Na$_2$SO$_4$). Evaporation of the solvent gave a yellow oil (1.69 g) which was used directly in next step.
LC/MS (ES) m/e 207 (M+H)$^+$.

(c) Racemic 1,1-Dimethylethyl {[(2R,S)-4-(phenylmethyl)-2-morpholinyl]methyl}carbamate To a solution of crude racemic {[(2R,S)-4-(phenylmethyl)-2-morpholinyl]methyl}amine (1.69 g, 8.2 mmol) in DCM (15 mL) at 0° C. was added di-tert-butyl dicarbonate (1.88 g, 8.6 mmol). The cooling bath was removed and the reaction was stirred at room temperature for 2 h. The solvent was removed in vacuo and the resulting oil was purified on silica gel eluting with CHCl$_3$-methanol-NH$_4$OH, 96:4:1, providing the title compound as a white solid (1.94 g, 71% over 3 steps):
LC/MS (ES) m/e 307 (M+H)$^+$.

(d) 1,1-Dimethylethyl {[(2S)-4-(phenylmethyl)-2-morpholinyl]methyl}carbamate and 1,1-dimethylethyl {[(2R)-4-(phenylmethyl)-2-morpholinyl]methyl}carbamate Racemic 1,1-dimethylethyl {[(2R,S)-4-(phenylmethyl)-2-morpholinyl]methyl}carbamate (10 g) was resolved via chiral preparative HPLC into the two enantiomers E1 and E2 using a Chiralcel OD column, eluting with 95:5 hexane:ethanol to provide 1,1-dimethylethyl {[(2S-4-(phenylmethyl)-2-morpholinyl]methyl}carbamate (E2, second eluting, 4.9 g, 99% ee, $[\alpha]_D=-14.6°$) as a colorless oil and 1,1-dimethylethyl {[(2R)-4-(phenylmethyl)-2-morpholinyl]methyl}carbamate (E1, first eluting, 5.0 g, >98% ee, $[\alpha]_D+14.6°$) as a colorless oil.

(e) Title Compound

To a solution of 1,1-dimethylethyl {[(2S)-4-(phenylmethyl)-2-morpholinyl]methyl}carbamate (4.9 g, 16 mmol) in ethanol (160 mL) was added 10% Pd/C (1.5 μg). The suspension was hydrogenated at 50 psi for 8 h. The reaction was filtered through a pad of Celite® and the pad was washed several times with methanol. The filtrate was concentrated to afford the title compound (3.35 g, 97%) as a colorless solid which was not purified further: LC/MS (ES) m/e 217 $(M+H)^+$. The absolute stereochemistry of the title compound was determined by vibrational circular dichroism (VCD).

Preparation (E) (4S)-4-[(4-amino-1-piperidinyl)methyl]-4-hydroxy-3-(methyloxy)-4,5-dihydro-7H-pyrrolo[3,2,1-de]-1,5-naphthyridin-7-one enantiomer E1

(4S)-4-[(4-Amino-1-piperidinyl)methyl]-3-fluoro-4-hydroxy-4,5-dihydro-7H-pyrrolo[3,2,1-de]-1,5-naphthyridin-7-one, (enantiomer E1) was converted to its corresponding formate salt (0.72 g, 2 mmol), dissolved in methanol (7 mL) and then treated with sodium methoxide (25% in methanol, 1.3 mL, 6 mmol). The reaction was then heated at reflux under argon for approx. 2 h. The cooled mixture was treated with approx. 12 drops of aqueous ammonium chloride and evaporated to dryness. The residue was extracted twice with 20% methanol/dichloromethane and the extracts were filtered and evaporated to give the product (0.66 g, 100%).

MS (+ve ion electrospray) m/z 331 (MH+).

Biological Activity

Antimicrobial Activity Assay:

Whole-cell antimicrobial activity was determined by broth microdilution using the Clinical and Laboratory Standards Institute (CLSI) recommended procedure, Document M7-A7, "Methods for Dilution Susceptibility Tests for Bacteria that Grow Aerobically". The compounds were tested in serial two-fold dilutions ranging from 0.016 to 16 mcg/mL.

Compounds were evaluated against a panel of Gram-positive organisms, including *Staphylococcus aureus, Streptococcus pneumoniae, Streptococcus pyogenes, Enterococcus faecalis* and *Enterococcus faecium*.

In addition, compounds were evaluated against a panel of Gram-negative organisms including *Haemophilus influenzae, Moraxella catarrhalis, Escherichia coli, Pseudomonas aeruginosa, Proteus mirabilis, Legionella pneumophila, Enterobacter cloacae, Enterobacter aerogenes, Klebsiella pneumoniae* and *Stenotrophomonas maltophilia*.

The minimum inhibitory concentration (MIC) was determined as the lowest concentration of compound that inhibited visible growth. A mirror reader was used to assist in determining the MIC endpoint.

Each of the listed Examples, as identified in the present application, were tested in at least one exemplified salt form. Unless otherwise noted, the listed Examples had a MIC ≦2 μg/ml against a strain of at least one of the organisms listed above. Examples 24, 38 and 39 had an MIC ≦41 g/ml against a strain of at least one of the organisms listed above. Examples 47 and 65 had an MIC ≦8 μg/ml against a strain of at least one of the organisms listed above. The MIC values for Example 66 were >16 μg/ml against all of the strains representing the organisms listed above.

The invention claimed is:

1. A compound of formula (I) or a pharmaceutically acceptable salt or N-oxide thereof:

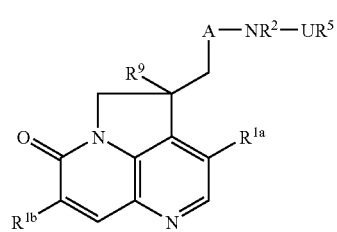

wherein:

$R^{1a}$ and $R^{1b}$ are independently selected from hydrogen; halogen; cyano;
$(C_{1-6})$alkyl; $(C_{1-6})$alkylthio; trifluoromethyl; trifluoromethoxy; carboxy; hydroxy optionally substituted with $(C_{1-6})$alkyl or $(C_{1-6})$alkoxy-substituted $(C_{1-6})$alkyl;
$(C_{1-6})$alkoxy-substituted $(C_{1-6})$alkyl; hydroxy $(C_{1-6})$alkyl; an amino group optionally N-substituted by one or two $(C_{1-6})$alkyl, formyl, $(C_{1-6})$alkylcarbonyl or
$(C_{1-6})$alkylsulphonyl groups; or aminocarbonyl wherein the amino group is optionally substituted by $(C_{1-4})$alkyl;
$R^2$ is hydrogen, or $(C_{1-4})$alkyl, or together with $R^6$ forms Y as defined below;
A is a group (ia) or (ib):

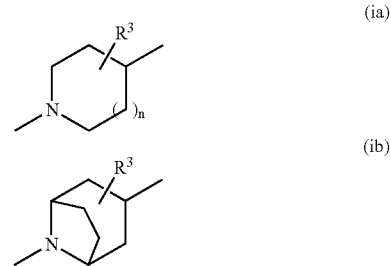

in which: $R^3$ is as defined for $R^{1a}$ or $R^{1b}$ or is oxo and n is 1 or 2:

or A is a group (ii)

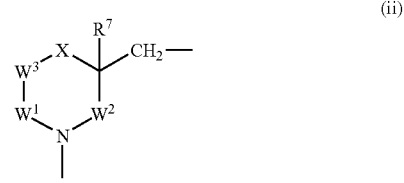

$W^1$, $W^2$ and $W^3$ are $CR^4R^8$
or $W^2$ and $W^3$ are $CR^4R^8$ and $W^1$ represents a bond between $W^3$ and N;
X is O, $CR^4R^8$, or $NR^6$;
one $R^4$ is as defined for $R^{1a}$ and $R^{1b}$ and the remainder and $R^8$ are hydrogen or one $R^4$ and $R^8$ are together oxo and the remainder are hydrogen;

R⁶ is hydrogen or (C₁₋₆)alkyl; or together with R² forms Y;

R⁷ is hydrogen; halogen; hydroxy optionally substituted with (C₁₋₆)alkyl; or (C₁₋₆)alkyl;

Y is CR⁴R⁸CH₂; CH₂CR⁴R⁸; (C═O); CR⁴R⁸; CR⁴R⁸(C═O); or (C═O)CR⁴R⁸;

or when X is CR⁴R⁸, R⁸ and R⁷ together represent a bond;

U is selected from CO, and CH₂ and

R⁵ is an optionally substituted bicyclic heterocyclic ring system (B):

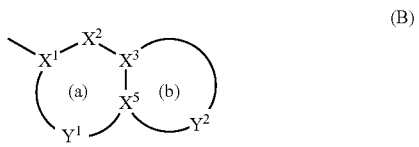

containing up to four heteroatoms in each ring in which at least one of rings (a) and (b) is aromatic;

X¹ is C or N when part of an aromatic ring, or CR¹⁴ when part of a non-aromatic ring;

X² is N, NR¹³, O, S(O)ₓ, CO or CR¹⁴ when part of an aromatic or non-aromatic ring or may in addition be CR¹⁴R¹⁵ when part of a non aromatic ring;

X³ and X⁵ are independently N or C;

Y¹ is a 0 to 4 atom linker group each atom of which is independently selected from N, NR¹³, O, S(O)ₓ, CO and CR¹⁴ when part of an aromatic or non-aromatic ring or may additionally be CR¹⁴R¹⁵ when part of a non aromatic ring;

Y² is a 2 to 6 atom linker group, each atom of Y² being independently selected from N, NR¹³, O, S(O)ₓ, CO, CR¹⁴ when part of an aromatic or non-aromatic ring or may additionally be CR¹⁴R¹⁵ when part of a non aromatic ring;

each of R¹⁴ and R¹⁵ is independently selected from: H; (C₁₋₄)alkylthio; halo; carboxy(C₁₋₄)alkyl; (C₁₋₄)alkyl; (C₁₋₄)alkoxycarbonyl; (C₁₋₄)alkylcarbonyl; (C₁₋₄)alkoxy(C₁₋₄)alkyl; hydroxy; hydroxy(C₁₋₄)alkyl; (C₁₋₄)alkoxy; nitro; cyano; carboxy; amino or aminocarbonyl optionally mono- or di-substituted by (C₁₋₄)alkyl; or R¹⁴ and R¹⁵ together represent oxo;

each R¹³ is independently H; trifluoromethyl; (C₁₋₄)alkyl optionally substituted by hydroxy, (C₁₋₆)alkoxy, (C₁₋₆)alkylthio, halo or trifluoromethyl; (C₂₋₄)alkenyl; (C₁₋₄)alkoxycarbonyl; (C₁₋₄)alkylcarbonyl; (C₁₋₆)alkylsulphonyl; aminocarbonyl wherein the amino group is optionally mono or disubstituted by (C₁₋₄)alkyl;

each x is independently 0, 1 or 2; and

R⁹ is fluoro or hydroxy.

2. A compound of formula (I) according to claim 1 or a pharmaceutically acceptable salt thereof or an N-oxide thereof wherein R¹ᵃ is chloro, fluoro or methoxy and R¹ᵇ is hydrogen, or R¹ᵃ is fluoro and R¹ᵇ is chloro or fluoro.

3. A compound of formula (I) according to claim 1 or a pharmaceutically acceptable salt thereof or an N-oxide thereof wherein R² is hydrogen.

4. A compound of formula (I) according to claim 1 or a pharmaceutically acceptable salt thereof or an N-oxide thereof wherein the stereochemistry at the carbon atom to which the group R⁹ is attached is S.

5. A compound of formula (I) according to claim 1 or a pharmaceutically acceptable salt thereof or an N-oxide thereof wherein A is a group (ia) in which n is 1 and R³ is hydrogen or hydroxy.

6. A compound of formula (I) according to claim 1 or a pharmaceutically acceptable salt thereof or an N-oxide wherein A is (ii), W¹ is a bond, X, W² and W³ are each CH₂ and R⁷ is H.

7. A compound of formula (I) according to claim 1 or a pharmaceutically acceptable salt thereof or an N-oxide thereof wherein U is CH₂.

8. A compound of formula (I) according to claim 1 or a pharmaceutically acceptable salt thereof or a N-oxide thereof wherein R⁵ is an aromatic heterocyclic ring (B) having 8-11 ring atoms, 2-4 of which ring atoms are heteroatoms at least one of which is N or NR¹³; wherein Y² contains 2-3 heteroatoms, one of which is S and 1-2 are N, with one N bonded to X³, or the heterocyclic ring (B) has ring (a) aromatic selected from optionally substituted benzo, pyrido and pyridazino and ring (b) non aromatic and Y² has 3-5 atoms, at least one of which is a heteroatom, with O, S, CH₂ or NR¹³ bonded to X⁵ where R¹³ is other than hydrogen, and either NHCO bonded via N to X³, or O, S, CH₂ or NH bonded to X³.

9. A compound of formula (I) according to claim 1 or a pharmaceutically acceptable salt thereof or an N-oxide thereof wherein R⁵ is selected from the group consisting of:

3-oxo-3,4-dihydro-2H-pyrido[3,2-b][1,4]oxazin-6-yl;
3-oxo-3,4-dihydro-2H-pyrido[3,2-b][1,4]thiazin-6-yl;
6,7-dihydro[1,4]dioxino[2,3-c]pyridazin-3-yl;
6,7-dihydro[1,4]oxathiino[2,3-c]pyridazin-3-yl;
6,7-dihydro[1,4]oxathiino[3,2-c]pyridazin-3-yl;
2,3-dihydro-[1,4]dioxino[2,3-c]pyridin-7-yl;
[1,3]oxathiolo[5,4-c]pyridin-6-yl;
2,3-dihydro-1,4-benzodioxin-6-yl;
2,3-dihydro[1,4]oxathiino[2,3-c]pyridin-7-yl;
3,4-dihydro-2H-pyrano[2,3-c]pyridin-6-yl;
2,3-dihydro[1,4]oxathiino[3,2-c]pyridin-7-yl; and
6,7-dihydro-5H-pyrano[2,3-c]pyridazin-3-yl.

10. A compound selected from the group consisting of:

(4S)-4-({4-[(2,3-Dihydro[1,4]dioxino[2,3-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one (4R/S)-4-({4-[(2,3-Dihydro[1,4]dioxino[2,3-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one;

(4R)-4-({4-[(2,3-Dihydro[1,4]dioxino[2,3-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one (4S)-4-({4-[(2,3-Dihydro-1,4-benzodioxin-6-ylmethyl)amino]-1-piperidinyl}methyl)-3-fluoro-4-hydroxy-4,5-dihydro-7H-pyrrolo[3,2,1-de]-1,5-naphthyridin-7-one;

(4S)-4-({4-[(3,4-Dihydro-2H-pyrano[2,3-c]pyridin-6-ylmethyl)amino]-1-piperidinyl}methyl)-3-fluoro-4-hydroxy-4,5-dihydro-7H-pyrrolo[3,2,1-de]-1,5-naphthyridin-7-one;

(4R)-4-({4-[(3,4-Dihydro-2H-pyrano[2,3-c]pyridin-6-ylmethyl)amino]-1-piperidinyl}methyl)-3-fluoro-4-hydroxy-4,5-dihydro-7H-pyrrolo[3,2,1-de]-1,5-naphthyridin-7-one (4S)-3-Fluoro-4-hydroxy-4-[(4-{[(3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one;

(4R)-3-Fluoro-4-hydroxy-4-[(4-{[(3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one (4S)-4-({4-[(2,3-Dihydro[1,4]oxathiino[2,3-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one;

(4R)-4-({4-[(2,3-Dihydro[1,4]oxathiino[2,3-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one;

(4S)-3-Fluoro-4-hydroxy-4-({4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one;

(4R)-3-Fluoro-4-hydroxy-4-({4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one (4R/S)-3-Chloro-4-({4-[(2,3-dihydro[1,4]dioxino[2,3-c]pyridin-7-ylmethyl)amino]-1-piperidinyl}methyl)-4-hydroxy-4,5-dihydro-7H-pyrrolo[3,2,1-de]-1,5-naphthyridin-7-one;

(4R/S)-3-Chloro-4-({4-[(3,4-dihydro-2H-pyrano[2,3-c]pyridin-6-ylmethyl)amino]-1-piperidinyl}methyl)-4-hydroxy-4,5-dihydro-7H-pyrrolo[3,2,1-de]-1,5-naphthyridin-7-one;

(4R/S)-3-Chloro-4-hydroxy-4-[(4-{[(3-oxo-3,4-dihydro-2H-pyrido[3,2-b][1,4]thiazin-6-yl)methyl]amino}-1-piperidinyl)methyl]-4,5-dihydro-7H-pyrrolo[3,2,1-de]-1,5-naphthyridin-7-one;

(4R/S)-3-Chloro-4-hydroxy-4-({4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one;

3,8-Difluoro-4-hydroxy-4-({4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one;

(4S)-3,8-Difluoro-4-hydroxy-4-({4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one;

(4S)-4-({4-[(6,7-Dihydro-5H-pyrano[2,3-c]pyridazin-3-ylmethyl)amino]-1-piperidinyl}methyl)-3-fluoro-4-hydroxy-4,5-dihydro-7H-pyrrolo[3,2,1-de]-1,5-naphthyridin-7-one;

(4S)-4-({4-[(6,7-Dihydro[1,4]oxathiino[2,3-c]pyridazin-3-ylmethyl)amino]-1-piperidinyl}methyl)-3-fluoro-4-hydroxy-4,5-dihydro-7H-pyrrolo[3,2,1-de]-1,5-naphthyridin-7-one;

(4S)-4-({4-[(6,7-Dihydro[1,4]oxathiino[3,2-c]pyridazin-3-ylmethyl)amino]-1-piperidinyl}methyl)-3-fluoro-4-hydroxy-4,5-dihydro-7H-pyrrolo[3,2,1-de]-1,5-naphthyridin-7-one;

(4R/S)-4-({4-[(2,3-Dihydro[1,4]dioxino[2,3-c]pyridin-7-ylmethyl)amino]-1-piperidinyl}methyl)-3,8-difluoro-4-hydroxy-4,5-dihydro-7H-pyrrolo[3,2,1-de]-1,5-naphthyridin-7-one or an enantiomer thereof;

(4S)-3-Fluoro-4-hydroxy-4-({4-[(2-quinoxalinylmethyl)amino]-1-piperidinyl}methyl)-4,5-dihydro-7H-pyrrolo[3,2,1-de]-1,5-naphthyridin-7-one;

(4S)-4-({4-[(2,3-Dihydro[1,4]oxathiino[3,2-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one;

(4R/S)-8-Chloro-4-({4-[(2,3-dihydro[1,4]dioxino[2,3-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one;

(4R/S)-8-Chloro-3-fluoro-4-hydroxy-4-({4-[([1,3]oxathiolo[5,4-c]pyridin-6-ylmethyl)amino]-1-piperidinyl}methyl)-4,5-dihydro-7H-pyrrolo[3,2,1-de]-1,5-naphthyridin-7-one;

4-({4-[(2,3-Dihydro[1,4]dioxino[2,3-c]pyridin-7-ylmethyl)amino]-1-piperidinyl}methyl)-3,4-difluoro-4,5-dihydro-7H-pyrrolo[3,2,1-de]-1,5-naphthyridin-7-one or an enantiomer thereof;

4-({4-[(6,7-Dihydro[1,4]oxathiino[2,3-c]pyridazin-3-ylmethyl)amino]-1-piperidinyl}methyl) -3,4-difluoro-4,5-dihydro-7H-pyrrolo[3,2,1-de]-1,5-naphthyridin-7-one;

4-({4-[(6,7-Dihydro[1,4]dioxino[2,3-c]pyridazin-3-ylmethyl)amino]-1-piperidinyl}methyl) -3,4-difluoro-4,5-dihydro-7H-pyrrolo[3,2,1-de]-1,5-naphthyridin-7-one or an enantiomer thereof;

An enantionmer of 3,4-Difluoro-4-[(4-{[(3-oxo-3,4-dihydro-2H-pyrido[3,2-b][1,4]oxazin-6-yl)methyl]amino}-1-piperidinyl)methyl]-4,5-dihydro-7H-pyrrolo[3,2,1-de]-1,5-naphthyridin-7-one; and An enantiomer of 4-({4-[(6,7-Dihydro-5H-pyrano[2,3-c]pyridazin-3-ylmethyl)amino]-1-piperidinyl}methyl)-3,4-difluoro-4,5-dihydro-7H-pyrrolo[3,2,1-de]-1,5-naphthyridin-7-one;

or a pharmaceutically acceptable salt or N-oxide thereof.

11. (4S)-4-({4-[(2,3-Dihydro[1,4]dioxino[2,3-c]pyridin-7-ylmethyl)amino]-1-piperidinyl}methyl)-3-fluoro-4-hydroxy-4,5-dihydro-7H-pyrrolo[3,2,1-de]-1,5-naphthyridin-7-one hydrochloride.

12. A method of treatment of a bacterial infection which method comprises administering to a mammal in need of such treatment an effective amount of a compound of formula (I) according to claim 1 or a pharmaceutically acceptable salt thereof or an N-oxide thereof, wherein the bacterial infection is selected from the group consisting of *Staphylococcus aureus, Streptococcus pneumoniae, Streptococcus pyogenes, Enterococcus faecalis, Enterococcus faecium, Haemophilus influenzae, Moraxella catarrhalis, Escherichia coli, Pseudomonas aeruginosa, Proteus mirabilis, Enterobacter cloacae, Enterobacter aerogenes, Klebsiella pneumoniae* and *Stenotrophomonas maltophilia*.

13. A pharmaceutical composition comprising a compound of formula (I) according to claim 1 or a pharmaceutically acceptable salt thereof or an N-oxide thereof; and a pharmaceutically acceptable carrier.

14. A method of treatment according to claim 12 wherein the mammal is man.

15. A compound according to claim 1, which is a compound of formula (I) or a pharmaceutically acceptable salt thereof.

16. A compound selected from the group consisting of:

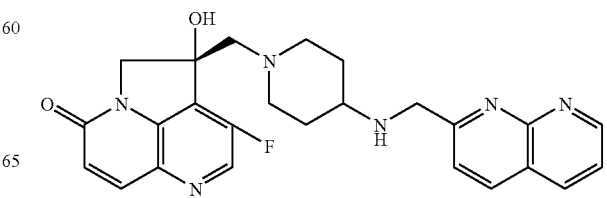

-continued
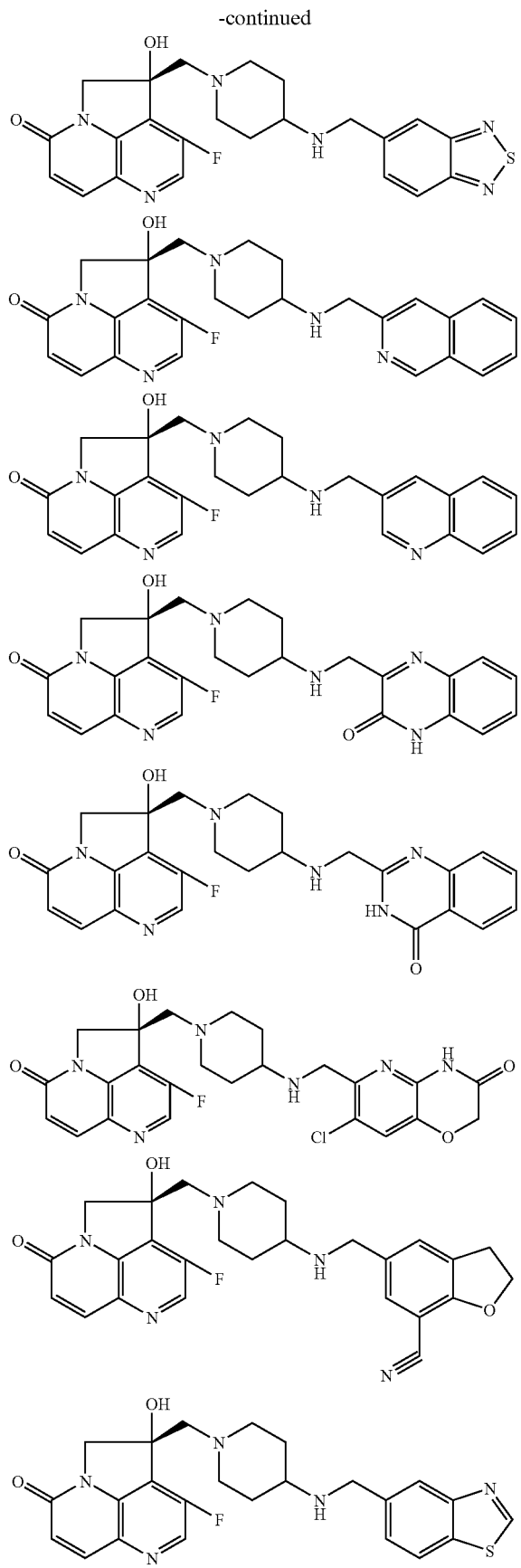
-continued
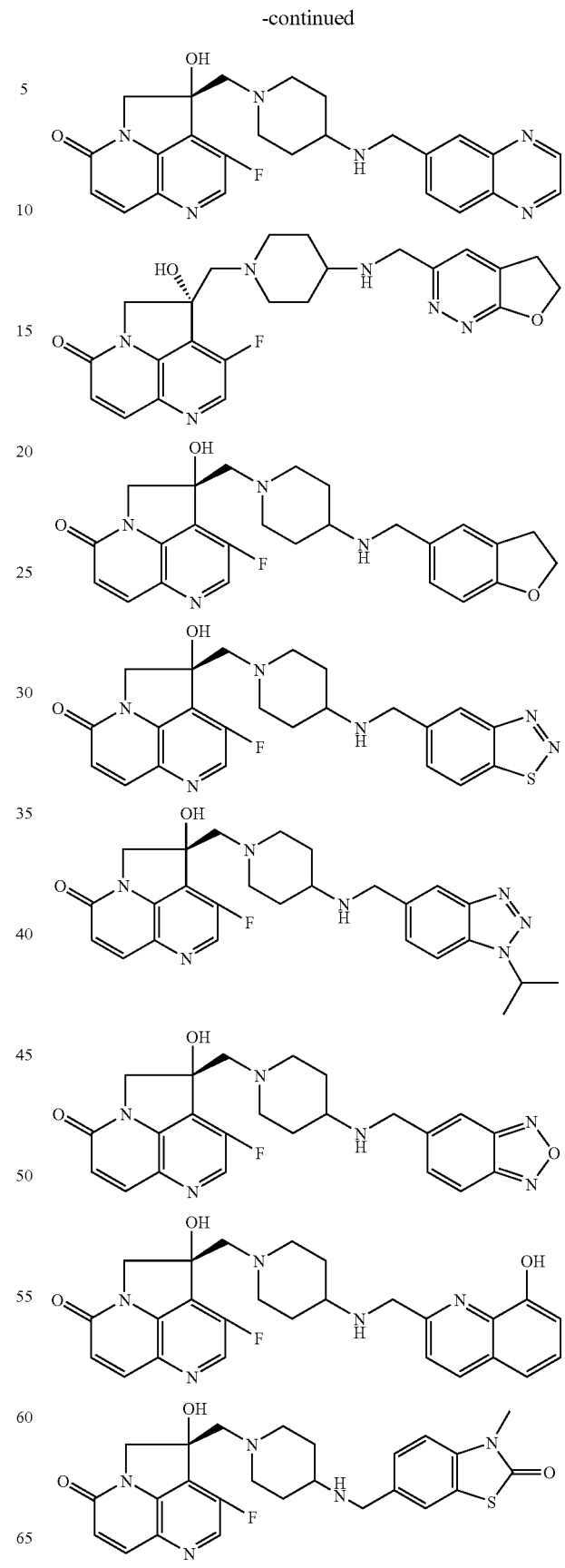

-continued
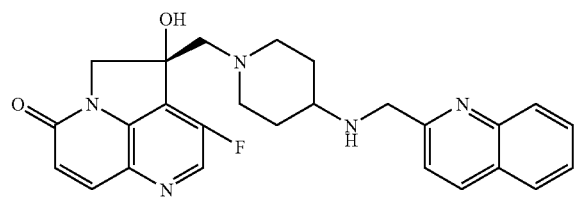
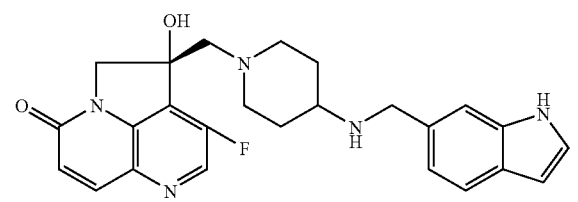
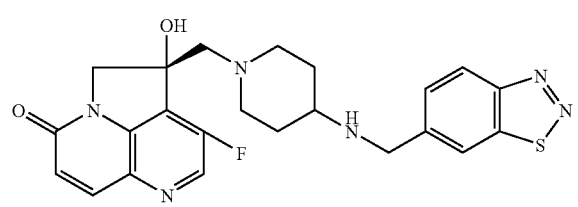
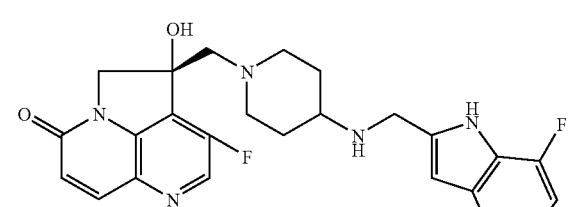
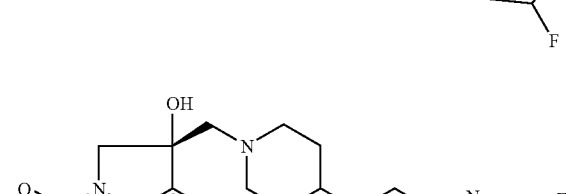
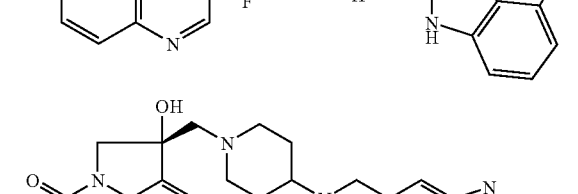 and
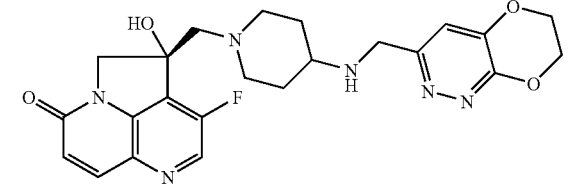
or a pharmaceutically acceptable salt or N-oxide thereof.
17. A compound selected from the group consisting of:
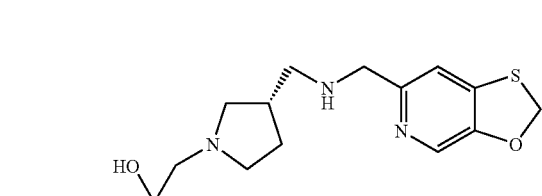
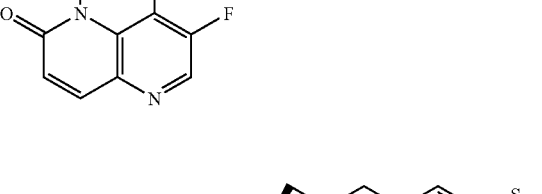
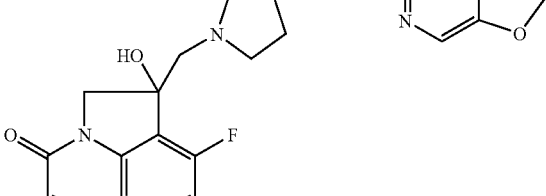
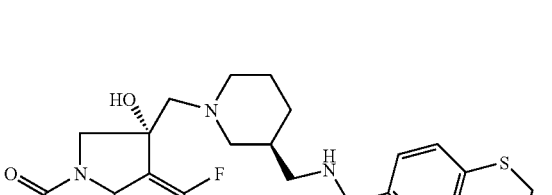
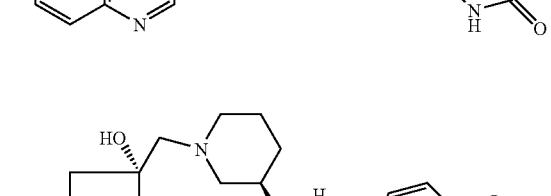
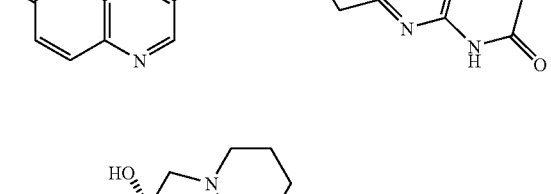
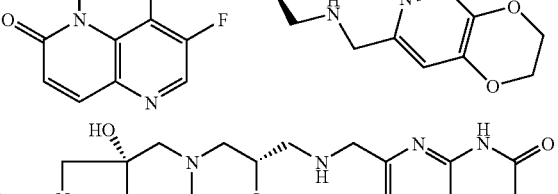

-continued
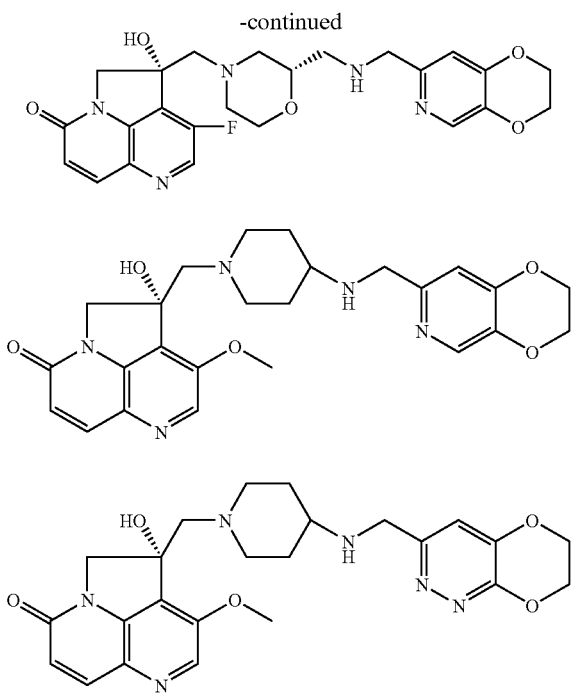
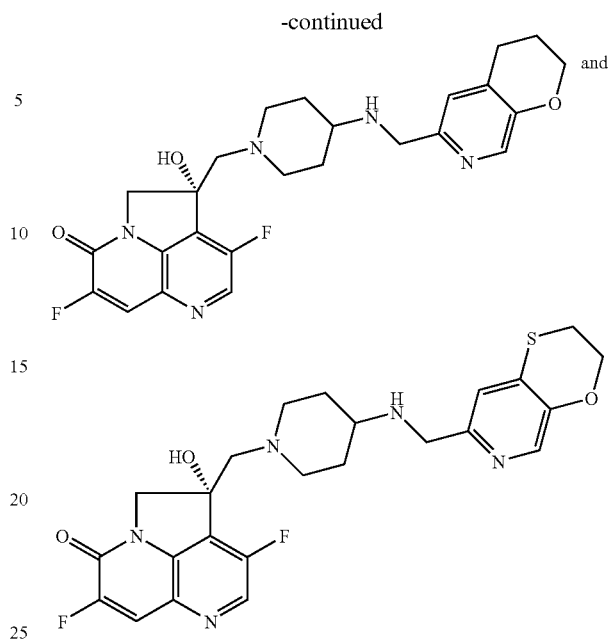
or a pharmaceutically acceptable salt or N-oxide thereof.
* * * * *